(12) United States Patent
Kühnert et al.

(10) Patent No.: US 8,399,673 B2
(45) Date of Patent: Mar. 19, 2013

(54) SUBSTITUTED 2-MERCAPTOQUINOLINE-3-CARBOXAMIDES AS KCNQ2/3 MODULATORS

(75) Inventors: Sven Kühnert, Düren (DE); Gregor Bahrenberg, Monschau-Konzen (DE); Achim Kless, Aachen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/523,955

(22) Filed: Jun. 15, 2012

(65) Prior Publication Data

US 2012/0252841 A1 Oct. 4, 2012

Related U.S. Application Data

(63) Continuation of application No. 12/720,864, filed on Mar. 10, 2010.

(60) Provisional application No. 61/159,544, filed on Mar. 12, 2009.

(30) Foreign Application Priority Data

Mar. 12, 2009 (EP) .................................. 09003597

(51) Int. Cl.
| | |
|---|---|
| C07D 215/54 | (2006.01) |
| C07D 401/12 | (2006.01) |
| C07D 405/12 | (2006.01) |
| C07D 409/12 | (2006.01) |
| C07D 413/12 | (2006.01) |
| C07D 417/12 | (2006.01) |

(52) U.S. Cl. .................................................. 546/156
(58) Field of Classification Search .................. None
See application file for complete search history.

(56) References Cited

U.S. PATENT DOCUMENTS

| | | |
|---|---|---|
| 2002/0128277 A1 | 9/2002 | Dworetzky et al. |
| 2010/0234419 A1 | 9/2010 | Kuhnert et al. |
| 2010/0234421 A1 | 9/2010 | Kuhnert et al. |
| 2010/0234428 A1 | 9/2010 | Kuhnert et al. |
| 2010/0234429 A1 | 9/2010 | Kuhnert et al. |

FOREIGN PATENT DOCUMENTS

| | | |
|---|---|---|
| DE | 27 06 977 A1 | 8/1978 |
| EP | 0 480 258 A1 | 9/1991 |
| EP | 0 716 077 A1 | 6/1996 |
| EP | 0 900 824 A1 | 3/1999 |
| EP | 1 449 841 A1 | 8/2004 |
| FR | 2 532 939 A1 | 3/1984 |
| WO | 96 26925 A1 | 9/1996 |
| WO | 00 42026 A1 | 7/2000 |
| WO | 01 10380 A2 | 2/2001 |
| WO | 01 10381 A2 | 2/2001 |
| WO | 02 066036 A1 | 8/2002 |
| WO | 02 074388 A1 | 9/2002 |
| WO | 02 081728 A2 | 10/2002 |
| WO | 2004 026816 A1 | 4/2004 |
| WO | 2004 058704 A2 | 7/2004 |
| WO | 2004 058704 A3 | 7/2004 |
| WO | 2005 035514 A2 | 4/2005 |
| WO | 2005 105733 A1 | 11/2005 |
| WO | 2006 051311 A1 | 5/2006 |
| WO | 2006 092143 A1 | 9/2006 |
| WO | 2006 122799 A1 | 11/2006 |
| WO | 2006 122800 A1 | 11/2006 |
| WO | 2007 015767 A1 | 2/2007 |
| WO | 2007 030582 A2 | 3/2007 |
| WO | 2007 057447 A1 | 5/2007 |
| WO | 2008 011080 A2 | 1/2008 |
| WO | 2008 011110 A2 | 1/2008 |
| WO | 2008 012532 A2 | 1/2008 |
| WO | 2008 046582 A1 | 4/2008 |
| WO | 2009 018466 A1 | 2/2009 |
| WO | 2009 019149 A1 | 2/2009 |
| WO | 2009 052078 A1 | 4/2009 |

OTHER PUBLICATIONS

Bennett et al; "A peripheral mononeuropathy in rat that produces disorders of pain sensation like those seen in man" Pain, 33 (1988) 87-107.

Gordon Blackburn-Munro; "The anticonvulsant retigabine attenuates nociceptive behaviours in rat models of persistent and neuropathic pain"; European Journal of Pharmacology 460 (2003) 109-116.

De Sarro et al; "Influence of retigabine on the anticonvulsant activity of some antiepileptic drugs against audiogenic seizures in DBA/2 mice"; Naunyn-Schmiedeberg's Arch Pharmacol (2001) 363: 330-336.

Dencker; "Effect of the new antiepileptic drug retigabine in a rodent model of mania"; ScienceDirect, Epilepsy & Behavior 12 (2008) 49-53.

Dost et al; "The anti-hyperalgesic activity of retigabine is mediated by KCNQ potassium channel activation"; Naunyn-Schmiedeberg's Arch Pharmacol (2004) 369 : 382-390.

Dubuisson et al; "The formalin test: A quantitative study of the analgesic effects of morphine, meperidine, and brain stem stimulation in rats and cats" Pain, 4 (1977) 161-174.

Gribkoff; "The therapeutic potential of neuronal Kv7 (KCNQ) channel modulators: an update"; Expert Opin. Ther. Targets (2008) 12(5): 565-581.

Gribkoff; "The therapeutic potential of neuronal KCNQ channel modulators" Expert Opin. Ther. Targets (2003) 7(6): 737-748.

Hansen et al: "The neuronal KCNQ channel opener retigabine inhibits locomotor activity and reduces forebrain excitatory responses to the psychostimulants cocaine, methylphenidate and phencyclidine"; ScienceDirect, European Journal of Pharmacology 570 (2007) 77-88.

(Continued)

*Primary Examiner* — Janet Andres
*Assistant Examiner* — Timothy R Rozof
(74) *Attorney, Agent, or Firm* — Norris McLaughlin & Marcus, P.A.

(57) ABSTRACT

The invention relates to substituted 2-mercaptoquinoline-3-carboxamides, methods for the preparation thereof, medicaments containing these compounds and the use of these compounds for the preparation of medicaments.

14 Claims, No Drawings

OTHER PUBLICATIONS

Kim, et al; "An experimental model for peripheral neuropathy produced by segmental spinal nerve ligation in the rat"; Pain, 50 (1992) 355-363.

Korsgaard, et al; "Anxiolytic Effects of Maxipost (BMS-204352) and Retigabine via Activation of Neuronal Kv7 Channels"; The Journal of Pharmacology and Experimental Therapeutics vol. 314, No. 1:282-292, 2005.

Litchfield, Jr. et al; "A simplified method of evaluating dose-effect experiments"; Stamford Research Laboratories, American Cyanamid Company, Stamford, Connecticut, Royal Society of Medicine 1948; pp. 99-113.

Miceli, et al; "Molecular pharmacology and therapeutic potential of neuronal Kv7-modulating drugs"; ScienceDirect, Current Opinion in Pharmacology 2008, 8:65-74.

Nielsen, et al; "Pharmacological characterisation of acid-induced muscle allodynia in rats"; ScienceDirect, European Journal of Pharmacology 487 (2004) 93-103.

Passmore, et al; "KCNQ/M Currents in Sensory Neurons: Significance for Pain Therapy"; The Journal of Neuroscience, Aug. 6, 2003 • 23(18):7227-7236 • 7227.

Richte, et al; "Antidystonic effects of Kv7 (KCNQ) channel openers in the dtsz mutant, an animal model of primary paroxysmal dystonia"; British Journal of Pharmacology (2006) 149, 747-753.

Streng, et al; "Urodynamic effects of the K+ channel (KCNQ) opener retigabine in freely moving, conscious rats"; The Journal of Urology, vol. 172, 2054-2058, Nov. 2004.

Wickenden et al; "KCNQ potassium channels: drug targets for the treatment of epilepsy and pain"; Expert Opinion, Ther. Patents (2004) 14(4): 457-469.

Wermuth, Camille G., "Molecular Variations Based on Isosteric Replacements", The Practice of Medicinal Chemistry, (1996) 203-237.

Yoo et al, "Beckmann rearrangement using indium (III) chloride: synthesis of substituted oxazoloquinolines from the corresponding ketoximes of 3-acyl-1H-quinolin-4-ones"; Synthesis (2006), No. 10, pp. 1599-1612.

CAPLUS 1972:59403.

F. A. Carey, R. J. Sundberg, Advanced Organic Chemistry, Parts A and B, Springer, 5th edition, 2007.

D'Amour and Smith (J. Pharm. Exp. Ther. 72, 74 79 (1941).

J. Mar., Advanced Organic Chemistry, Wiley & Sons, 6th edition, 2007.

Patani, G. et al, Bioisosterism: a ratiional approach in drug design, Chem. Rev. 1996, pp. 3147-3176.

Silverman, R. The organic chemistry of drug design and drug action, 2004, Elsevier, 2nd edition, p. 9.

F. Zaragoza Dorwald; "Side reactions in organic synthesis; a guide to successful synthesis design"; Wiley-VCH, Wwinheim, Preface, p. ix (2005).

Hewawasam et al; The synthesis and structure-activity relationship of 3-amino-4-benzylquinolin-2-ones: discovery of novel KCNQ2 channel openers; 14 BIOORG. & Med. Chem. Letters, 1615-18 (2004).

Martin, Yvonne, et al., "Do structurally similar molecules have similar biological activity?"; 45 J. Med. Chem. 4350-4358, 4536 (2002).

SUBSTITUTED 2-MERCAPTOQUINOLINE-3-CARBOXAMIDES AS KCNQ2/3 MODULATORS

This application is a continuation of U.S. Non-Provisional patent application Ser. No. 12/720,864, filed Mar. 10, 2010, now pending, which, in turn, claims priority of U.S. Provisional Application No. 61/159,544, filed Mar. 12, 2009; and European Patent Application No. 09003597.3, filed Mar. 12, 2009; the entire contents of which three applications is incorporated herein by reference.

The invention relates to substituted 2-mercaptoquinoline-3-carboxamides, methods for the preparation thereof, medicaments containing these compounds and the use of these compounds for the preparation of medicaments.

The treatment of pain, in particular neuropathic pain, is of great importance in medicine. There is a worldwide need for effective pain therapies. The urgent need for action to find targeted, patient-appropriate treatment for chronic and non-chronic pain conditions, this being understood as the successful and satisfactory treatment of pain for the patient, is also documented in the large number of scientific works that have been published in recent times in the field of applied analgesics and basic research into nociception.

A pathophysiological feature of chronic pain is the over-excitability of neurons. Neuronal excitability is decisively influenced by the activity of $K^+$ channels, since these significantly determine the resting potential of the cell and hence the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarisation of the cell membrane and, accompanying this, to a decrease in the electrical excitability of these neurons. KCNQ2/3-expressing neurons of the dorsal root ganglia are involved in the transmission of nociceptive stimuli from the periphery into the spinal cord (Passmore et al., J. Neurosci. 2003; 23(18):7227-36).

It has accordingly been possible to detect an analgesic activity in preclinical neuropathic and inflammatory pain models for the KCNQ2/3 agonist retigabine (Blackburn-Munro and Jensen, Eur J. Pharmacol. 2003; 460(2-3):109-16; Dost et al., Naunyn Schmiedeberg's Arch Pharmacol 2004; 369(4): 382-390).

The KCNQ2/3 $K^+$ channel thus represents a suitable starting point for the treatment of pain; in particular pain chosen from the group consisting of chronic pain, neuropathic pain, inflammatory pain and muscular pain (Nielsen et al., Eur J. Pharmacol. 2004; 487(1-3): 93-103), in particular neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety states (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53), dystonia-associated dyskinesias (Richter et al., Br J Pharmacol 2006, 149(6): 747-53).

There is a need for further compounds having comparable or better properties, not only in regard to affinity for KCNQ2/3 as such (potency, efficacy).

For instance, it can be advantageous to improve the metabolic stability, the solubility in aqueous media or the permeability of the compounds. These factors can have a beneficial effect on oral bioavailability or can alter the PK/PD (pharmacokinetic/pharmacodynamic) profile, which can lead to a more favourable period of action, for example.

A weak or non-existent interaction with transporter molecules, which are involved in the uptake and excretion of medicaments, can also be taken as an indication of improved bioavailability and at most low medicament interaction. Furthermore, interactions with the enzymes involved in the breakdown and excretion of medicaments should also be as low as possible, since such test results likewise indicate that at most low or even no medicament interactions whatsoever are to be anticipated.

It can further be advantageous if the compounds exhibit a high selectivity towards other receptors of the KCNQ family (specificity), for example towards KCNQ1, KCNQ3/5 or KCNQ4. A high selectivity can have a favourable effect on the side-effects profile. It is known, for example, that compounds which (also) bind to KCNQ1 are associated with a high risk of cardiac side effects, for which reason a high selectivity towards KCNQ1 can be desirable. A high selectivity towards other receptors can also be advantageous, however. A low affinity for the hERG ion channel or for the L-type calcium ion channel (phenyl alkylamine, benzothiazepine, dihydropyridine binding sites) can be advantageous, as these receptors are associated with the occurrence of cardiac side effects. Overall an improved selectivity with regard to binding to other endogenous proteins (i.e. receptors or enzymes for example) can lead to an improvement in the side-effects profile and hence to an improved compatibility.

An object of the invention was therefore to provide novel compounds having advantages over the prior art compounds. The compounds should in particular be suitable as pharmacological active ingredients in medicaments, preferably in medicaments for the treatment of disorders or diseases which are at least partly mediated by KCNQ2/3 $K^+$ channels.

This object is achieved by the subject matter of the claims.

Substituted quinolinyl compounds are known from the prior art which are suitable as inhibitors of hYAK1 and hYAK3 kinases (WO 02/081728 A2). Furthermore 4-hydroxyquinoline-3-carboxylic acid derivatives are known as light stabilisers (EP 0 900 824 A1).

Surprisingly it has been found that substituted 2-mercaptoquinoline-3-carboxamides having the general formula (1) given below are suitable for the treatment of pain. It has further surprisingly been found that substituted 2-mercaptoquinoline-3-carboxamides having the general formula (1) given below also have an excellent affinity for the KCNQ2/3 $K^+$ channel and are therefore suitable for the treatment of disorders or diseases which are at least partly mediated by KCNQ2/3 $K^+$ channels. The substituted 2-mercaptoquinoline-3-carboxamides act here as modulators, i.e. agonists or antagonists, of the KCNQ2/3 $K^+$ channel.

The invention provides substituted 2-mercaptoquinoline-3-carboxamides having the general formula (1)

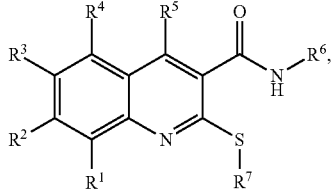

wherein
$R^0$ stands for $C_{1-10}$ alkyl or $C_{2-10}$ heteroalkyl, each saturated or unsaturated, branched or unbranched, unsubstituted or mono- or polysubstituted; $C_{3-10}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl- or $C_{2-8}$ heteroalkyl-bridged $C_{3-10}$ cycloalkyl or heterocyclyl, each saturated or unsaturated, unsubstituted or mono- or polysubstituted, wherein the alkyl or heteroalkyl chain can in each case be branched or unbranched, saturated or unsaturated, unsubstituted, mono- or polysubstituted; or $C_{1-8}$ alkyl- or $C_{2-8}$ heteroalkyl-bridged aryl or heteroaryl, each unsubstituted or mono- or polysubstituted, wherein the alkyl or heteroalkyl chain can in each case be branched or unbranched, saturated or unsaturated, unsubstituted, mono- or polysubstituted;
$R^1$, $R^2$, $R^3$, $R^4$ each denote independently of one another H; F; Cl; Br; I; $NO_2$; $CF_3$; CN; $R^0$; C(=O)H; C(=O)$R^0$; $CO_2H$; C(=O)O$R^0$; $CONH_2$; C(=O)NH$R^0$; C(=O)N(R)$_2$; OH; O$R^0$; O—C(=O)—$R^0$; O—C(=O)—O—$R^0$; O—(C=O)—NH—$R^0$; O—C(=O)—N(R)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N(R)$_2$; $NH_2$; NH—$R^0$; N(R)$_2$; NH—C(=O)—$R^0$; NH—C(=O)—O—$R^0$; NH—C(=O)—$NH_2$; NH—C(=O)—NH—$R^0$; NH—C(=O)—N(R)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2R^0$; NH—S(=O)$_2$O$R^0$; NH—S(=O)$_2$NH$_2$; NH—S(=O)$_2$NH$R^0$; NH—S(=O)$_2$N(R)$_2$; $NR^0$—S(=O)$_2$OH; $NR^0$—S(=O)$_2R^0$; $NR^0$—S(=O)$_2$O$R^0$; $NR^0$—S(=O)$_2$NH$_2$; $NR^0$—S(=O)$_2$NH$R^0$; $NR^0$—S(=O)$_2$N($R^0$)$_2$; SH; S$R^0$; S(=O)$R^0$; S(=O)$_2R^0$; S(=O)$_2$OH; S(=O)$_2$O$R^0$; S(=O)$_2$NH$_2$; S(=O)$_2$NH$R^0$; or S(=O)$_2$N(R)$_2$;
$R^5$ stands for H; F; Cl; Br; I; $NO_2$; $CF_3$; CN; $R^0$; C(=O)H; C(=O)$R^0$; $CO_2H$; C(=O)O$R^0$; $CONH_2$; C(=O)NH$R^0$; C(=O)N($R^0$)$_2$; O$R^0$; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2R^0$; NH—S(=O)$_2$O$R^0$; NH—S(=O)$_2$NH$_2$; NH—S(=O)$_2$NH$R^0$; NH—S(=O)$_2$N(R)$_2$; $NR^0$—S(=O)$_2$OH; $NR^0$—S(=O)$_2R^0$; $NR^0$—S(=O)$_2$O$R^0$; $NR^0$—S(=O)$_2$NH$_2$; $NR^0$—S(=O)$_2$NH$R^0$; $NR^0$—S(=O)$_2$N($R^0$)$_2$; SH; S$R^0$; S(=O)$R^0$; S(=O)$_2R^0$; S(=O)$_2$OH; S(=O)$_2$O$R^0$; S(=O)$_2$NH$_2$; S(=O)$_2$NH$R^0$; or S(=O)$_2$N(R)$_2$;
$R^6$ stands for $R^0$, with the proviso that if $R^0$ denotes heterocyclyl, saturated or unsaturated, unsubstituted or mono- or polysubstituted, or heteroaryl, unsubstituted or mono- or polysubstituted, then the binding of the heteroaryl or heterocyclyl is made via a carbon atom of the heteroaryl or heterocyclyl;
$R^7$ stands for $R^0$, with the proviso that if $R^0$ denotes heterocyclyl, saturated or unsaturated, unsubstituted or mono- or polysubstituted, or heteroaryl, unsubstituted or mono- or polysubstituted, then the binding of the heteroaryl or heterocyclyl is made via a carbon atom of the heteroaryl or heterocyclyl;
wherein "alkyl substituted", "heteroalkyl substituted", "heterocyclyl substituted" and "cycloalkyl substituted" stands for the substitution of one or more hydrogen atoms, each independently of one another, with F; Cl; Br; I; CN; $CF_3$; =O; =NH; =C(NH$_2$)$_2$; $NO_2$; $R^0$; C(=O)H; C(=O)$R^0$; $CO_2H$; C(=O)O$R^0$; $CONH_2$; C(=O)NH$R^0$; C(=O)N(R)$_2$; OH; O$R^0$; —O—($C_{1-8}$ alkyl)-O—; O—C(=O)—$R^0$; O—C(=O)—O—$R^0$; O—(C=O)—NH—$R^0$; O—C(=O)—)N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2R^0$; NH—S(=O)$_2$O$R^0$; NH—S(=O)$_2$NH$_2$; NH—S(=O)$_2$NH$R^0$; NH—S(=O)$_2$N(R)$_2$; $NR^0$—S(=O)$_2$OH; $NR^0$—S(=O)$_2R^0$; $NR^0$—S(=O)$_2$O$R^0$; $NR^0$—S(=O)$_2$NH$_2$; $NR^0$—S(=O)$_2$NH$R^0$; $NR^0$—S(=O)$_2$N($R^0$)$_2$; SH; S$R^0$; S(=O)$R^0$; S(=O)$_2R^0$; S(=O)$_2$OH; S(=O)$_2$O$R^0$; S(=O)$_2$NH$_2$; S(=O)$_2$NH$R^0$; S(=O)$_2$N(R)$_2$;
wherein "aryl substituted" and "heteroaryl substituted" stands for the substitution of one or more hydrogen atoms, each independently of one another, with F; Cl; Br; I; $NO_2$; $CF_3$; CN; $R^0$; C(=O)H; C(=O)$R^0$; $CO_2H$; C(=O)O$R^0$; $CONH_2$; C(=O)NH$R^0$; C(=O)N($R^0$)$_2$; OH; O$R^0$; —O—($C_{1-8}$ alkyl)-O—; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; $NR^0$—C(=O)—$R^0$; $NR^0$—C(=O)—O—$R^0$; $NR^0$—C(=O)—$NH_2$; $NR^0$—C(=O)—NH—$R^0$; $NR^0$—C(=O)—N($R^0$)$_2$; NH—S(=O)$_2$OH; NH—S(=O)$_2R^0$; NH—S(=O)$_2$O$R^0$; NH—S(=O)$_2$NH$_2$; NH—S(=O)$_2$NH$R^0$; NH—S(=O)$_2$N(R)$_2$; $NR^0$—S(=O)$_2$OH; $NR^0$—S(=O)$_2R^0$; $NR^0$—S(=O)$_2$O$R^0$; $NR^0$—S(=O)$_2$NH$_2$; $NR^0$—S(=O)$_2$NH$R^0$; $NR^0$—S(=O)$_2$N($R^0$)$_2$; SH; S$R^0$; S(=O)$R^0$; S(=O)$_2R^0$; S(=O)$_2$OH; S(=O)$_2$O$R^0$; S(=O)$_2$NH$_2$; S(=O)$_2$NH$R^0$; S(=O)$_2$N(R)$_2$;
with the exception of the following compound:
N-benzyl-2-(3-chloro-2-hydroxypropylthio)-4-(2,4-dichlorophenyl)quinoline-3-carboxamide;
in the form of the free compounds or salts of physiologically compatible acids or bases.

Within the meaning of this invention the expressions "alkyl" or "$C_{1-10}$ alkyl", "$C_{1-8}$ alkyl" and "$C_{1-4}$ alkyl" include acyclic saturated or unsaturated aliphatic hydrocarbon radicals, which can be branched or unbranched and unsubstituted or mono- or polysubstituted, having respectively 1 to 10 or 1 to 8 or 1 to 4 C atoms, i.e. $C_{1-10}$ alkanyls, $C_{2-10}$ alkenyls and $C_{2-10}$ alkynyls or $C_{1-8}$ alkanyls, $C_{2-8}$ alkenyls and $C_{2-8}$ alkynyls or $C_{1-4}$ alkanyls, $C_{2-4}$ alkenyls and $C_{2-4}$ alkynyls. Alkenyls have at least one C—C double bond and alkynyls have at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl(vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl, heptenyl, heptynyl, octenyl, octynyl, nonenyl, nonynyl, decenyl and decynyl.

Within the meaning of this invention the expressions "heteroalkyl" or "$C_{2-10}$ heteroalkyl" and "$C_{2-8}$ heteroalkyl" include acyclic aliphatic saturated or unsaturated hydrocarbon radicals having 2 to 10 C atoms, i.e. $C_{2-10}$ heteroalkanyls, $C_{2-10}$ heteroalkenyls and $C_{2-10}$ heteroalkynyls, or having 2 to 8 C atoms, i.e. $C_{2-8}$ heteroalkanyls, $C_{2-8}$ heteroalkenyls and $C_{2-8}$ heteroalkynyls, which can each be branched or unbranched and unsubstituted or mono- or polysubstituted and in which at least one, optionally also two or three carbon atoms are replaced by a heteroatom or a heteroatom group selected independently of one another from the group consisting of O, S, S(=O), S(=O)$_2$, N, NH, and N($C_{1-8}$ alkyl), preferably N($CH_3$), wherein the initial carbon atom of a $C_{2-10}$ heteroalkyl or a $C_{2-8}$ heteroalkyl via which the $C_{2-10}$ heteroalkyl or the $C_{2-8}$ heteroalkyl is bound to the higher-order general structure cannot be replaced by a heteroatom or a heteroatom group and adjacent carbon atoms cannot simultaneously be replaced by a heteroatom or a heteroatom group. The heteroatom groups NH and N($C_{1-8}$ alkyl) of the heteroalkyl can optionally be mono- or polysubstituted. $C_{2-10}$ heteroalkenyls and $C_{2-8}$ heteroalkenyls have at least one C—C or one C—N double bond and $C_{2-10}$ heteroalkynyls and $C_{2-8}$ heteroalkynyls have at least one C—C triple bond. Heteroalkyl is preferably selected from the group comprising —$CH_2$—O—$CH_3$, —$CH_2$—$CH_2$—O—$CH_3$, —$CH_2$—$CH_2$—O—$CH_2$—$CH_3$, —$CH_2$—$CH_2$—O—$CH_2$—$CH_2$—O—$CH_3$, —CH=CH—O—$CH_3$, —CH=CH—O—$CH_2$—$CH_3$, =CH—O—$CH_3$, =CH—O—$CH_2$—$CH_3$, =CH—$CH_2$—O—$CH_2$—$CH_3$, =CH—$CH_2$—O—$CH_3$, —$CH_2$—NH—$CH_3$, —$CH_2$—$CH_2$—NH—$CH_3$, —$CH_2$—$CH_2$—NH—$CH_2$—$CH_3$, —$CH_2$—$CH_2$—NH—$CH_2$—$CH_3$, —$CH_2$—$CH_2$—NH—$CH_3$, —CH=CH—NH—$CH_3$, —CH=CH—NH—$CH_2$—$CH_3$, —CH=CH—N($CH_3$)—$CH_2$—$CH_3$, =CH—NH—$CH_3$, =CH—NH—$CH_2$—$CH_3$, =CH—$CH_2$—NH—$CH_2$—$CH_3$, =CH—$CH_2$—NH—$CH_3$, —$CH_2$—N($CH_3$)—$CH_3$, —$CH_2$—$CH_2$—N($CH_3$)—$CH_3$, —$CH_2$—$CH_2$—N($CH_3$)—$CH_2$—$CH_3$, —$CH_2$—$CH_2$—N($CH_3$)—$CH_3$, —$CH_2$—$CH_2$—N($CH_3$)—$CH_3$, $CH_2$—$CH_2$—NH—$CH_2$—$CH_2$—O—$CH_3$, $CH_2$—$CH_2$—O—$CH_2$—$CH_2$—NH—$CH_3$, —$CH_2$—$CH_2$—N($CH_3$)—$CH_2$—$CH_2$—O—$CH_3$, $CH_2$—$CH_2$—O—$CH_2$—$CH_2$—N($CH_3$)—$CH_3$, $CH_2$—NH—$CH_2$—O—$CH_3$, $CH_2$—O—$CH_2$—NH—$CH_3$, $CH_2$—N($CH_3$)—$CH_2$—O—$CH_3$, $CH_2$—O—$CH_2$—N($CH_3$)—$CH_3$, —CH=CH—N($CH_3$)—$CH_3$, =CH—N($CH_3$)—$CH_3$, =CH—N($CH_3$)—$CH_2$—$CH_3$, =CH—$CH_2$—N($CH_3$)—$CH_2$—$CH_3$, =CH—$CH_2$—N($CH_3$)—$CH_3$, —$CH_2$—$CH_2$=N($CH_3$) and —$CH_2$=N($CH_3$).

For the purposes of this invention the expression "cycloalkyl" or "$C_{3-10}$ cycloalkyl" denotes cyclic aliphatic hydrocarbons having 3, 4, 5, 6, 7, 8, 9 or 10 carbon atoms, wherein the hydrocarbons can be saturated or unsaturated (but not aromatic), unsubstituted or mono- or polysubstituted. The binding of the cycloalkyl to the higher-order general structure can be made via any desired and possible ring member of the cycloalkyl radical. The cycloalkyl radicals can also be fused to further saturated, (partially) unsaturated, (hetero) cyclic, aromatic or heteroaromatic ring systems, i.e. to cycloalkyl, heterocyclyl, aryl or heteroaryl, which can in turn be unsubstituted or mono- or polysubstituted. The cycloalkyl radicals can further be singly or multiply bridged, as for example in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclohexyl, cycloheptyl, cyclooctyl, cyclononyl,

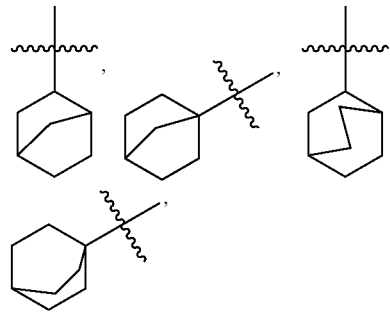

cyclodecyl, adamantyl, cyclopentenyl, cyclohexenyl, cycloheptenyl and cyclooctenyl.

The term "heterocyclyl" or "heterocycloalkyl" includes aliphatic saturated or unsaturated (but not aromatic) cycloalkyls having three to ten, i.e. 3, 4, 5, 6, 7, 8, 9 or 10 ring members, in which at least one, optionally also two or three, carbon atoms are replaced by a heteroatom or a heteroatom group selected independently of one another from the group consisting of O, S, N, NH and N($C_{1-8}$ alkyl), preferably N($CH_3$), wherein the ring members can be unsubstituted or mono- or polysubstituted. The binding of the heterocyclyl to the higher-order general structure can be made via any desired and possible ring member of the heterocyclyl radical. The heterocyclyl radicals can also be fused to further saturated, (partially) unsaturated, (hetero)cyclic or aromatic or heteroaromatic ring systems, i.e. to cycloalkyl, heterocyclyl, aryl or heteroaryl, which can in turn be unsubstituted or mono- or polysubstituted. Preferred are heterocyclyl radicals from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the meaning of this invention, the term "aryl" denotes aromatic hydrocarbons having up to 14 ring members, inter alia phenyls and naphthyls. Each aryl radical can be present in unsubstituted or mono- or polysubstituted form, wherein the aryl substituents can be identical or different and can be at any desired and possible position of the aryl. The binding of the aryl to the higher-order general structure can be made via any desired and possible ring member of the aryl radical. The aryl radicals can also be fused to further saturated, (partially) unsaturated, (hetero)cyclic, aromatic or heteroaromatic ring systems, i.e. to cycloalkyl, heterocyclyl, aryl or heteroaryl, which can in turn be unsubstituted or mono- or polysubstituted. Examples of fused aryl radicals are benzodioxolanyl and benzodioxanyl. Aryl is preferably selected from the group including phenyl, 1-naphthyl and 2-naphthyl, each of which can be unsubstituted or mono- or polysubstituted. A particularly preferred aryl is phenyl, unsubstituted or mono- or polysubstituted.

The term "heteroaryl" stands for a 5- or 6-membered cyclic aromatic radical containing at least 1, optionally also 2, 3, 4 or 5 heteroatoms, wherein the heteroatoms can each be selected independently of one another from the group S, N and O and the heteroaryl radical can be unsubstituted or mono- or polysubstituted; if the heteroaryl is substituted, the substituents can be identical or different and can be at any desired and possible position of the heteroaryl. The binding to the higher-order general structure can be made via any desired and possible ring member of the heteroaryl radical. The heteroaryl can also be part of a bicyclic or polycyclic system having up to 14 ring members, wherein the ring system can be formed with further saturated, (partially) unsaturated, (hetero)cyclic or aromatic or heteroaromatic rings, i.e. with cycloalkyl, heterocyclyl, aryl or heteroaryl, which can in turn be unsubstituted or mono- or polysubstituted. The heteroaryl radical is preferably selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl(thiophenyl), triazolyl, tetrazolyl, thiazolyl, thiadiazolyl or triazinyl. Furyl, pyridyl and thienyl are particularly preferred.

Within the meaning of the invention the expressions "$C_{1-4}$ alkyl- or $C_{1-8}$ alkyl-bridged aryl, heteroaryl, heterocyclyl or cycloalkyl" mean that $C_{1-4}$ alkyl or $C_{1-8}$ alkyl and aryl or heteroaryl or heterocyclyl or cycloalkyl have the meanings defined above and the aryl or heteroaryl or heterocyclyl or cycloalkyl radical is bound by a $C_{1-4}$ alkyl or a $C_{1-8}$ alkyl group to the higher-order general structure. The alkyl chain can in all cases be saturated or unsaturated, branched or unbranched, unsubstituted or mono- or polysubstituted. $C_{1-4}$ alkyl or $C_{1-8}$ alkyl are preferably selected from the group comprising —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_3$)—CH$_2$—, —C(CH$_3$)$_2$—CH$_2$—CH$_2$—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$—, —CH$_2$—(CH$_2$)$_4$—CH$_2$—, —CH═CH—, —CH═CH—CH$_2$—, —C(CH$_3$)═CH$_2$—, —CH═CH—CH$_2$—CH$_2$—, —CH$_2$—CH═CH—CH$_2$—, —CH═CH—CH═CH—, —C(CH$_3$)═CH—CH$_2$—, —CH═C(CH$_3$)—CH$_2$—, —C(CH$_3$)═C(CH$_3$)—, —C(CH$_2$CH$_3$)═CH—, —CH═CH—CH$_2$—CH$_2$—CH$_2$—, —CH$_2$—CH═CH—CH$_2$—CH$_2$—, —CH═CH—CH═CH—CH$_2$—, —CH═CH—CH$_2$—CH═CH—, —CH═CH—CH$_2$—CH$_2$—CH═CH$_2$—, —C≡C—, —C≡C—CH$_2$—, —C≡C—CH$_2$—CH$_3$—, —CH$_2$—C≡C—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

Within the meaning of the invention the expressions "$C_{2-8}$ heteroalkyl-bridged aryl, heteroaryl, heterocyclyl or cycloalkyl" mean that $C_{2-8}$ heteroalkyl and aryl or heteroaryl or heterocyclyl or cycloalkyl have the meanings defined above and the aryl or heteroaryl or heterocyclyl or cycloalkyl radical is bound by a $C_{2-8}$ heteroalkyl group to the higher-order general structure. The heteroalkyl chain can in all cases be saturated or unsaturated, branched or unbranched, unsubstituted or mono- or polysubstituted. If a terminal carbon atom of the $C_{2-8}$ heteroalkyl group is replaced by a heteroatom or a heteroatom group, the binding of a heteroaryl or a heterocyclyl to the heteroatom or the heteroatom group of the $C_{2-8}$ heteroalkyl is always made via a carbon atom of the heteroaryl or heterocyclyl. The terminal carbon atom is understood to mean the carbon atom within the $C_{2-8}$ heteroalkyl which within the chain is the furthest away from the general higher-order structure. If the terminal carbon atom of a $C_{2-8}$ heteroalkyl is replaced by an N(CH$_3$) group, for example, this is the furthest away from the general higher-order structure within the $C_{2-8}$ heteroalkyl and bound to the aryl or heteroaryl or heterocyclyl or cycloalkyl radical. $C_{2-8}$ heteroalkyl is preferably selected from the group comprising —CH$_2$—NH—, —CH$_2$—N(CH$_3$)—, —CH$_2$—O—, —CH$_2$—CH$_2$—NH—, —CH$_2$—CH$_2$—N(CH$_3$)—, —CH$_2$—CH$_2$—O—, —CH$_2$—CH$_2$—CH$_2$—NH—, —CH$_2$—CH$_2$—CH$_2$—N(CH$_3$)—, —CH$_2$—CH$_2$—CH$_2$—O—, —CH$_2$—O—CH$_2$—, —CH$_2$—CH$_2$—O—CH$_2$—, —CH$_2$—CH$_2$—O—CH$_2$—CH$_2$—, —CH$_2$—CH$_2$—O—CH$_2$—CH$_2$—O—CH$_2$—, —CH═CH—O—CH$_2$—, —CH═CH—O—CH$_2$—CH$_2$—, ═CH—O—CH$_2$—, ═CH—O—CH$_2$—CH$_2$—, ═CH—CH$_2$—O—CH$_2$—CH$_2$—, ═CH—CH$_2$—O—CH$_2$—, —CH$_2$—NH—CH$_2$—, —CH$_2$—CH$_2$—NH—CH$_2$—, —CH$_2$—CH$_2$—NH—CH$_2$—CH$_2$—, —CH$_2$—CH$_2$—NH—CH$_2$—CH$_2$—NH—CH$_2$—, —CH═CH—NH—CH$_2$—, —CH═CH—NH—CH$_2$—CH$_2$—, —CH═CH—N(CH$_3$)—CH$_2$—CH$_2$—, ═CH—NH—CH$_2$—, ═CH—NH—CH$_2$—CH$_2$—, ═CH—CH$_2$—NH—CH$_2$—CH$_2$—, ═CH—CH$_2$—NH—CH$_2$—, —CH$_2$—N(CH$_3$)—CH$_2$—, —CH$_2$—CH$_2$—N(CH$_3$)—CH$_2$—, —CH$_2$—CH$_2$—N(CH$_3$)—CH$_2$—CH$_2$—, —CH$_2$—CH$_2$—N(CH$_3$)—CH$_2$—CH$_2$—N(CH$_3$)—CH$_2$—CH$_2$—N(CH$_3$)—CH$_2$—, —CH$_2$—CH$_2$—NH—CH$_2$—CH$_2$—O—CH$_2$—, —CH$_2$—CH$_2$—O—CH$_2$—CH$_2$—NH—CH$_2$—, —CH$_2$—CH$_2$—N(CH$_3$)—CH$_2$—CH$_2$—O—CH$_2$—, —CH$_2$—CH$_2$—O—CH$_2$—CH$_2$—N(CH$_3$)—CH$_2$—, —CH$_2$—NH—CH$_2$—O—CH$_2$—, —CH$_2$—O—CH$_2$—NH—CH$_2$—, —CH$_2$—N(CH$_3$)—CH$_2$—O—CH$_2$—, —CH$_2$—O—CH$_2$—N(CH$_3$)—CH$_2$—, —CH═CH—N(CH$_3$)—CH$_2$—, ═CH—N(CH$_3$)—CH$_2$—, ═CH—N(CH$_3$)—CH$_2$—CH$_2$—, ═CH—CH$_2$—N(CH$_3$)—CH$_2$—CH$_2$—, ═CH—CH$_2$—N(CH$_3$)—CH$_2$—, —CH$_2$—S—, —CH$_2$—CH$_2$—S—, —CH$_2$—CH$_2$—CH$_2$—S—, —CH$_2$—CH$_2$—CH$_2$—CH$_2$—S—, —CH$_2$—S(═O)$_2$—, —CH$_2$—CH$_2$—S(═O)$_2$—, —CH$_2$—CH$_2$—CH$_2$—S(═O)$_2$— and —CH$_2$—CH$_2$—CH$_2$—CH$_2$—S(═O)$_2$—.

In connection with "alkyl", "heteroalkyl", "heterocyclyl" and "cycloalkyl" the term "mono- or polysubstituted" within the meaning of this invention is understood to mean the single or multiple, e.g. two, three or four times, substitution of one or more hydrogen atoms, each independently of one another, with substituents selected from the group comprising F; Cl; Br; I; CN; CF$_3$; ═O; ═NH; ═C(NH$_2$)$_2$; NO$_2$; R$^0$; C(═O)H; C(═O)R$^0$; CO$_2$H; C(═O)OR$^0$; CONH$_2$; C(═O)NHR$^0$; C(═O)N(R$^0$)$_2$; OH; OR$^0$; —O—(C$_{1-8}$ alkyl)-O—; O—C(═O)—R$^0$; O—C(═O)—O—R$^0$; O—(C═O)—NH—R$^0$;

O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SR⁰; S(=O)R⁰; S(=O)₂R⁰; S(=O)₂OH; S(=O)₂OR⁰; S(=O)₂NH₂; S(=O)₂NHR⁰; S(=O)₂N(R⁰)₂, wherein polysubstituted radicals are understood to be radicals which are substituted multiple times, for example twice, three or four times, at different or the same atoms, for example substituted three times at the same C atom, as in the case of CF₃ or CH₂CF₃, or at different points, as in the case of CH(OH)—CH=CH—CHCl₂. A substituent can in turn itself optionally be mono- or polysubstituted. The polysubstitution can be performed with identical or different substituents.

Preferred "alkyl", "heteroalkyl", "heterocyclyl" and "cycloalkyl" substituents are selected from the group comprising F; Cl; Br; I; NO₂; CF₃; CN; =O; =NH; R⁰; C(=O)(R⁰ or H); C(=O)O(R⁰ or H); C(=O)N(R⁰ or H)₂; OH; OR⁰; O—C(=O)—R⁰; O—(C₁₋₈ alkyl)-OH; O—(C₁₋₈ alkyl)-O—C₁₋₈ alkyl; OCF₃; N(R⁰ or H)₂; N(R⁰ or H)—C(=O)—R⁰; N(R⁰ or H)—C(=O)—N(R⁰ or H)₂; SH; SCF₃; SR⁰; S(=O)₂R⁰; S(=O)₂O(R⁰ or H) and S(=O)₂—N(R⁰ or H)₂.

Particularly preferred "alkyl", "heteroalkyl", "heterocyclyl" and "cycloalkyl" substituents are selected from the group consisting of F; Cl; Br; I; NO₂; CF₃; CN; =O; C₁₋₈ alkyl; C₂₋₈ heteroalkyl; aryl; heteroaryl; C₃₋₁₀ cycloalkyl; heterocyclyl; C₁₋₈ alkyl- or C₂₋₈ heteroalkyl-bridged aryl, heteroaryl, C₃₋₁₀ cycloalkyl or heterocyclyl; CHO; C(=O)C₁₋₈ alkyl; C(=O) aryl; C(=O) heteroaryl; CO₂H; C(=O)O—C₁₋₈ alkyl; C(=O)O— aryl; C(=O)O-heteroaryl; CONH₂; C(=O)NH—C₁₋₈ alkyl; C(=O)N(C₁₋₈ alkyl)₂; C(=O)NH-aryl; C(=O)N(aryl)₂; C(=O)NH-heteroaryl; C(=O)N(heteroaryl)₂; C(=O)N(C₁₋₈ alkyl)(aryl); C(=O)N(C₁₋₈ alkyl)(heteroaryl); C(=O)N(heteroaryl)(aryl); OH; O—C₁₋₈ alkyl; OCF₃; O—(C₁₋₈ alkyl)-OH; O—(C₁₋₈ alkyl)-O—C₁₋₈ alkyl; O-benzyl; O-aryl; O-heteroaryl; O—C(=O)C₁₋₈ alkyl; O—C(=O) aryl; O—C(=O) heteroaryl; NH₂; NH—C₁₋₈ alkyl; N(C₁₋₈ alkyl)₂; NH—C(=O)C₁₋₈ alkyl; N(C₁₋₈ alkyl)-C(=O)C₁₋₈ alkyl; N(C(=O)C₁₋₈ alkyl)₂; NH—C(=O)-aryl; NH—C(=O)-heteroaryl; SH; S—C₁₋₈ alkyl; SCF₃; S-benzyl; S-aryl; S-heteroaryl; S(=O)₂C₁₋₈ alkyl; S(=O)₂ aryl; S(=O)₂ heteroaryl; S(=O)₂OH; S(=O)₂O—C₁₋₈ alkyl; S(=O)₂O-aryl; S(=O)₂O-heteroaryl; S(=O)₂—NH—C₁₋₈ alkyl; S(=O)₂—NH-aryl; and S(=O)₂—NH—C₁₋₈ heteroaryl.

In connection with "aryl" and "heteroaryl" the expression "mono- or polysubstituted" within the meaning of this invention is understood to mean the single or multiple, e.g. two, three or four times, substitution of one or more hydrogen atoms in the ring system, each independently of one another, with substituents selected from the group comprising F; Cl; Br; I; NO₂; CF₃; CN; R⁰; C(=O)H; C(=O)R⁰; CO₂H; C(=O)OR⁰; CONH₂; C(=O)NHR⁰; C(=O)N(R⁰)₂; OH; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SR⁰; S(=O)R⁰; S(=O)₂R⁰; S(=O)₂OH; S(=O)₂OR⁰; S(=O)₂NH₂; S(=O)₂NHR⁰; S(=O)₂N(R⁰)₂, at one or optionally different atoms, wherein a substituent can in turn itself optionally be mono- or polysubstituted. The polysubstitution is performed with identical or with different substituents.

Preferred "aryl" and "heteroaryl" substituents are F; Cl; Br; I; NO₂; CF₃; CN; R⁰; C(=O)(R⁰ or H); C(=O)O(R⁰ or H); C(=O)N(R⁰ or H)₂; OH; OR⁰; O—C(=O)—R⁰; O—(C₁₋₈ alkyl)-O—C₁₋₈ alkyl; OCF₃; N(R⁰ or H)₂; N(R⁰ or H)—C(=O)—R⁰; N(R⁰ or H)—C(=O)—N(R⁰ or H)₂; SH; SCF₃; SR⁰; S(=O)₂R⁰; S(=O)₂O(R⁰ or H); S(=O)₂—N(R⁰ or H)₂.

Particularly preferred "aryl" and "heteroaryl" substituents are selected from the group consisting of F; Cl; Br; I; NO₂; CF₃; CN; C₁₋₈ alkyl; or C₂₋₈ heteroalkyl; aryl; heteroaryl; C₃₋₁₀ cycloalkyl; heterocyclyl; C₁₋₈ alkyl- or C₂₋₈ heteroalkyl-bridged aryl, heteroaryl, C₃₋₁₀ cycloalkyl or heterocyclyl; CHO; C(=O)C₁₋₈ alkyl; C(=O) aryl; C(=O) heteroaryl; CO₂H; C(=O)O—C₁₋₈ alkyl; C(=O)O-aryl; C(=O)O-heteroaryl; CONH₂; C(=O)NH—C₁₋₈ alkyl; C(=O)N(C₁₋₈ alkyl)₂; C(=O)NH-aryl; C(=O)N(aryl)₂; C(=O)NH-heteroaryl; C(=O)N(heteroaryl)₂; C(=O)N(C₁₋₈ alkyl)(aryl); C(=O)N(C₁₋₈ alkyl)(heteroaryl); C(=O)N(heteroaryl)(aryl); OH; O—C₁₋₈ alkyl; OCF₃; 0-(C₁₋₈ alkyl)-OH; O—(C₁₋₈ alkyl)-O—C₁₋₈ alkyl; O-benzyl; O-aryl; O-heteroaryl; O—C(=O)C₁₋₈ alkyl; O—C(=O) aryl; O—C(=O)heteroaryl; NH₂, NH—C₁₋₈ alkyl; N(C₁₋₈ alkyl)₂; NH—C(=O)C₁₋₈ alkyl; N(C₁₋₈ alkyl)-C(=O)C₁₋₈ alkyl; N(C(=O)C₁₋₈ alkyl)₂; NH—C(=O)-aryl; NH—C(=O)-heteroaryl; SH; S—C₁₋₈ alkyl; SCF₃; S-benzyl; S-aryl; S-heteroaryl; S(=O)₂C₁₋₈ alkyl; S(=O)₂ aryl; S(=O)₂ heteroaryl; S(=O)₂OH; S(=O)₂O—C₁₋₈ alkyl; S(=O)₂O-aryl; S(=O)₂O-heteroaryl; S(=O)₂—NH—C₁₋₈ alkyl; S(=O)₂—NH-aryl; S(=O)₂—NH—C₁₋₈ heteroaryl.

The compounds according to the invention are defined by substituents, for example by R¹, R² and R³ (1ˢᵗ generation substituents), which are in turn optionally substituted (2ⁿᵈ generation substituents). Depending on the definition, these substituents of the substituents can themselves be substituted again (3ʳᵈ generation substituents). For example, if R³=R⁰ where R⁰=aryl (1ˢᵗ generation substituent), then aryl can itself be substituted, e.g. with NHR⁰, where R⁰=C₁₋₁₀ alkyl (2ⁿᵈ generation substituent). This gives the functional group aryl-NHC₁₋₁₀ alkyl. C₁₋₁₀ alkyl can then itself be substituted again, for example with Cl (3ʳᵈ generation substituent). This then gives in total the functional group aryl-NHC₁₋₁₀ alkyl-Cl.

In a preferred embodiment the 3ʳᵈ generation substituents cannot, however, be substituted again, i.e. there are then no 4ᵗʰ generation substituents.

In another preferred embodiment the 2ⁿᵈ generation substituents cannot be substituted again, i.e. there are then no 3ʳᵈ generation substituents either. In other words, in this embodiment for example in the case of the general formula (1) the functional groups for R⁰ to R⁷ can each optionally be substituted, but the various substituents cannot then themselves be substituted again.

If a radical occurs more than once within a molecule, such as the radical R⁰ for example, then this radical can have different meanings for different substituents: for example, if both $R^1=R^0$ and $R^2=R^0$, then $R^0$ can stand for $R^1$=aryl and $R^0$ can stand for $R^2=C_{1-10}$ alkyl.

In some cases the compounds according to the invention are defined by substituents which are or which carry an aryl or heteroaryl radical, each unsubstituted or mono- or polysubstituted, or which together with the carbon atom(s) or heteroatom(s) binding them as ring member or ring members form a ring, for example an aryl or heteroaryl, each unsubstituted or mono- or polysubstituted. Both these aryl or heteroaryl radicals and the aromatic ring systems formed in this way can optionally be fused to $C_{3-10}$ cycloalkyl or heterocyclyl, each saturated or unsaturated, i.e. to a $C_{3-10}$ cycloalkyl such as cyclopentyl or to a heterocyclyl such as morpholinyl, wherein the $C_{3-10}$ cycloalkyl or heterocyclyl radicals fused in this way can themselves be unsubstituted or mono- or polysubstituted.

In some cases the compounds according to the invention are defined by substituents which are or which carry a $C_{3-10}$ cycloalkyl or heterocyclyl radical, each unsubstituted or mono- or polysubstituted, or which together with the carbon atom(s) or heteroatom(s) binding them as ring member or ring members form a ring, for example a $C_{3-10}$ cycloalkyl or heterocyclyl, each unsubstituted or mono- or polysubstituted. Both these $C_{3-10}$ cycloalkyl or heterocyclyl radicals and the aliphatic ring systems formed can optionally be fused to aryl or heteroaryl, i.e. to an aryl such as phenyl or to a heteroaryl such as pyridyl, wherein the aryl or heteroaryl radicals fused in this way can themselves be unsubstituted or mono- or polysubstituted.

In some cases the compounds according to the invention are defined by radicals within which two substituents are referred to by the general expression "("substituent 1" or "substituent 2" or "substituent 3")". This expression means that "substituent 1" and "substituent 2" and "substituent 3" within such a radical can occur in any possible combination. Thus for example the expression "($R^0$ or H)" within a radical means that $R^0$ and H can occur within this radical in any possible combination. Thus the radical "$N(R^0$ or $H)_2$" can stand for "$NH_2$", "$NHR^0$" and)"$N(R^0)_2$", for example. If $R^0$ occurs more than once within a radical, as in the case of)"$N(R^0)_2$", then $R^0$ can have the same or different meanings in each case: in the present example of)"$N(R^0)_2$", for example, $R^0$ can stand twice for aryl, giving the functional group "$N(aryl)_2$", or $R^0$ can stand once for aryl and once for $C_{1-10}$ alkyl, giving the functional group "$N(aryl)(C_{1-10}$ alkyl)".

In the context of the present invention, the symbol

used in formulae represents a linking of a corresponding radical to the higher-order general structure.

Within the meaning of this invention the term "salt formed with a physiologically compatible acid" is understood to mean salts of the individual active ingredient with inorganic or organic acids which are physiologically—particularly when used in humans and/or mammals—compatible. Hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Citric acid and hydrochloric acid are particularly preferred.

Physiologically compatible salts with cations or bases are salts of the individual compound as anion with at least one, preferably inorganic, cation, which are physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

In a preferred embodiment of the compounds according to the invention the substituents $R^1$, $R^2$, $R^3$ and $R^4$ are each selected independently of one another from the group consisting of H; F; Cl; Br; I; $NO_2$; $CF_3$; CN; $R^0$; C(=O)($R^0$ or H); C(=O)O($R^0$ or H); C(=O)N($R^0$ or $H)_2$; OH; $OR^0$; O—($C_{1-8}$ alkyl)-OH; O—($C_{1-8}$ alkyl)-O—$C_{1-8}$ alkyl; $OCF_3$; O—C(=O)—$R^0$; N($R^0$ or $H)_2$; N($R^0$ or H)—C(=O)—$R^0$; N($R^0$ or H)—C(=O)—N($R^0$ or $H)_2$; SH; $SCF_3$; $SR^0$; S(=O)$_2R^0$; S(=O)$_2$O($R^0$ or H) and S(=O)$_2$—N($R^0$ or $H)_2$.

The substituents $R^1$, $R^2$, $R^3$ and $R^4$ are preferably each selected independently of one another from the group consisting of H; F; Cl; Br; I; $NO_2$; $CF_3$; CN; C(=O)H; C(=O)—OH; C(=O)$NH_2$; $C_{1-8}$ alkyl, O—$C_{1-8}$ alkyl, C(=O)$C_{1-8}$ alkyl, C(=O)O—$C_{1-8}$ alkyl, O—C(=O)—$C_{1-8}$ alkyl, C(=O)NH—$C_{1-8}$ alkyl, C(=O)N($C_{1-8}$ alkyl)$_2$, NH—$C_{1-8}$ alkyl, N($C_{1-8}$ alkyl)$_2$, NH—C(=O)$C_{1-8}$ alkyl, N($C_{1-8}$ alkyl)-C(=O)$C_{1-8}$ alkyl, S—$C_{1-8}$ alkyl, S(=O)$_2C_{1-8}$ alkyl, S(=O)$_2$O—$C_{1-8}$ alkyl, each saturated or unsaturated, branched or unbranched, unsubstituted or mono- or polysubstituted with one or more substituents selected independently of one another from the group consisting of F, Cl, Br, I, O-methyl and OH; OH; $OCF_3$; SH; $SCF_3$; S(=O)$_2$OH; $NH_2$; $C_{3-10}$ cycloalkyl or heterocyclyl, each saturated or unsaturated, unsubstituted; benzyl, phenyl, pyridyl or thienyl, each unsubstituted or mono-, di- or trisubstituted with one, two or three substituents selected independently of one another from the group consisting of F, Cl, Br, I, $NO_2$, $NH_2$, CN, $C_{1-8}$ alkyl, O—$C_{1-8}$ alkyl, $CF_3$, OH, $OCF_3$, C(=O)—OH, $SCF_3$ and S(=O)$_2$OH.

The substituents $R^1$, $R^2$, $R^3$ and $R^4$ are particularly preferably each selected independently of one another from the group consisting of H; F; Cl; Br; I; $NO_2$; $CF_3$; CN; $CH_2CF_3$; C(=O)—OH; C(=O)$NH_2$; SH; $SCF_3$; S(=O)$_2$OH; $NH_2$; $OCF_3$; OH; $C_{1-8}$ alkyl, O—$C_{1-8}$ alkyl, NH—$C_{1-8}$ alkyl, N($C_{1-8}$ alkyl)$_2$, each saturated, branched or unbranched, unsubstituted or mono-, di- or trisubstituted with one, two or three substituents selected independently of one another from the group consisting of O-methyl and OH; C(=O)$C_{1-8}$ alkyl, C(=O)O—$C_{1-8}$ alkyl, O—C(=O)—$C_{1-8}$ alkyl, C(=O) NH—$C_{1-8}$ alkyl, C(=O)N($C_{1-8}$ alkyl)$_2$, NH—C(=O)$C_{1-8}$ alkyl, N($C_{1-8}$ alkyl)-C(=O)$C_{1-8}$ alkyl, N(C(=O)$C_{1-8}$ alkyl)$_2$, S—$C_{1-8}$ alkyl, S(=O)$_2$O—$C_{1-8}$ alkyl, each saturated, branched or unbranched, unsubstituted; $C_{3-10}$ cycloalkyl, saturated, unsubstituted; pyrrolidinyl, piperidinyl, 4-methylpiperazinyl, piperazinyl or morpholinyl, each unsubstituted; benzyl, phenyl or pyridyl, each unsubstituted or mono-, di- or trisubstituted with one, two or three substituents selected independently of one another from the group consisting of F, Cl, Br, I, CN, $C_{1-8}$ alkyl, O—$C_{1-8}$ alkyl, $CF_3$, OH and $OCF_3$.

The substituents $R^1$, $R^2$, $R^3$ and $R^4$ are most particularly preferably each selected independently of one another from the group consisting of H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; C(=O)-methyl; C(=O)-ethyl;

C(=O)—OH; C(=O)—O-methyl; C(=O)—O-ethyl; C(=O)—NH$_2$; C(=O)—N(methyl)$_2$; C(=O)—N(ethyl)$_2$; C(=O)—NH-methyl; C(=O)—NH-ethyl; C(=O)—N(methyl)(ethyl); OH; O-methyl; O-ethyl; O—(CH$_2$)$_2$—O—CH$_3$; O—(CH$_2$)$_2$—OH; OCF$_3$; O—C(=O)-methyl; O—C(=O)-ethyl; NR$^a$R$^b$, wherein R$^a$ and R$^b$ are selected independently of each other from the group consisting of H, methyl, ethyl, (CH$_2$)$_2$—O—CH$_3$ and (CH$_2$)$_2$—OH or R$^a$ and R$^b$ together with the nitrogen atom linking them form a pyrrolidinyl, piperidinyl, 4-methylpiperazinyl or morpholinyl; NHC(=O)-methyl; NHC(=O)-ethyl; SH; SCF$_3$; S-methyl; S-ethyl; S(=O)$_2$OH; S(=O)$_2$O-methyl; benzyl, phenyl, pyridyl, each unsubstituted or mono-, di- or trisubstituted with one, two or three substituents selected independently of one another from the group consisting of F, Cl, Br, I, CN, methyl, ethyl, CF$_3$, OH, O-methyl and OCF$_3$.

In particular the substituents R$^1$, R$^2$, R$^3$ and R$^4$ are each selected independently of one another from the group consisting of H; F; Cl; Br; I; NO$_2$; CF$_3$; CN; methyl; ethyl; C(=O)-methyl; O-methyl; O—(CH$_2$)$_2$—O—CH$_3$; OCF$_3$; O—C(=O)-methyl; NH—C(=O)-methyl; N(methyl)$_2$; morpholinyl; S-methyl; SCF$_3$; benzyl and phenyl, each unsubstituted.

In a most particularly preferred embodiment of the invention R$^1$, R$^2$, R$^3$ and R$^4$ are each selected independently of one another from the group consisting of H, F, Cl, CF$_3$ and OCF$_3$.

In a further preferred embodiment of the compounds according to the invention the substituent R$^5$ is selected from the group consisting of H; F; Cl; Br; I; NO$_2$; CF$_3$; CN; R$^0$; C(=O)(R$^0$ or H); C(=O)O(R$^0$ or H); C(=O)N(R$^0$ or H)$_2$; N(R$^0$ or H)$_2$; N(R$^0$ or H)—C(=O)—R$^0$; N(R$^0$ or H)—C(=O)—N(R$^0$ or H)$_2$; SH; SCF$_3$; SR$^0$; S(=O)$_2$R$^0$; S(=O)$_2$O(R$^0$ or H); S(=O)$_2$—N(R$^0$ or H)$_2$.

In another preferred embodiment of the compounds according to the invention the substituent R$^5$ is selected from the group consisting of H; F; Cl; Br; I; NO$_2$; CF$_3$; CN; R$^0$; C(=O)(R$^0$ or H); C(=O)O(R$^0$ or H); C(=O)N(R$^0$ or H)$_2$; OR$^0$; —O—(C$_{1-8}$ alkyl)-OH; O—(C$_{1-8}$ alkyl)-O—C$_{1-8}$ alkyl; OCF$_3$; O—C(=O)—R$^0$; N(R$^0$ or H)$_2$; N(R$^0$ or H)—C(=O)—R$^0$; N(R$^0$ or H)—C(=O)—N(R$^0$ or H)$_2$; SH; SCF$_3$; SR$^0$; S(=O)$_2$R$^0$; S(=O)$_2$O(R$^0$ or H); S(=O)$_2$—N(R$^0$ or H)$_2$.

The substituent R$^5$ is preferably selected from the group consisting of H; F; Cl; Br; I; NO$_2$; CF$_3$; CN; C(=O)H; C(=O)—OH; C(=O)—NH$_2$; C$_{1-8}$ alkyl, O—C$_{1-8}$ alkyl, C(=O)C$_{1-8}$ alkyl, C(=O)O—C$_{1-8}$ alkyl, O—C(=O)—C$_{1-8}$ alkyl, C(=O)NH—C$_{1-8}$ alkyl, C(=O)N(C$_{1-8}$ alkyl)$_2$, NH—C$_{1-8}$ alkyl, N(C$_{1-8}$ alkyl)$_2$, NH—C(=O)C$_{1-8}$ alkyl, N(C$_{1-8}$ alkyl)-C(=O)C$_{1-8}$ alkyl, S—C$_{1-8}$ alkyl, S(=O)$_2$C$_{1-8}$ alkyl, S(=O)$_2$O—C$_{1-8}$ alkyl, each saturated or unsaturated, branched or unbranched, unsubstituted or mono- or polysubstituted with one or more substituents selected independently of one another from the group consisting of F, Cl, Br, I, O-methyl and OH; OCF$_3$; SH; SCF$_3$; S(=O)$_2$OH; NH$_2$; C$_{3-10}$ cycloalkyl or heterocyclyl, each saturated or unsaturated, unsubstituted; benzyl, phenyl, pyridyl or thienyl, each unsubstituted or mono-, di- or trisubstituted with one, two or three substituents selected independently of one another from the group consisting of F, Cl, Br, I, NO$_2$, NH$_2$, CN, C$_{1-8}$ alkyl, O—C$_{1-8}$ alkyl, CF$_3$, OH, OCF$_3$, C(=O)—OH, SCF$_3$ and S(=O)$_2$OH.

The substituent R$^5$ is particularly preferably selected from the group consisting of H; F; Cl; Br; I; NO$_2$; CF$_3$; CN; CH$_2$CF$_3$; C(=O)—OH; C(=O)—NH$_2$; SH; SCF$_3$; S(=O)$_2$OH; NH$_2$; OCF$_3$; C$_{1-8}$ alkyl, O—C$_{1-8}$ alkyl, NH—C$_{1-8}$ alkyl, N(C$_{1-8}$ alkyl)$_2$, each saturated, branched or unbranched, unsubstituted or mono-, di- or trisubstituted with one or more substituents selected independently of one another from the group consisting of O-methyl and OH; C(=O)C$_{1-8}$ alkyl, C(=O)O—C$_{1-8}$ alkyl, O—C(=O)—C$_{1-8}$ alkyl, C(=O)NH—C$_{1-8}$ alkyl, C(=O)N(C$_{1-8}$ alkyl)$_2$, NH—C(=O)C$_{1-8}$ alkyl, N(C$_{1-8}$ alkyl)-C(=O)C$_{1-8}$ alkyl, N(C(=O)C$_{1-8}$ alkyl)$_2$, S—C$_{1-8}$ alkyl, S(=O)$_2$O—C$_{1-8}$ alkyl, each saturated, branched or unbranched, unsubstituted; C$_{3-10}$ cycloalkyl, saturated, unsubstituted; pyrrolidinyl, piperidinyl, 4-methylpiperazinyl, piperazinyl or morpholinyl, each unsubstituted; benzyl, phenyl or pyridyl, each unsubstituted or mono-, di- or trisubstituted with one, two or three substituents selected independently of one another from the group consisting of F, Cl, Br, I, CN, C$_{1-8}$ alkyl, O—C$_{1-8}$ alkyl, CF$_3$, OH and OCF$_3$.

The substituent R$^5$ is most particularly preferably selected from the group consisting of H; F; Cl; Br; I; NO$_2$; CF$_3$; CN; methyl; ethyl; n-propyl; isopropyl; cyclopropyl; n-butyl; sec-butyl; tert-butyl; CH$_2$CF$_3$; C(=O)-methyl; C(=O)-ethyl; C(=O)—OH; C(=O)—O-methyl; C(=O)—O-ethyl; C(=O)—NH$_2$; C(=O)—N(methyl)$_2$; C(=O)—N(ethyl)$_2$; C(=O)—NH-methyl; C(=O)—NH-ethyl; C(=O)—N(methyl)(ethyl); O-methyl; O-ethyl; O—(CH$_2$)$_2$—O—CH$_3$; O—(CH$_2$)$_2$—OH; OCF$_3$; O—C(=O)-methyl; O—C(=O)-ethyl; NR$^a$R$^b$, wherein R$^a$ and R$^b$ are selected independently of each other from the group consisting of H, methyl, ethyl, (CH$_2$)$_2$—O—CH$_3$, (CH$_2$)$_2$—OH, C(=O)-methyl, C(=O)-ethyl or R$^a$ and R$^b$ together with the nitrogen atom linking them form a pyrrolidinyl, piperidinyl, 4-methylpiperazinyl or morpholinyl; SH; SCF$_3$; S-methyl; S-ethyl; S(=O)$_2$OH; S(=O)$_2$O-methyl; benzyl, unsubstituted or mono-, di- or trisubstituted with one, two or three substituents selected independently of one another from the group consisting of F, Cl, Br, I, CN, methyl, ethyl, CF$_3$, OH, O-methyl and OCF$_3$.

In particular the substituent R$^5$ is selected from the group consisting of H; F; Cl; Br; I; NO$_2$; CF$_3$; CN; methyl; ethyl; —CH$_2$—O-methyl, C(=O)-methyl; O-methyl; O—(CH$_2$)$_2$—O—CH$_3$; OCF$_3$; O—C(=O)-methyl; NH—C(=O)-methyl; N(methyl)$_2$; morpholinyl; S-methyl; SCF$_3$; benzyl, unsubstituted.

In a most particularly preferred embodiment of the invention R$^5$ is methyl, OMe or —CH$_2$O-methyl.

In a further preferred embodiment the substituent R$^6$ stands for

C$_{1-10}$ alkyl or C$_{2-10}$ heteroalkyl, each saturated or unsaturated, branched or unbranched, unsubstituted or mono- or polysubstituted with one or more substituents selected independently of one another from the group consisting of F, Cl, Br, I, NO$_2$, CF$_3$, CN, OH, =O, C(=O)—OH, OCF$_3$, NH$_2$, S(=O)$_2$OH, SH, SCF$_3$, C$_{1-8}$ alkyl, O—C$_{1-8}$ alkyl, S—C$_{1-8}$ alkyl, NH—C$_{1-8}$ alkyl, N(C$_{1-8}$ alkyl)$_2$, C$_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—C$_{1-8}$ alkyl, OH and OCF$_3$, and wherein the aforementioned C$_{3-10}$ cycloalkyl or heterocyclyl can be saturated or unsaturated, unsubstituted or mono- or polysubstituted with one or more substituents selected independently of one another from the group consisting of F, Cl, Br, I, C$_{1-8}$ alkyl, OH, =O, O—C$_{1-8}$ alkyl, OCF$_3$, NH$_2$, NH—C$_{1-8}$ alkyl and N(C$_{1-8}$ alkyl)$_2$;

C$_{3-10}$ cycloalkyl or heterocyclyl or C$_{1-8}$ alkyl- or C$_{2-8}$ heteroalkyl-bridged C$_{3-10}$ cycloalkyl or heterocyclyl, each saturated or unsaturated, unsubstituted or mono- or polysubstituted with one or more substituents selected independently of one another from the group consisting of F, Cl, Br, I, NO$_2$, CN, OH, =O, O—C$_{1-8}$ alkyl, OCF$_3$, C$_{1-8}$ alkyl, C(=O)—

OH, CF$_3$, NH$_2$, NH(C$_{1-8}$ alkyl), N(C$_{1-8}$ alkyl)$_2$, SH, S—C$_{1-8}$ alkyl, SCF$_3$, S(=O)$_2$OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, NO$_2$, CF$_3$, CN, OH, =O, C(=O)—OH, OCF$_3$, NH$_2$, S(=O)$_2$OH, SH, SCF$_3$, C$_{1-8}$ alkyl, O—C$_{1-8}$ alkyl, S—C$_{1-8}$ alkyl, NH—C$_{1-8}$ alkyl, N(C$_{1-8}$ alkyl)$_2$, C$_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—C$_{1-8}$ alkyl, OH and OCF$_3$, and wherein the aforementioned C$_{3-10}$ cycloalkyl or heterocyclyl can be saturated or unsaturated, unsubstituted or mono- or polysubstituted with one or more substituents selected independently of one another from the group consisting of F, Cl, Br, I, C$_{1-8}$ alkyl, OH, =O, O—C$_{1-8}$ alkyl, OCF$_3$, NH$_2$, NH—C$_{1-8}$ alkyl and N(C$_{1-8}$ alkyl)$_2$;

aryl or heteroaryl or C$_{1-8}$ alkyl- or C$_{2-8}$ heteroalkyl-bridged aryl or heteroaryl, each unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$, S(=O)$_2$OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, NO$_2$, CF$_3$, CN, OH, =O, C(=O)—OH, OCF$_3$, NH$_2$, S(=O)$_2$OH, SH, SCF$_3$, C$_{1-8}$ alkyl, O—C$_{1-8}$ alkyl, S—C$_{1-8}$ alkyl, NH—C$_{1-8}$ alkyl, N(C$_{1-8}$ alkyl)$_2$, C$_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—C$_{1-8}$ alkyl, OH and OCF$_3$, and wherein the aforementioned C$_{3-10}$ cycloalkyl or heterocyclyl can be saturated or unsaturated, unsubstituted or mono- or polysubstituted with one or more substituents selected independently of one another from the group consisting of F, Cl, Br, I, C$_{1-8}$ alkyl, OH, =O, O—C$_{1-8}$ alkyl, OCF$_3$, NH$_2$, NH—C$_{1-8}$ alkyl and N(C$_{1-8}$ alkyl)$_2$.

In a further preferred embodiment the substituent R$^6$ stands for the following substructure (T1)

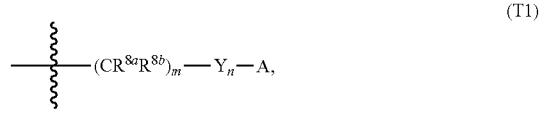

wherein

R$^{8a}$ and R$^{8b}$ stand independently of each other for H; F; Cl; Br; I; NO$_2$; CF$_3$; CN; OH; OCF$_3$; NH$_2$; C$_{1-4}$ alkyl, O—C$_{1-4}$ alkyl, NH—C$_{1-4}$ alkyl, N(C$_{1-4}$ alkyl)$_2$, each saturated or unsaturated, branched or unbranched, unsubstituted or mono- or polysubstituted with one or more substituents selected independently of one another from the group consisting of F, Cl, Br, I, O—C$_{1-4}$ alkyl, OH and OCF$_3$; C$_{3-10}$ cycloalkyl or heterocyclyl, each saturated or unsaturated, unsubstituted or mono- or polysubstituted with one or more substituents selected independently of one another from the group consisting of F, Cl, Br, I, C$_{1-4}$ alkyl, OH, =O, O—C$_{1-4}$ alkyl, OCF$_3$, NH$_2$, NH—C$_{1-4}$ alkyl and N(C$_{1-4}$ alkyl)$_2$;

m stands for 0, 1, 2, 3 or 4;

Y stands for O or NR$^9$, wherein R$^9$ stands for H; C$_{1-4}$ alkyl, saturated or unsaturated, branched or unbranched, unsubstituted or mono- or polysubstituted with one or more substituents selected independently of one another from the group consisting of F, Cl, Br, I, C$_{1-4}$ alkyl, OH, O—C$_{1-4}$ alkyl, OCF$_3$, NH$_2$, NH—C$_{1-4}$ alkyl and N(C$_{1-4}$ alkyl)$_2$; or for C$_{3-10}$ cycloalkyl, saturated or unsaturated, unsubstituted or mono- or polysubstituted with one or more substituents selected independently of one another from the group consisting of F, Cl, Br, I, C$_{1-4}$ alkyl, OH, O—C$_{1-4}$ alkyl, OCF$_3$, NH$_2$, NH—C$_{1-4}$ alkyl and N(C$_{1-4}$ alkyl)$_2$;

n stands for 0 or 1, with the proviso that n does not stand for 1 if m denotes 0;

A stands for C$_{1-8}$ alkyl, saturated or unsaturated, branched or unbranched, unsubstituted or mono- or polysubstituted with one or more substituents selected independently of one another from the group consisting of F, Cl, Br, I, NO$_2$, CN, OH, =O, O—C$_{1-4}$ alkyl, OCF$_3$, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH; C$_{3-10}$ cycloalkyl or heterocyclyl, each saturated or unsaturated, unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$, S(=O)$_2$OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$ and S(=O)$_2$OH; aryl or heteroaryl, each unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$, S(=O)$_2$OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-8}$ alkyl, C(=O)—OH, CF$_3$, NH$_2$, NH(C$_{1-8}$ alkyl), N(C$_{1-8}$ alkyl)$_2$, SH, S—C$_{1-8}$ alkyl, SCF$_3$ and S(=O)$_2$OH.

By preference,

R$^{8a}$ and R$^{8b}$ stand independently of each other for H; F; Cl; Br; I; NO$_2$; CF$_3$; CH$_2$CF$_3$; CN; OH; OCF$_3$, NH$_2$; C$_{1-4}$ alkyl, O—C$_{1-4}$ alkyl, O—C$_{1-4}$ alkyl-OH, O—C$_{1-4}$ alkyl-OCH$_3$, NH—C$_{1-4}$ alkyl, N(C$_{1-4}$ alkyl)$_2$, each saturated or unsaturated, branched or unbranched, unsubstituted; C$_{3-10}$ cycloalkyl, saturated or unsaturated, unsubstituted or mono- or polysubstituted with one or more substituents selected independently of one another from the group consisting of F, Cl, Br, I, C$_{1-4}$ alkyl, OH, O—C$_{1-4}$ alkyl;

m stands for 0, 1, 2, 3 or 4;

Y stands for O or NR$^9$;

wherein R$^9$ stands for H; C$_{1-4}$ alkyl, saturated or unsaturated, unsubstituted; or for C$_{3-10}$ cycloalkyl, saturated or unsaturated, unsubstituted;

n stands for 0 or 1;

with the proviso that n does not stand for 1 if m denotes 0;

A stands for C$_{1-8}$ alkyl, saturated or unsaturated, branched or unbranched, unsubstituted or mono- or polysubstituted with one or more substituents selected independently of one another from the group consisting of F, Cl, Br, I, NO$_2$, CN, OH, O—C$_{1-4}$ alkyl, OCF$_3$, CF$_3$, NH$_2$, NH(C$_{1-4}$ alkyl), N(C$_{1-4}$ alkyl)$_2$, SCF$_3$; C$_{3-10}$ cycloalkyl or heterocyclyl, each saturated or unsaturated, unsubstituted or mono- or polysubstituted with one or more substituents selected independently of one another from the group consisting of F, Cl, Br, I, NO$_2$, CN, OH, O—C$_{1-4}$ alkyl, OCF$_3$, C$_{1-4}$ alkyl, CF$_3$, NH$_2$, NH(C$_{1-4}$ alkyl), N(C$_{1-4\ alkyl})_2$, SCF$_3$; aryl or heteroaryl, each unsubstituted or mono- or polysubstituted with one or more substituents selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$, S(=O)$_2$OH, benzyl, phenyl and pyridyl, wherein benzyl, phenyl or pyridyl are each unsubstituted or mono- or polysubstituted with one or more substituents selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH.

Particularly preferably, R$^{8a}$ and R$^{8b}$ stand independently of each other for H; F; Cl; Br; I; NO$_2$; CF$_3$; CN; methyl; ethyl; n-propyl; isopropyl; cyclopropyl; n-butyl; sec-butyl; tert-butyl; CH$_2$CF$_3$; OH; O-methyl; O-ethyl; O—(CH$_2$)$_2$—O—CH$_3$; O—(CH$_2$)$_2$—OH; OCF$_3$; NH$_2$; NH-methyl; N(methyl)$_2$; NH-ethyl; N(ethyl)$_2$; or N(methyl)(ethyl);

m stands for 1, 2 or 3;

n stands for 0; and

A stands for C$_{1-4}$ alkyl, saturated or unsaturated, branched or unbranched, unsubstituted or mono- or polysubstituted with one or more substituents selected independently of one another from the group consisting of F, Cl, Br, I, OH, O—C$_{1-4}$ alkyl, OCF$_3$ and CF$_3$; C$_{3-10}$ cycloalkyl, saturated, unsubstituted; phenyl, naphthyl, pyridyl, thienyl, each unsubstituted or mono- or di- or trisubstituted with one, two or three substituents selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—Cl$_4$ alkyl, SCF$_3$, S(=O)$_2$OH.

Most particularly preferably, R$^{8a}$ and R$^{8b}$ stand independently of each other for H; F; Cl; Br; I; methyl; ethyl; n-propyl; isopropyl; n-butyl; sec-butyl; tert-butyl; OH; O-methyl; O-ethyl; O—(CH$_2$)$_2$—O—CH$_3$; or O—(CH$_2$)$_2$—OH;

m stands for 1, 2 or 3;

n stands for 0; and

A stands for methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, each unsubstituted or mono-, di- or trisubstituted with one, two or three substituents selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH.

In a particularly preferred embodiment

R$^{8a}$ and R$^{8b}$ stand independently of each other for H, m stands for 1, n for 0 and A for phenyl, pyridyl or thienyl, each substituted 0, 1, 2 or 3 times with a substituent selected from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH.

For n=0 the substructure (T-1) gives rise for R$^6$ to the substructure (T1-1):

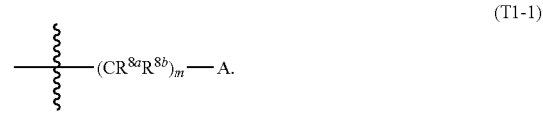

(T1-1)

Compounds according to the invention having the general formula (Ia) are particularly preferred:

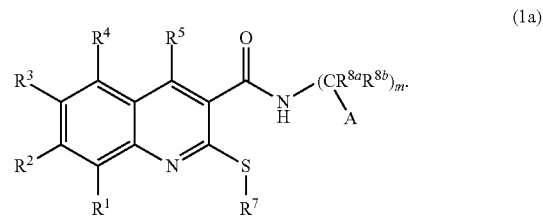

(Ia)

In a further preferred embodiment the substituent R$^7$ stands for

C$_{1-10}$ alkyl or C$_{2-10}$ heteroalkyl, each saturated or unsaturated, branched or unbranched, unsubstituted or mono- or polysubstituted with one or more substituents selected independently of one another from the group consisting of F, Cl, Br, I, NO$_2$, CF$_3$, CN, OH, =O, C(=O)—OH, OCF$_3$, NH$_2$, S(=O)$_2$OH, SH, SCF$_3$, C$_{1-8}$ alkyl, O—C$_{1-8}$ alkyl, S—C$_{1-8}$ alkyl, NH—C$_{1-8}$ alkyl, N(C$_{1-8}$ alkyl)$_2$, C$_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—C$_{1-8}$ alkyl, OH and OCF$_3$, and wherein the aforementioned C$_{3-10}$ cycloalkyl or heterocyclyl can be saturated or unsaturated, unsubstituted or mono- or polysubstituted with one or more substituents selected independently of one another from the group consisting of F, Cl, Br, I, C$_{1-8}$ alkyl, OH, =O, O—C$_{1-8}$ alkyl, OCF$_3$, NH$_2$, NH—C$_{1-8}$ alkyl and N(C$_{1-8}$ alkyl)$_2$;

C$_{3-10}$ cycloalkyl or heterocyclyl or C$_{1-8}$ alkyl- or C$_{2-8}$ heteroalkyl-bridged C$_{3-10}$ cycloalkyl or heterocyclyl, each saturated or unsaturated, unsubstituted or mono- or polysubstituted with one or more substituents selected independently of one another from the group consisting of F, Cl, Br, I, $NO_2$, CN, OH, =O, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—$C_{1-8}$ alkyl, OH and $OCF_3$; and wherein the aforementioned $C_{3-10}$ cycloalkyl or heterocyclyl can be saturated or unsaturated, unsubstituted or mono- or polysubstituted with one or more substituents selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$;

aryl or heteroaryl or $C_{1-8}$ alkyl- or $C_{2-8}$ heteroalkyl-bridged aryl or heteroaryl, each unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$.

$R^7$ preferably stands for $C_{1-8}$ alkyl or $C_{2-8}$ heteroalkyl, each saturated or unsaturated, branched or unbranched, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-8}$ cycloalkyl or heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$;

$C_{3-8}$ cycloalkyl or heterocyclyl or $C_{1-6}$ alkyl- or $C_{2-6}$ heteroalkyl-bridged $C_{3-8}$ cycloalkyl or heterocyclyl, each saturated or unsaturated, unsubstituted or mono- or polysubstituted with one or more substituents selected independently of one another from the group consisting of F, Cl, Br, I, $NO_2$, CN, OH, =O, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-8}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$; and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$;

aryl or heteroaryl or $C_{1-6}$ alkyl- or $C_{2-6}$ heteroalkyl-bridged aryl or heteroaryl, each unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$.

$R^7$ is particularly preferably selected from the group consisting of methyl, ethyl, n-propyl, isopropyl, n-butyl, 2-butyl, tert-butyl, n-pentyl, isopentyl, neopentyl, n-hexyl, cyclopropyl, cyclobutyl, cyclopentyl, cyclohexyl, methyl cyclopropyl, methyl cyclobutyl, methyl cyclopentyl, methyl cyclohexyl, ethyl cyclopropyl, ethyl cyclobutyl, ethyl cyclopentyl, ethyl cyclohexyl, each unsubstituted or mono- or polysubstituted with one or more substituents selected from the group consisting of F, Cl, Br, I, $OCF_3$, $SCF_3$, $CF_3$ and $OC_{1-8}$ alkyl; or phenyl, benzyl or phenethyl, each unsubstituted or mono- or polysubstituted with one or more substituents selected from the group consisting of F, Cl, Br, I, $OCF_3$, $SCF_3$, $CF_3$, $C_{1-8}$ alkyl, $OC_{1-8}$ alkyl and CN.

$R^7$ most particularly preferably stands for methyl, ethyl, isopropyl, tert-butyl or cyclopropyl.

Particularly preferred compounds are those from the group comprising:

1 2-(Pentylthio)-N-(2-thienylmethyl)-3-quinoline carboxamide;
2 3-[[3-[Oxo-(2-thienylmethylamino)methyl]-quinolyl]thio] propanoic acid methyl ester;
3 2-(3-Cyclohexylpropylthio)-N-(2-thienylmethyl)-3-quinoline carboxamide;
4 2-(3-Phenylpropylthio)-N-(2-thienylmethyl)-3-quinoline carboxamide;
5 2-[2-(Phenylsulfonyl)ethylthio]-N-(2-thienyl-methyl)-3-quinoline carboxamide;
6 2-[3-(4-Fluorophenyl)propylthio]-N-(2-thienylmethyl)-3-quinoline carboxamide;
7 2-(Ethylthio)-N-(2-thienylmethyl)-3-quinoline carboxamide;
8 2-[2-(Phenylsulfonyl)ethylthio]-N-(2-thienyl-methyl)-6-(trifluoromethyl)-3-quinoline carboxamide;
9 2-[2-(Phenylsulfonyl)ethylthio]-N-(2-thienylmethyl)-7-(trifluoromethyl)-3-quinoline carboxamide;
10 2-[2-(Phenylsulfonyl)ethylthio]-N-(2-thienylmethyl)-5-(trifluoromethyl)-3-quinoline carboxamide;
11 2-(Pentylthio)-N-(2-thienylmethyl)-6-(trifluoromethyl)-3-quinoline carboxamide;
12 2-(Ethylthio)-N-(2-thienylmethyl)-6-(trifluoromethyl)-3-quinoline carboxamide;
13 N-(2-Thienylmethyl)-2-[2-[3-(trifluoromethyl)-phenyl] sulfonylethylthio]-3-quinoline carboxamide;
14 2-(Ethylthio)-N-(2-thienylmethyl)-7-(trifluoromethyl)-3-quinoline carboxamide;
15 2-(Pentylthio)-N-(2-thienylmethyl)-7-(trifluoromethyl)-3-quinoline carboxamide;
16 2-[2-(4-Fluorophenyl)sulfonylethylthio]-N-(2-thienylmethyl)-3-quinoline carboxamide;
17 2-[2-(p-Tolylsulfonyl)ethylthio]-N-(2-thienylmethyl)-3-quinoline carboxamide;
18 2-[2-(p-Tolylthio)ethylthio]-N-(2-thienylmethyl)-3-quinoline carboxamide;
19 2-[2-(Phenylsulfonyl)ethylthio]-N-(cyclohexylmethyl)-3-quinoline carboxamide;
20 2-[3-(p-Tolyl)propylthio]-N-(2-thienylmethyl)-3-quinoline carboxamide;
21 2-[2-(Phenylthio)ethylthio]-N-(2-thienylmethyl)-3-quinoline carboxamide;
22 2-[2-(Phenylsulfonyl)ethylthio]-N-(2-cyclohexylethyl)-3-quinoline carboxamide;
23 2-[2-(Phenylsulfonyl)ethylthio]-N-(3,3-dimethylbutyl)-3-quinoline carboxamide;
24 2-[2-[(4-Fluorophenyl)thio]ethylthio]-N-(2-thienylmethyl)-3-quinoline carboxamide;
25 N-(3,3-Dimethylbutyl)-2-(ethylthio)-4-methyl-7-(trifluoromethyl)-3-quinoline carboxamide;
26 3-(3-(Thiophen-2-ylmethylcarbamoyl)-6-(trifluoromethyl)quinolin-2-ylthio)propanoic acid methyl ester;
27 3-(3-(Thiophen-2-ylmethylcarbamoyl)-7-(trifluoromethyl)quinolin-2-ylthio)propanoic acid methyl ester;
28 N-(2,2-Dimethylpropyl)-2-ethylsulfanyl-4-methyl-7-(trifluoromethyl)-quinoline-3-carboxamide
29 N-(Cycloheptylmethyl)-2-ethylsulfanyl-4-methyl-7-(trifluoromethyl)-quinoline-3-carboxamide
31 N-[(3,4-Difluorophenyl)-methyl]-2-ethylsulfanyl-4-methyl-7-(trifluoromethyl)-quinoline-3-carboxamide
32 N-[(2,4-Difluorophenyl)-methyl]-2-ethylsulfanyl-4-methyl-7-(trifluoromethyl)-quinoline-3-carboxamide
33 2-Ethylsulfanyl-4-methyl-7-(trifluoromethyl)-N-[(3,4,5-trifluorophenyl)-methyl]-quinoline-3-carboxamide
34 2-Ethylsulfanyl-4-methyl-7-(trifluoromethyl)-N-[(2,4,5-trifluorophenyl)-methyl]-quinoline-3-carboxamide
35 2-Ethylsulfanyl-4-methyl-N-(pyridin-4-yl-methyl)-7-(trifluoromethyl)-quinoline-3-carboxamide
36 N-[(4-tert-Butylphenyl)-methyl]-2-ethylsulfanyl-4-methyl-7-(trifluoromethyl)-quinoline-3-carboxamide
37 2-Ethylsulfanyl-4-methyl-N-(3-methylbutyl)-7-(trifluoromethyl)-quinoline-3-carboxamide
38 2-Ethylsulfanyl-4-methyl-7-(trifluoromethyl)-N-[[3-(trifluoromethyl)phenyl]-methyl]-quinoline-3-carboxamide
39 2-Ethylsulfanyl-4-methyl-N-phenethyl-7-(trifluoromethyl)-quinoline-3-carboxamide
40 2-Ethylsulfanyl-4-methyl-N-(3-phenylpropyl)-7-(trifluoromethyl)-quinoline-3-carboxamide
41 2-Ethylsulfanyl-4-methyl-N-(pyridin-2-yl-methyl)-7-(trifluoromethyl)-quinoline-3-carboxamide
42 2-Ethylsulfanyl-4-methyl-N-(pyridin-3-yl-methyl)-7-(trifluoromethyl)-quinoline-3-carboxamide
43 2-Ethylsulfanyl-4-methyl-N-(naphthalen-2-yl-methyl)-7-(trifluoromethyl)-quinoline-3-carboxamide
44 2-Ethylsulfanyl-4-methyl-N-(thiazol-2-yl-methyl)-7-(trifluoromethyl)-quinoline-3-carboxamide
45 2-Ethylsulfanyl-4-methyl-N-([1,3,4]oxadiazol-2-yl-methyl)-7-(trifluoromethyl)-quinoline-3-carboxamide
47 N-[(3-Fluorophenyl)-methyl]-2-(isopropylsulfanyl)-4-methyl-7-(trifluoromethyl)-quinoline-3-carboxamide
48 2-(Cyclopentylsulfanyl)-N-[(3-fluorophenyl)-methyl]-4-methyl-7-(trifluoromethyl)-quinoline-3-carboxamide
49 2-(Butylsulfanyl)-N-[(3-fluorophenyl)-methyl]-4-methyl-7-(trifluoromethyl)-quinoline-3-carboxamide
50 N-[(3-Fluorophenyl)-methyl]-4-methyl-2-(pentylsulfanyl)-7-(trifluoromethyl)-quinoline-3-carboxamide 51 N-[(3-Fluorophenyl)-methyl]-4-methyl-2-(1-methyl-propylsulfanyl)-7-(trifluoromethyl)-quinoline-3-carboxamide
52 2-(Cyclohexylsulfanyl)-N-[(3-fluorophenyl)-methyl]-4-methyl-7-(trifluoromethyl)-quinoline-3-carboxamide
53 N-(2-Cyclopentylethyl)-2-ethylsulfanyl-4-methyl-7-(trifluoromethyl)-quinoline-3-carboxamide
54 N-(3-Cyclopentylpropyl)-2-ethylsulfanyl-4-methyl-7-(trifluoromethyl)-quinoline-3-carboxamide
55 2-Ethylsulfanyl-4-methyl-7-(trifluoromethyl)-N-[[4-(trifluoromethyl)-phenyl]-methyl]-quinoline-3-carboxamide
56 N-[(3-tert-Butylphenyl)-methyl]-2-ethylsulfanyl-4-methyl-7-(trifluoromethyl)-quinoline-3-carboxamide
57 2-Ethylsulfanyl-4-methyl-N-(4-methylpentyl)-7-(trifluoromethyl)-quinoline-3-carboxamide
58 2-Benzylsulfanyl-N-[(3-fluorophenyl)-methyl]-4-methyl-7-(trifluoromethyl)-quinoline-3-carboxamide
59 2-Ethylsulfanyl-N-[(3-fluoro-2-methoxyphenyl)-methyl]-4-methyl-7-(trifluoromethyl)-quinoline-3-carboxamide
60 2-Ethylsulfanyl-N-[(5-fluoro-2-methoxyphenyl)-methyl]-4-methyl-7-(trifluoromethyl)-quinoline-3-carboxamide
61 N-[(3,4-Dimethylphenyl)-methyl]-2-ethylsulfanyl-4-methyl-7-(trifluoromethyl)-quinoline-3-carboxamide
62 2-Ethylsulfanyl-4-methyl-7-(trifluoromethyl)-N-[[4-(trifluoromethylsulfanyl)-phenyl]-methyl]-quinoline-3-carboxamide
63 N-(Cyclohexylmethyl)-2-ethylsulfanyl-4-methyl-7-(trifluoromethyl)-quinoline-3-carboxamide
64 2-Ethylsulfanyl-4-methyl-N-(tetrahydropyran-2-yl-methyl)-7-(trifluoromethyl)-quinoline-3-carboxamide
65 2-Ethylsulfanyl-4-methyl-N-propyl-7-(trifluoromethyl)-quinoline-3-carboxamide
66 N-Butyl-2-ethylsulfanyl-4-methyl-7-(trifluoromethyl)-quinoline-3-carboxamide
67 2-Ethylsulfanyl-N-(2-methoxyethyl)-4-methyl-7-(trifluoromethyl)-quinoline-3-carboxamide
68 2-Ethylsulfanyl-4-methyl-N-pentyl-7-(trifluoromethyl)-quinoline-3-carboxamide
69 2-Ethylsulfanyl-4-methyl-N-[(5-methylthiophen-2-ylymethyl]-7-(trifluoromethyl)-quinoline-3-carboxamide
70 2-Ethylsulfanyl-4-methyl-N-[(4-methylthiophen-2-ylymethyl]-7-(trifluoromethyl)-quinoline-3-carboxamide
71 N-[(5-Chlorothiophen-2-ylymethyl]-2-ethylsulfanyl-4-methyl-7-(trifluoromethyl)-quinoline-3-carboxamide
72 2-Ethylsulfanyl-4-methyl-N-(2-thiophen-2-yl-ethyl)-7-(trifluoromethyl)-quinoline-3-carboxamide
73 N-(5-Bicyclo[2.2.1]heptanylmethyl)-2-ethylsulfanyl-4-methyl-7-(trifluoromethyl)-quinoline-3-carboxamide
74 N-Benzyl-2-ethylsulfanyl-4-methyl-7-(trifluoromethyl)-quinoline-3-carboxamide
75 2-Ethylsulfanyl-N-[(2-fluorophenyl)-methyl]-4-methyl-7-(trifluoromethyl)-quinoline-3-carboxamide
76 2-Ethylsulfanyl-N-[(3-fluorophenyl)-methyl]-4-methyl-7-(trifluoromethyl)-quinoline-3-carboxamide
77 2-Ethylsulfanyl-N-[(4-fluorophenyl)-methyl]-4-methyl-7-(trifluoromethyl)-quinoline-3-carboxamide
78 N-[(2-Chlorophenyl)-methyl]-2-ethylsulfanyl-4-methyl-7-(trifluoromethyl)-quinoline-3-carboxamide
79 N-[(3-Chlorophenyl)-methyl]-2-ethylsulfanyl-4-methyl-7-(trifluoromethyl)-quinoline-3-carboxamide
80 N-[(4-Chlorophenyl)-methyl]-2-ethylsulfanyl-4-methyl-7-(trifluoromethyl)-quinoline-3-carboxamide
81 2-Ethylsulfanyl-4-methyl-N-(o-tolylmethyl)-7-(trifluoromethyl)-quinoline-3-carboxamide
82 2-Ethylsulfanyl-4-methyl-N-(m-tolylmethyl)-7-(trifluoromethyl)-quinoline-3-carboxamide
83 2-Ethylsulfanyl-4-methyl-N-(p-tolylmethyl)-7-(trifluoromethyl)-quinoline-3-carboxamide
84 2-Ethylsulfanyl-N-[(2-methoxyphenyl)-methyl]-4-methyl-7-(trifluoromethyl)-quinoline-3-carboxamide
85 2-Ethylsulfanyl-N-[(3-methoxyphenyl)-methyl]-4-methyl-7-(trifluoromethyl)-quinoline-3-carboxamide
86 2-Ethylsulfanyl-N-[(4-methoxyphenyl)-methyl]-4-methyl-7-(trifluoromethyl)-quinoline-3-carboxamide
87 N-[(3,5-Difluorophenyl)-methyl]-2-ethylsulfanyl-4-methyl-7-(trifluoromethyl)-quinoline-3-carboxamide
88 4-Methyl-2-methylsulfanyl-N-(thiophen-2-yl-methyl)-7-(trifluoromethyl)-quinoline-3-carboxamide
89 2-(tert-Butylsulfanyl)-4-methyl-N-(thiophen-2-yl-methyl)-7-(trifluoromethyl)-quinoline-3-carboxamide
90 N-(2,2-Dimethylpropyl)-2-ethylsulfanyl-7-(trifluoromethyl)-quinoline-3-carboxamide
91 2-Ethylsulfanyl-4-methyl-N-(thiophen-2-yl-methyl)-quinoline-3-carboxamide
92 2-Ethylsulfanyl-N-[(3-fluorophenyl)-methyl]-4-methyl-quinoline-3-carboxamide
93 2-(tert-Butylsulfanyl)-N-[(3-fluorophenyl)-methyl]-4-methyl-7-(trifluoromethyl)-quinoline-3-carboxamide
94 2-(tert-Butylsulfanyl)-N-[(4-fluorophenyl)-methyl]-4-methyl-7-(trifluoromethyl)-quinoline-3-carboxamide
95 7-tert-Butyl-2-ethylsulfanyl-N-[(3-fluorophenyl)-methyl]-4-methyl-quinoline-3-carboxamide
96 7-tert-Butyl-2-ethylsulfanyl-N-[(4-fluorophenyl)-methyl]-4-methyl-quinoline-3-carboxamide
97 2-Ethylsulfanyl-N-[(3-fluorophenyl)-methyl]-7-methoxy-4-methyl-quinoline-3-carboxamide
98 2-Ethylsulfanyl-N-[(4-fluorophenyl)-methyl]-7-methoxy-4-methyl-quinoline-3-carboxamide
99 2-Ethylsulfanyl-N-[(3-fluorophenyl)-methyl]-4,6-dimethyl-quinoline-3-carboxamide
100 2-Ethylsulfanyl-N-[(4-fluorophenyl)-methyl]-4,6-dimethyl-quinoline-3-carboxamide
101 2-Ethylsulfanyl-N-[(3-fluorophenyl)-methyl]-6-methoxy-4-methyl-quinoline-3-carboxamide
102 2-Ethylsulfanyl-N-[(4-fluorophenyl)-methyl]-6-methoxy-4-methyl-quinoline-3-carboxamide
103 2-Ethylsulfanyl-N-[(3-fluorophenyl)-methyl]-4-methyl-6-(trifluoromethyl)-quinoline-3-carboxamide
104 2-Ethylsulfanyl-N-[(4-fluorophenyl)-methyl]-4-methyl-6-(trifluoromethyl)-quinoline-3-carboxamide
105 2-Ethylsulfanyl-7-fluoro-N-[(3-fluorophenyl)-methyl]-4-methyl-quinoline-3-carboxamide
106 2-Ethylsulfanyl-7-fluoro-N-[(4-fluorophenyl)-methyl]-4-methyl-quinoline-3-carboxamide
107 2-Ethylsulfanyl-N-[(3-fluorophenyl)-methyl]-4,7-dimethyl-quinoline-3-carboxamide
108 2-Ethylsulfanyl-N-[(4-fluorophenyl)-methyl]-4,7-dimethyl-quinoline-3-carboxamide
109 2-Ethylsulfanyl-6,7-difluoro-N-[(4-fluorophenyl)-methyl]-4-methyl-quinoline-3-carboxamide
110 2-Ethylsulfanyl-N-(furan-2-yl-methyl)-4-methyl-7-(trifluoromethyl)-quinoline-3-carboxamide
111 2-Ethylsulfanyl-4-methyl-N-[(5-methyl-furan-2-ylymethyl]-7-(trifluoromethyl)-quinoline-3-carboxamide
113 2-Ethylsulfanyl-N-[(3-hydroxyphenyl)-methyl]-4-methyl-7-(trifluoromethyl)-quinoline-3-carboxamide
114 N-[(3-Fluorophenyl)-methyl]-4-methyl-2-methylsulfanyl-7-(trifluoromethyl)-quinoline-3-carboxamide
115 N-[(4-Fluorophenyl)-methyl]-4-methyl-2-methylsulfanyl-7-(trifluoromethyl)-quinoline-3-carboxamide 116 2-Ethylsulfanyl-6-fluoro-N-[(3-fluorophenyl)-methyl]-4-methyl-quinoline-3-carboxamide
117 2-Ethylsulfanyl-6-fluoro-N-[(4-fluorophenyl)-methyl]-4-methyl-quinoline-3-carboxamide
118 2-Ethylsulfanyl-6,7-difluoro-N-[(3-fluorophenyl)-methyl]-4-methyl-quinoline-3-carboxamide
119 2-Ethylsulfanyl-N-[(4-hydroxyphenyl)-methyl]-4-methyl-7-(trifluoromethyl)-quinoline-3-carboxamide
120 2-Ethylsulfanyl-8-fluoro-N-[(3-fluorophenyl)-methyl]-4-methyl-quinoline-3-carboxamide
121 2-Ethylsulfanyl-8-fluoro-N-[(4-fluorophenyl)-methyl]-4-methyl-quinoline-3-carboxamide
123 2-Ethylsulfanyl-5-fluoro-N-[(3-fluorophenyl)-methyl]-4-methyl-quinoline-3-carboxamide
124 2-Ethylsulfanyl-5-fluoro-N-[(4-fluorophenyl)-methyl]-4-methyl-quinoline-3-carboxamide
125 2-Ethylsulfanyl-N-[(3-fluorophenyl)-methyl]-5-methoxy-4-methyl-quinoline-3-carboxamide
126 2-Ethylsulfanyl-N-[(4-fluorophenyl)-methyl]-5-methoxy-4-methyl-quinoline-3-carboxamide
127 2-Ethylsulfanyl-N-[(3-fluorophenyl)-methyl]-5-hydroxy-4-methyl-quinoline-3-carboxamide
128 2-Ethylsulfanyl-N-[(3-fluorophenyl)-methyl]-6-hydroxy-4-methyl-quinoline-3-carboxamide
129 2-Ethylsulfanyl-N-[(3-fluorophenyl)-methyl]-7-hydroxy-4-methyl-quinoline-3-carboxamide
133 7-Dimethylamino-2-ethylsulfanyl-N-[(4-fluorophenyl)-methyl]-4-methyl-quinoline-3-carboxamide
134 2-Ethylsulfanyl-N-[(3-fluorophenyl)-methyl]-4-methyl-7-morpholin-4-yl-quinoline-3-carboxamide
135 2-Ethylsulfanyl-N-[(4-fluorophenyl)-methyl]-4-methyl-7-morpholin-4-yl-quinoline-3-carboxamide
136 2-Ethylsulfanyl-N-[(3-fluorophenyl)-methyl]-4-methyl-8-(trifluoromethyl)-quinoline-3-carboxamide
137 2-Ethylsulfanyl-N-[(4-fluorophenyl)-methyl]-4-methyl-8-(trifluoromethyl)-quinoline-3-carboxamide
138 2-Ethylsulfanyl-N-[(3-fluorophenyl)-methyl]-8-methoxy-4-methyl-quinoline-3-carboxamide
139 2-Ethylsulfanyl-N-[(4-fluorophenyl)-methyl]-8-methoxy-4-methyl-quinoline-3-carboxamide
140 2-Ethylsulfanyl-N-[(3-fluorophenyl)-methyl]-8-hydroxy-4-methyl-quinoline-3-carboxamide
141 7-Dimethylamino-2-ethylsulfanyl-N-[(3-fluorophenyl)-methyl]-4-methyl-quinoline-3-carboxamide
142 2-Ethylsulfanyl-N-[(3-fluorophenyl)-methyl]-4-methyl-7-(trifluoromethyloxy)-quinoline-3-carboxamide
143 4-Ethyl-2-ethylsulfanyl-N-[(3-fluorophenyl)-methyl]-7-(trifluoromethyl)-quinoline-3-carboxamide
144 2-Ethylsulfanyl-N-[(3-fluorophenyl)-methyl]-4-isopropyl-7-(trifluoromethyl)-quinoline-3-carboxamide
or the physiologically compatible salts thereof.

The substituted 2-mercaptoquinoline-3-carboxamides according to the invention and the corresponding acids, bases, salts and solvates are suitable as pharmaceutical active ingredients in medicaments.

The invention therefore also provides a medicament containing at least one substituted 2-mercaptoquinoline-3-carboxamide according to the invention having the general formula (1), wherein the radicals $R^1$ to $R^7$ have the meaning given above, and optionally one or more pharmaceutically compatible auxiliary substances.

The medicaments according to the invention optionally contain, in addition to at least one compound according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the medicament is to be administered by oral, peroral, parenteral, intravenous, intraperitoneal, intradermal, intramuscular, intranasal, buccal, rectal or local means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Compounds according to the invention in a depot formulation, in dissolved form or in a plaster, optionally with addition of agents promoting skin penetration, are suitable preparations for percutaneous administration. Preparation forms suitable for oral or percutaneous administration can deliver the compounds according to the invention on a delayed release basis. The compounds according to the invention can also be used in parenteral long-term depot forms, such as implants or implanted pumps, for example. Other additional active ingredients known to the person skilled in the art can be added in principle to the medicaments according to the invention.

These medicaments according to the invention are suitable for influencing KCNQ2/3 channels and exert an agonistic or antagonistic, in particular an agonistic, action.

The medicaments according to the invention are preferably suitable for the treatment of disorders or diseases which are at least partly mediated by KCNQ2/3 channels.

The medicaments according to the invention are preferably suitable for the treatment of one or more diseases chosen from the group consisting of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

The medicaments according to the invention are particularly preferably suitable for the treatment of pain, most particularly preferably chronic pain, neuropathic pain, inflammatory pain and muscular pain.

The medicaments according to the invention are further particularly preferably suitable for the treatment of epilepsy.

The invention also provides the use of at least one substituted 2-mercaptoquinoline-3-carboxamide according to the invention and optionally one or more pharmaceutically compatible auxiliary substances for the preparation of a medicament for the treatment of disorders or diseases which are at least partly mediated by KCNQ2/3 channels.

Preference is given to the use of at least one substituted 2-mercaptoquinoline-3-carboxamide according to the invention and optionally one or more pharmaceutically compatible auxiliary substances for the preparation of a medicament for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is the use of at least one substituted 2-mercaptoquinoline-3-carboxamide according to the invention and optionally one or more pharmaceutically compatible auxiliary substances for the preparation of a medicament for the treatment of pain, most particularly preferably chronic pain, neuropathic pain, inflammatory pain and muscular pain.

Also particularly preferred is the use of at least one substituted 2-mercaptoquinoline-3-carboxamide according to the invention and optionally one or more pharmaceutically compatible auxiliary substances for the preparation of a medicament for the treatment of epilepsy.

The invention also provides at least one substituted 2-mercaptoquinoline-3-carboxamide according to the invention and optionally one or more pharmaceutically compatible auxiliary substances for the treatment of disorders or diseases which are at least partly mediated by KCNQ2/3 channels.

The invention also provides at least one substituted 2-mercaptoquinoline-3-carboxamide according to the invention and optionally one or more pharmaceutically compatible auxiliary substances for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is at least one substituted 2-mercaptoquinoline-3-carboxamide according to the invention and optionally one or more pharmaceutically compatible auxiliary substances for the treatment of pain, most particularly preferably chronic pain, neuropathic pain, inflammatory pain and muscular pain.

Particularly preferred is also at least one substituted 2-mercaptoquinoline-3-carboxamide according to the invention and optionally one or more pharmaceutically compatible auxiliary substances for the treatment of epilepsy.

The effectiveness against pain can be demonstrated for example in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363). The effectiveness against epilepsy can be demonstrated for example in the DBA/2 mouse model (De Sarro et al., Naunyn-Schmiedeberg's Arch. Pharmacol. 2001, 363, 330-336).

The substituted 2-mercaptoquinoline-3-carboxamides according to the invention preferably have an $EC_{50}$ value of at most 10 µM or at most 5 µM, more preferably at most 3 µM or at most 2 µM, even more preferably at most 1.5 µM or at most 1 µM, most preferably at most 0.8 µM or at most 0.5 µM and in particular at most 0.4 µM or at most 0.2 µM. Methods for determining the $EC_{50}$ value are known to the person skilled in the art. The $EC_{50}$ value is preferably determined by fluorimetry, particularly preferably by the method described in "Pharmacological experiments".

The invention also provides methods for preparing the substituted 2-mercaptoquinoline-3-carboxamides according to the invention.

The chemicals and reaction components used in the reactions described below are available commercially or can be produced by conventional methods known to the person skilled in the art.

General Reaction Scheme

Scheme 1:

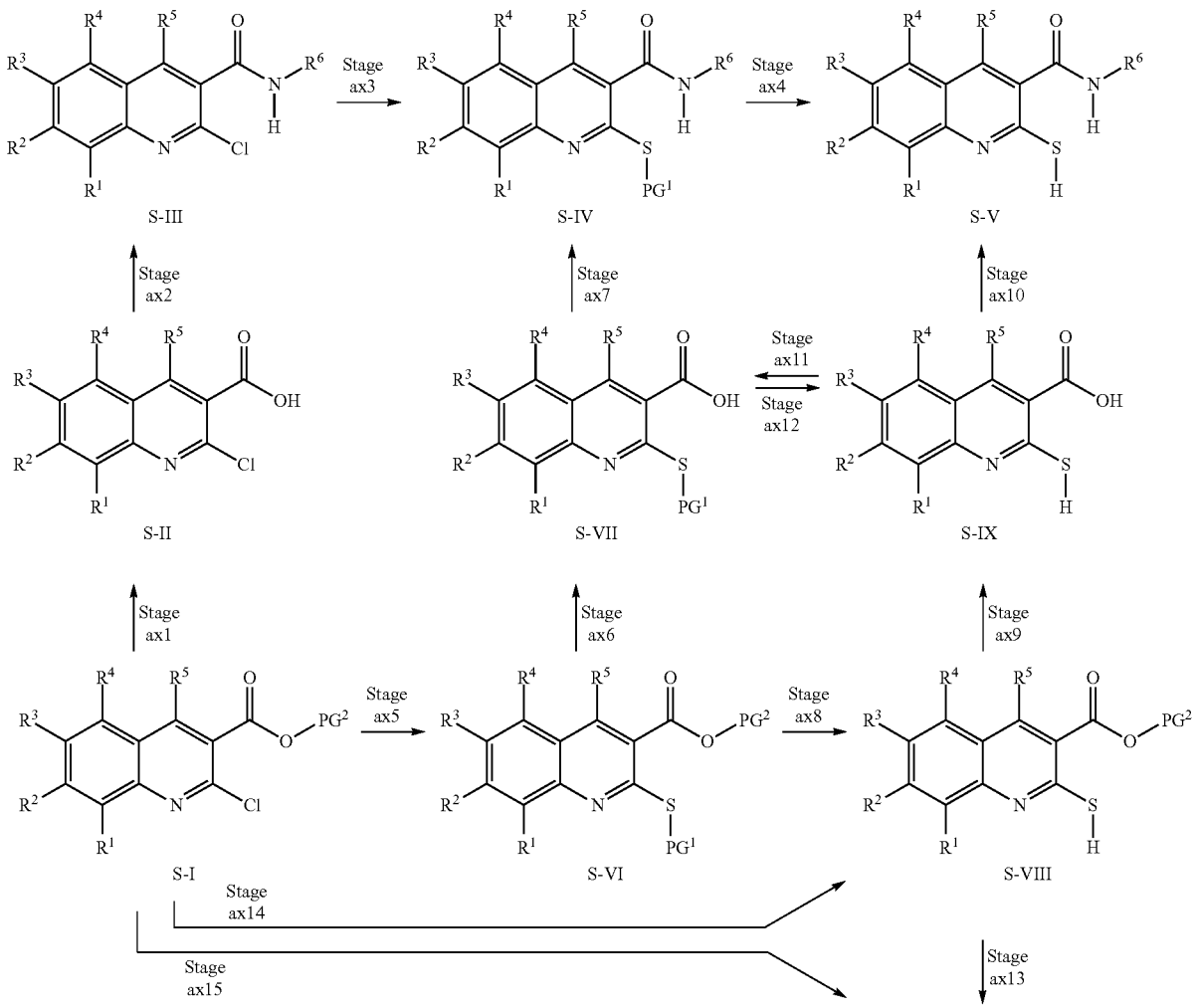

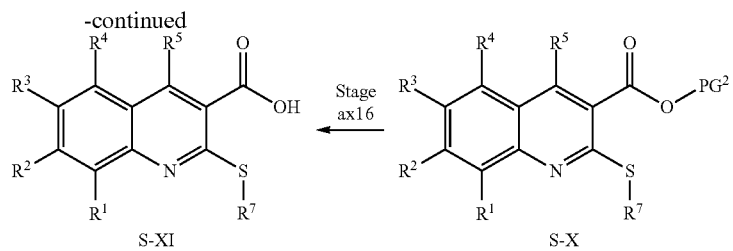

In steps ax1, ax6, ax9 and ax16 the protective group $PG^2$ of the protected ester S—I or S-VI or S-VIII or S—X, which is a tert-butyl or a benzyl group for example, is cleaved by ester cleavage methods known to the person skilled in the art, optionally in the presence of an acid or a base, and S-I, S-VI, S-VIII or S-X are thus converted into the carboxylic acid S-II or S-VII or S-IX or S-XI.

In steps ax2, ax7 and ax10 the carboxylic acid S-II or S-VII or S-IX can be converted into the corresponding amide S-III or S-IV or S-V by methods familiar to the person skilled in the art. For example, S-II or S-VII or S-IX can first be reacted with a suitable chlorinating agent such as thionyl chloride to form the acid chloride, which is then reacted with the primary amine $R^6$—$NH_2$, optionally in the presence of a base, to form the amide S-III or S-IV or S-V. Alternatively, S-II or S-VII or S-IX can be reacted with the primary amine $R^6$—$NH_2$ in the presence of a suitable coupling reagent, such as for example HATU or CDI, optionally with addition of a base.

In steps ax3 and ax5 the thiols S-IV and S-VI protected by the protective group $PG^1$ can be formed starting from the 2-chloroquinolines S-III and S-I by methods familiar to the person skilled in the art, for example by alkylation with the corresponding thiol $PG^1$-SH in an ipso-substitution to form the thio ether S-IV and S-VI, optionally in the presence of a base.

In steps ax4, ax8 and ax12 the thiol S-IV or S-VI or S-VII which is protected as a thio ether for example can be converted into the thiol S-V or S-VIII or S-IX by cleaving off the protective group $PG^1$, optionally in the presence of an acid or a base.

In step ax11 the thiol S-IX can be converted into S-VII, which has a thiol function protected by the protective group $PG^1$, by methods familiar to the person skilled in the art. Here the thiol S-IX can be alkylated for example by the use of an alkyl halide $PG^1$-Hal, optionally in the presence of a base.

In step ax13 the thiol S-VIII can be converted into the corresponding thio ether S—X by methods familiar to the person skilled in the art. Here the thiol S-VIII can be alkylated for example by the use of the alkyl halide $R^7$—Hal, optionally in the presence of a base.

In step ax14 the 2-chloroquinoline S-I can first be converted into the corresponding thio ether by methods known to the person skilled in the art, such as for example by substitution with a thiol, for example 3-mercaptopropanoic acid ethyl ester, and then cleaved, optionally in the presence of an acid or a base, to form the thiol S-VIII.

In step ax15 the thio ether S-X can be formed starting from the 2-chloroquinoline S-I by methods familiar to the person skilled in the art, e.g. by alkylation with the corresponding thiol $R^7$—SH in an ipso-substitution, optionally in the presence of a base.

Scheme 2:

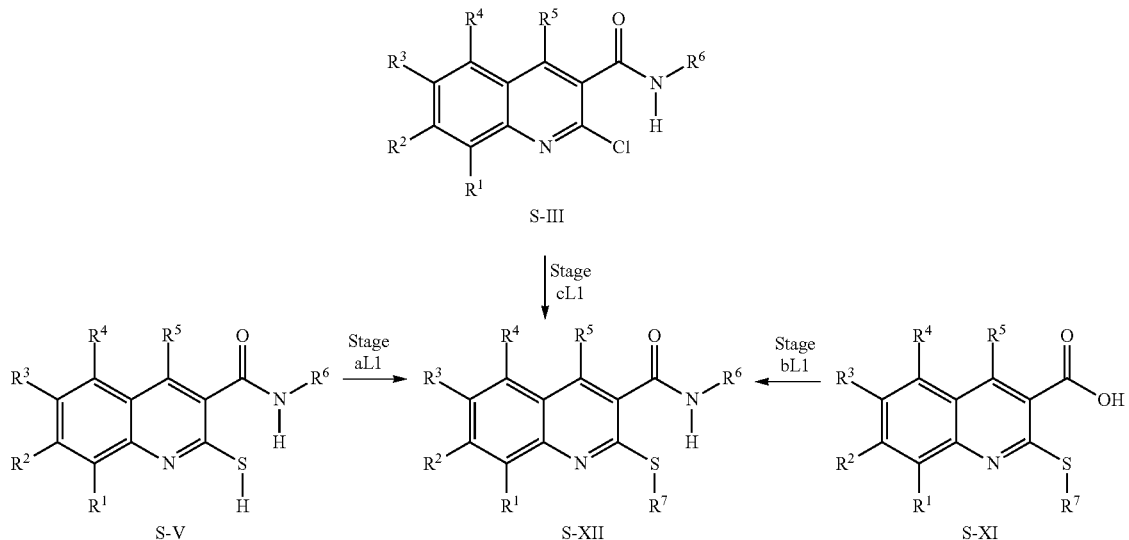

In step aL1 the thiol S-V can be converted into the corresponding thio ether S-XII by methods familiar to the person skilled in the art. Here the thiol S-V can be alkylated for example by the use of the alkyl halide $R^7$—Hal, optionally in the presence of a base.

In step bL1 the carboxylic acid S-XI can be converted into the corresponding amide S-XII by methods familiar to the person skilled in the art. For example, S-XI can first be reacted with a suitable chlorinating agent such as thionyl chloride to form the acid chloride, which is then reacted with the primary amine R⁶—NH₂, optionally in the presence of a base, to form the amide S-XII. Alternatively, S-XI can be reacted with the primary amine R⁶—NH₂ in the presence of a suitable coupling reagent, such as for example HATU or CDI, optionally with addition of a base.

In step cL1 the thio ether S-XII can be formed starting from 2-chloroquinoline S-III by methods familiar to the person skilled in the art, e.g. by alkylation with the corresponding thiol R⁷—SH in an ipso-substitution, optionally in the presence of a base.

The methods familiar to the person skilled in the art for performing reaction steps ax1 to ax16 and aL1, bL1 and cL1 can be found in the standard works on organic chemistry, such as for example J. March, Advanced Organic Chemistry, Wiley & Sons, 6th edition, 2007; F. A. Carey, R. J. Sundberg, Advanced Organic Chemistry, Parts A and B, Springer, 5th edition, 2007); various authors, Compendium of Organic Synthetic Methods, Wiley & Sons. In addition, further methods and references to the literature can be obtained from the standard databases such as the Reaxys® database from Elsevier, Amsterdam, NL or the SciFinder® database of the American Chemical Society, Washington, US.

DESCRIPTION OF THE SYNTHESES

Abbreviations

AcOH acetic acid
aq. aqueous
brine saturated aqueous NaCl solution
BuLi butyl lithium
d days
DCM dichloromethane
DIPEA N,N-diisopropylethylamine
EE ethyl acetate
EtOH ethanol
sat. saturated
h hour(s)
HATU O-(7-azabenzotriazol-1-yl)-N,N,N',N'-tetramethyluronium hexafluorophosphate
sol. solution
m/z mass-to-charge ratio
M molar
MeCN acetonitrile
MeOH methanol
min minutes
MS mass spectrometry
N/A not available
NEt₃ triethylamine
RG retigabine
RT room temperature 23±7° C.
SC column chromatography on silica gel
THF tetrahydrofuran
vv ratio by volume All starting materials not explicitly described were either available commercially (suppliers can be found for example in the Symyx® Available Chemicals Database from MDL, San Ramon, US), or their synthesis is already accurately described in the specialist literature (experimental procedures can be found for example in the Reaxys® database from Elsevier, Amsterdam, NL), or they can be prepared by the methods known to the person skilled in the art.

Silica gel 60 (0.040-0.063 mm) was used as the stationary phase for column chromatography (SC).

The analytical characterisation of all intermediates and example compounds was performed by means of ¹H-NMR spectroscopy. Analyses by mass spectrometry (MS, m/z stated for [M+H]⁺) were also performed for all example compounds and selected intermediates. CL Synthesis of Intermediates Synthesis of intermediate VVV01: 2-Chloro-N-(thiophen-2-ylmethyl)quinoline-3-carboxamide A solution of 2.1 g (10.0 mmol) 2-chloroquinoline-3-carboxylic acid in thionyl chloride (60 ml) was heated for 2 h at 85° C. Then excess thionyl chloride was removed under vacuum. The residue was taken up with DCM (60 ml) and the solution was cooled to 0° C. and then mixed with 4.0 ml (30.0 mmol) NEt₃ and 1.03 ml (10.0 mmol) thiophene-2-methylamine. After stirring for 90 min at RT it was diluted with EE and washed with a saturated aqueous NH₄Cl solution. The aqueous phase was extracted with EE. The combined organic phases were washed with brine, dried over Na₂SO₄, filtered and concentrated to small volume under vacuum. Column chromatography (hexane/EE 4:1) with the residue yielded 1.44 g (4.8 mmol, 48%) 2-chloro-N-(thiophen-2-ylmethyl)quinoline-3-carboxamide.

Synthesis of intermediate VVV02: 2-Mercapto-N-(thiophen-2-ylmethyl)quinoline-3-carboxamide 600 mg (26.1 mmol) sodium were added slowly to MeOH (500 ml). Then a solution of 1.16 g (3.0 mmol) 3-[[3-[oxo-(2-thienylmethylamino)methyl]-2-quinolyl]-thio]propanoic acid methyl ester (Example 2) in MeOH (60 ml) was added at RT. Then the reaction solution was heated for 1 h at 70° C. After cooling to RT the mixture was concentrated to small volume under vacuum. The residue was taken up with water and the solution was washed with EE. Then it was acidified with concentrated hydrochloric acid to pH 3. The deposit formed was filtered off and dried. 805 mg (2.7 mmol, 90%) 2-mercapto-N-(thiophen-2-ylmethyl)quinoline-3-carboxamide were obtained.

Synthesis of intermediate VVV03: 2-Chloro-6-(trifluoromethyl)quinoline-3-carboxylic acid A solution of 1.54 ml (11.0 mmol) diisopropylamine in THF (38 ml) was cooled to 0° C. 6.9 ml (1.6 M in hexane, 11.0 mmol) n-BuLi were added dropwise at this temperature and then the mixture was stirred for 30 min at −78° C. Then a solution of 2.31 g (10.0 mmol) 2-chloro-6-(trifluoromethyl)quinoline in THF (12 ml) was added dropwise at −78° C. and the mixture was stirred for a further 30 min at −78° C. Then the reaction solution was poured onto finely dispersed dry ice. After heating to RT the mixture was concentrated to small volume under vacuum and the residue was taken up with water. It was made alkaline with a 1N aqueous NaOH solution and then washed with ether. Then it was acidified with a 10% aqueous hydrochloric acid and extracted with EE. The organic phase was washed with water and brine, dried over Na₂SO₄, filtered and concentrated to small volume under vacuum. 198 mg (0.7 mmol, 72%) 2-chloro-6-(trifluoromethyl)quinoline-3-carboxylic acid were obtained as residue.

Synthesis of intermediate VVV04: 2-(2-(Phenylsulfonyl)ethylthio)-6-(trifluoromethyl)quinoline-3-carboxylic acid 206 mg (1.5 mmol) K₂CO₃ and 303 mg (1.5 mmol) 2-(phenylsulfonyl)ethanethiol were added to a solution of 827 mg (1.0 mmol) 2-chloro-6-(trifluoromethyl)quinoline-3-carboxylic acid (precursor VVV03) in acetone (3 ml) and the mixture was heated for 5 h at 70° C. Then it was filtered and the filtrate was concentrated to small volume under vacuum. The residue was dissolved in water and acidified with a 1N hydrochloric acid. It was then extracted with EE and the organic phase was dried over Na$_2$SO$_4$, filtered and concentrated to small volume under vacuum. Crystallisation (DCM/hexane) of the residue yielded 316 mg (0.7 mmol, 72%) 2-(2-(phenylsulfonyl)ethylthio)-6-(trifluoromethyl)quinoline-3-carboxylic acid.

Synthesis of intermediate VVV05: 2-Hydroxy-4-methyl-7-(trifluoromethyl)-quinoline-3-carboxylic acid ethyl ester 235 mg (60% in mineral oil, 5.89 mmol) sodium hydride were added to a solution of 1.7 g (5.36 mmol) 3-(2-acetyl-5-(trifluoromethyl)phenylamino)-3-oxopropanoic acid ethyl ester in EtOH (16 ml) and the mixture was refluxed for 3 h and stirred for a further 16 h at RT. Then 1.34 ml (6.70 mmol) AcOH were added and the mixture was diluted with EE (30 ml) and brine (10 ml). The phases were separated and the organic phase was dried over MgSO$_4$, filtered and concentrated to small volume under vacuum. Crystallisation (EE) of the residue yielded 920 mg (3.07 mmol, 57%) 2-hydroxy-4-methyl-7-(trifluoromethyl)quinoline-3-carboxylic acid ethyl ester.

Synthesis of intermediate VVV06: 2-Chloro-4-methyl-7-(trifluoromethyl)quinoline-3-carboxylic acid ethyl ester 4.3 g (14.4 mmol) 2-hydroxy-4-methyl-7-(trifluoromethyl)quinoline-3-carboxylic acid ethyl ester (precursor VVV05) were heated together with 13.3 ml (144.1 mmol) POCl$_3$ for 2 h at 100° C. After cooling to RT the mixture was concentrated to small volume under vacuum. 4.5 g (14.2 mmol, 98%) 2-chloro-4-methyl-7-(trifluoromethyl)quinoline-3-carboxylic acid ethyl ester were obtained as residue.

Synthesis of intermediate VVV07: 2-(3-Ethoxy-3-oxopropylthio)-4-methyl-7-(trifluoromethyl)quinoline-3-carboxylic acid ethyl ester 336 mg (3.0 mmol) potassium tert-butylate were added to a solution of 360 mg (3.0 mmol) 3-mercaptopropionic acid methyl ester in DMF (8 ml) at 0° C. and the mixture was stirred for 30 min at 0° C. Then 953 mg (3.0 mmol) 2-chloro-4-methyl-7-(trifluoromethyl)quinoline-3-carboxylic acid ethyl ester were added and the reaction solution was heated slowly to 50° C. and stirred for 16 h at this temperature. After cooling to RT the mixture was diluted with water and extracted with EE. The organic phase was dried over MgSO$_4$, filtered and concentrated to small volume under vacuum. Column chromatography (hexane/EE 9:1) of the residue yielded 625 mg (1.5 mmol, 50%) 2-(3-ethoxy-3-oxopropylthio)-4-methyl-7-(trifluoromethyl)quinoline-3-carboxylic acid ethyl ester.

Synthesis of intermediate VVV08: 2-(Ethylthio)-4-methyl-7-(trifluoromethyl)quinoline-3-carboxylic acid 400 mg (17.4 mmol) sodium were added slowly to MeOH (50 ml) and the solution was stirred for 5 min at RT. Then a solution of 800 mg (2.0 mmol) 2-(3-ethoxy-3-oxopropylthio)-4-methyl-7-(trifluoromethyl)quinoline-3-carboxylic acid ethyl ester (precursor VVV07) in MeOH (10 ml) was added at RT. The reaction solution was then heated for 30 min at 70° C. After cooling to RT 488 µl (6.0 mmol) 1-iodethane were added and the mixture was stirred for 2 h at RT. Then the mixture was concentrated to small volume under vacuum and the residue was taken up with EE. It was washed with water and the aqueous phase was extracted with EE. The combined organic phases were washed with brine, dried over MgSO$_4$, filtered and concentrated to small volume under vacuum. 391 mg (1.2 mmol, 62%) 2-(ethylthio)-4-methyl-7-(trifluoromethyl)quinoline-3-carboxylic acid were obtained as the residue, which was reacted further with no additional purification.

Synthesis of intermediate VVV17: 2-Chloro-N-[(3-fluorophenyl)-methyl]-4-methyl-7-(trifluoromethyl)-quinoline-3-carboxamide a) Synthesis of 2-chloro-4-methyl-7-(trifluoromethyl)quinoline-3-carbonyl chloride 50 g (55.3 mmol) 2-hydroxy-4-methyl-7-(trifluoromethyl)-quinoline-3-carboxylic acid ethyl ester (VVV05) were heated together with 51 ml (553.1 mmol) POCl$_3$ for 2 h at 100° C. Then toluene was added (10 ml) and the mixture was stirred for 10 min at 60° C. and then concentrated to small volume under vacuum. The residue was taken up with water and extracted with EE. The organic phase was washed with a 1M aqueous NaHCO$_3$ solution, water and brine, dried over MgSO$_4$, filtered and concentrated to small volume under vacuum. 12.6 g (40.9 mmol, 74%) 2-chloro-4-methyl-7-(trifluoromethyl)quinoline-3-carbonyl chloride were obtained as the residue, which was reacted further with no additional purification.

b) Synthesis of 2-chloro-N-[(3-fluorophenyl)-methyl]-4-methyl-7-(trifluoromethyl)-quinoline-3-carboxamide A solution of 2.9 g (23.4 mmol) 3-fluorobenzylamine was added dropwise at RT to a solution of 6.0 g (19.5 mmol) 2-chloro-4-methyl-7-(trifluoromethyl)quinoline-3-carbonyl chloride in dioxane (35 ml). The mixture was then stirred for 60 min at RT and then quenched with water. The reaction solution was extracted with EE and the organic phase was washed with a 1M aqueous NH$_4$Cl solution and brine, dried over MgSO$_4$, filtered and concentrated to small volume under vacuum. Crystallisation of the residue (EE) yielded 6.4 g (16.1 mmol, 83%) 2-chloro-N-[(3-fluorophenyl)-methyl]-4-methyl-7-(trifluoromethyl)-quinoline-3-carboxamide.

Synthesis of intermediate VVV22: 7-tert-Butyl-2-ethylsulfanyl-4-methyl-quinoline-3-carboxylic acid a) Synthesis of 3-(2-acetyl-5-tert-butylphenylamino)-3-oxopropanoic acid ethyl ester 160 µl (1.15 mol) NEt$_3$ were added to a solution of 200 mg (1.0 mmol) 1-(2-amino-4-tert-butylphenyl)ethanone in DCM (20 ml) and the mixture was cooled to 0° C. 170 µl (1.4 mmol) 3-chloro-3-oxopropanoic acid ethyl ester were added at this temperature and the mixture was then stirred for 2 h at RT. Then it was diluted with water and extracted with DCM. The organic phase was washed with brine, dried over Na$_2$SO$_4$, filtered and concentrated to small volume under vacuum. Column chromatography (hexane/EE 19:1) of the residue yielded 190 mg (0.62 mmol, 60%) 3-(2-acetyl-5-tert-butyl-phenylamino)-3-oxopropanoic acid ethyl ester.

b) Synthesis of 7-tert-butyl-2-hydroxy-4-methyl-quinoline-3-carboxylic acid ethyl ester 30 mg (0.68 mmol, 60% in mineral oil) sodium hydride were added to a solution of 190 mg (0.62 mmol) 3-(2-acetyl-5-tert-butyl-phenylamino)-3-oxopropanoic acid ethyl ester in EtOH (2 ml) and the mixture was heated for 2 h at 80° C. Then it was diluted with water and acidified with 5N AcOH. It was then extracted with EE. The organic phase was washed with water and brine, dried over $Na_2SO_4$, filtered and concentrated to small volume under vacuum. 150 mg (0.52 mmol, 84%) 7-tert-butyl-2-hydroxy-4-methyl-quinoline-3-carboxylic acid ethyl ester were obtained as the residue, which was reacted further with no additional purification.

c) Synthesis of 7-tert-butyl-2-chloro-4-methyl-quinoline-3-carboxylic acid ethyl ester A mixture of 150 mg (0.52 mmol) 7-tert-butyl-2-hydroxy-4-methyl-quinoline-3-carboxylic acid ethyl ester and $POCl_3$ (1 ml) was heated for 2 h at 150° C. Then the reaction solution was poured into iced water (15 ml) and made alkaline with a saturated aqueous $NaHCO_3$ solution. It was then extracted with EE and the organic phase was washed with brine, dried over $Na_2SO_4$, filtered and concentrated to small volume under vacuum. 140 mg (0.46 mmol, 88%) 7-tert-butyl-2-chloro-4-methyl-quinoline-3-carboxylic acid ethyl ester were obtained as the residue, which was reacted further with no additional purification.

d) Synthesis of 7-tert-butyl-2-ethylsulfanyl-4-methyl-quinoline-3-carboxylic acid ethyl ester 190 mg (1.38 mmol) $K_2CO_3$ and 100 µl (1.38 mmol) ethanethiol were added to a solution of 140 mg (0.46 mmol) 7-tert-butyl-2-chloro-4-methyl-quinoline-3-carboxylic acid ethyl ester in DMF (3 ml) and the mixture was stirred for 16 h at 60° C. Then it was diluted with water and extracted with EE. The organic phase was washed with brine, dried over $Na_2SO_4$, filtered and concentrated to small volume under vacuum. Column chromatography (hexane/EE 19:1) of the residue yielded 100 mg (0.30 mmol, 65%) 7-tert-butyl-2-ethylsulfanyl-4-methyl-quinoline-3-carboxylic acid ethyl ester.

e) Synthesis of 7-tert-butyl-2-ethylsulfanyl-4-methyl-quinoline-3-carboxylic acid A solution of 600 mg (14.36 mmol) lithium hydroxide monohydrate in water (30 ml) was added to a solution of 1.7 g (5.1 mmol) 7-tert-butyl-2-ethylsulfanyl-4-methyl-quinoline-3-carboxylic acid ethyl ester in a THF/methanol blend (2:1 vv, 30 ml) and then the reaction solution was stirred for 16 h at 60° C. Then the mixture was concentrated to small volume under vacuum and the residue was taken up with water and washed with EE. The aqueous phase was adjusted to pH 2 with 1M hydrochloric acid and then extracted with EE. The organic phase was washed with brine, dried over $Na_2SO_4$, filtered and concentrated to small volume under vacuum. 420 mg (1.38 mmol, 27%) 7-tert-butyl-2-ethylsulfanyl-4-methyl-quinoline-3-carboxylic acid were obtained as the residue, which was reacted further with no additional purification.

Synthesis of intermediate VVV30: 2-Ethylsulfanyl-6,7-difluoro-4-methyl-quinoline-3-carboxylic acid a) Synthesis of 6,7-difluoro-2-hydroxy-4-methyl-quinoline-3-carboxylic acid ethyl ester 6,7-Difluoro-2-hydroxy-4-methyl-quinoline-3-carboxylic acid ethyl ester was prepared from 1-(2-amino-4,5-difluorophenyl)ethanone by the method described for precursor VVV22 sections a) and b).

b) Synthesis of 2-ethylsulfanyl-6,7-difluoro-4-methyl-quinoline-3-carboxylic acid ethyl ester 3.4 g (8.2 mmol) Lawesson's reagent were added at RT to a solution of 550 mg (2.1 mmol) 6,7-difluoro-2-hydroxy-4-methyl-quinoline-3-carboxylic acid ethyl ester in a pyridine/toluene blend (1:10 vv, 6 ml) and then the mixture was heated for 3 h at 80° C. Then it was quenched with a saturated aqueous $NaHCO_3$ solution (20 ml) and extracted with EE (3×60 ml). The combined organic phases were washed with water, dried over $Na_2SO_4$, filtered and concentrated to small volume under vacuum. The residue (450 mg) was dissolved in DMF (6 ml) and mixed with 660 mg (4.8 mmol) $K_2CO_3$ and 740 mg (4.8 mmol) iodoethane. The reaction solution was then heated for 30 min at 50° C. It was then diluted with water (60 ml) and extracted with EE (3×80 ml). The combined organic phases were washed with water and brine, dried over $Na_2SO_4$, filtered and concentrated to small volume under vacuum. Column chromatography (hexane/EE 19:1) of the residue yielded 300 mg (0.96 mmol, 47%) 2-ethylsulfanyl-6,7-difluoro-4-methyl-quinoline-3-carboxylic acid ethyl ester.

c) Synthesis of 2-ethylsulfanyl-6,7-difluoro-4-methyl-quinoline-3-carboxylic acid 220 mg (0.78 mmol, 60%) 2-ethylsulfanyl-6,7-difluoro-4-methyl-quinoline-3-carboxylic acid were prepared from 400 mg (1.3 mmol) 2-ethylsulfanyl-6,7-difluoro-4-methyl-quinoline-3-carboxylic acid by the method described for precursor VVV22 section e).

Synthesis of intermediate VVV39: 7-Dimethylamino-2-ethylsulfanyl-4-methyl-quinoline-3-carboxylic acid ethyl ester a) Synthesis of 2-ethylsulfanyl-7-fluoro-4-methyl-quinoline-3-carboxylic acid ethyl ester 2-Ethylsulfanyl-7-fluoro-4-methyl-quinoline-3-carboxylic acid ethyl ester was prepared from 1-(2-amino-4-fluorophenyl)ethanone by the method described for precursor VVV30 sections a) and b).

b) Synthesis of 7-dimethylamino-2-ethylsulfanyl-4-methyl-quinoline-3-carboxylic acid ethyl ester 2.8 g (20.5 mmol) $K_2CO_3$ and a 40% aq. dimethylamine solution (20.5 ml) were added to a solution of 2.0 g (6.8 mmol) 2-ethylsulfanyl-7-fluoro-4-methyl-quinoline-3-carboxylic acid ethyl ester in EtOH (20 ml) and the mixture was heated for 16 h at 90° C. in a closed vessel. Then the reaction solution was concentrated to small volume under vacuum and the residue was taken up with water. It was then extracted with EE. The organic phase was washed with water and brine, dried over $Na_2SO_4$, filtered and concentrated to small volume under vacuum. Column chromatography (hexane/EE 25:1) of the residue yielded 810 mg (2.55 mmol, 38%) 7-dimethylamino-2-ethylsulfanyl-4-methyl-quinoline-3-carboxylic acid ethyl ester.

Synthesis of intermediate VVV41: 2-Ethylsulfanyl-N-[(3-fluorophenyl)-methyl]-4-hydroxy-7-(trifluoromethyl)-quinoline-3-carboxamide a) Synthesis of N-(1-ethylthio-2-(1-oxybutyl)-hexan-3-onylidene)-3-(trifluoromethyl)aniline A solution of 7.2 g (45.0 mmol) diethyl malonate in DMF (10 ml) was added to a solution of 2.0 g (41.2 mmol) sodium hydride in DMF (120 ml) and the mixture was then stirred at RT for 30 min. Then a solution of 10.0 g (37.5 mmol) N-(1-chloro-1-ethylthio-methylene)-3-(trifluoromethyl) aniline in DMF (10 ml) was added and the reaction solution was heated for 30 min at 100° C. Then it was diluted with water and extracted with ether. The organic phase was washed with water, dried over Na$_2$SO$_4$, filtered and concentrated to small volume under vacuum. 4.5 g (11.5 mmol, 31%) N-(1-ethylthio-2-(1-oxybutyl)-hexan-3-onylidene)-3-(trifluoromethyl) aniline were obtained as the residue, which was reacted further with no additional purification.

b) Synthesis of 2-(ethylthio)-4-hydroxy-7-(trifluoromethyl)quinoline-3-carboxylic acid ethyl ester 4.0 g (10.2 mmol) N-(1-ethylthio-2-(1-oxybutyl)-hexan-3-onylidene)-3-(trifluoromethyl)aniline were heated under vacuum for 1 h at 180° C. After cooling to RT and column chromatography (hexane/EE 249:1) of the residue, 1.0 g (2.9 mmol, 28%) 2-(ethylthio)-4-hydroxy-7-(trifluoromethyl) quinoline-3-carboxylic acid ethyl ester were obtained.

c) Synthesis of 2-(ethylthio)-N-(3-fluorobenzyl)-4-hydroxy-7-(trifluoromethyl)quinoline-3-carboxamide 5.8 ml (11.6 mmol, 2M in toluene)trimethyl aluminium and 1.5 g (11.6 mmol) 3-fluorobenzylamine were added in succession to a solution of 1.0 g (2.9 mmol) 2-(ethylthio)-4-hydroxy-7-(trifluoromethyl)quinoline-3-carboxylic acid ethyl ester in toluene (18 ml) and the mixture was then heated for 2 h at 80° C. Then it was diluted with water and extracted with EE. The organic phase was washed with 1M hydrochloric acid, water and brine, dried over Na$_2$SO$_4$, filtered and concentrated to small volume under vacuum. Column chromatography (hexane/EE 17:3) of the residue yielded 0.9 g (2.1 mmol, 73%) 2-(ethylthio)-N-(3-fluorobenzyl)-4-hydroxy-7-(trifluoromethyl)quinoline-3-carboxamide.

Synthesis of Further Intermediates

The synthesis of further intermediates took place by the methods already described. Table 1 shows which compound was prepared by which method. The starting materials and reagents used in each case are apparent to the person skilled in the art.

TABLE 1

| Intermediate | Chemical name | Preparation analogous to intermediate |
| --- | --- | --- |
| VVV09 | 2-Chloro-N-(cyclohexylmethyl)quinoline-3-carboxamide | VVV01 |
| VVV10 | 2-Chloro-N-(2-cyclohexylethyl)quinoline-3-carboxamide | VVV01 |
| VVV11 | 2-Chloro-N-(3,3-dimethylbutyl)quinoline-3-carboxamide | VVV01 |
| VVV12 | 2-Chloro-7-(trifluoromethyl)quinoline-3-carboxylic acid | VVV03 |
| VVV13 | 2-Chloro-N-(thiophen-2-ylmethyl)-7-(trifluoromethyl)quinoline-3-carboxamide | VVV01 |
| VVV14 | 2-(3-Methoxy-3-oxopropylthio)-6-(trifluoromethyl)quinoline-3-carboxylic acid | VVV04 |
| VVV15 | 2-Chloro-5-(trifluoromethyl)quinoline-3-carboxylic acid | VVV03 |
| VVV16 | 2-Chloro-N-(thiophen-2-ylmethyl)-5-(trifluoromethyl)quinoline-3-carboxamide | VVV01 |
| VVV18 | 4-Methyl-2-methylsulfanyl-7-(trifluoromethyl)-quinoline-3-carboxylic acid | VVV08 |
| VVV19 | 2-(tert-Butylsulfanyl)-4-methyl-7-(trifluoromethyl)-quinoline-3-carboxylic acid | VVV22 |
| VVV21 | 2-Ethylsulfanyl-4-methyl-quinoline-3-carboxylic acid | VVV22 |
| VVV23 | 2-Ethylsulfanyl-7-methoxy-4-methyl-quinoline-3-carboxylic acid | VVV22 |
| VVV24 | 2-Ethylsulfanyl-4,6-dimethyl-quinoline-3-carboxylic acid | VVV22 |
| VVV25 | 2-Ethylsulfanyl-4-methyl-7-(trifluoromethyloxy)-quinoline-3-carboxylic acid ethyl ester | VVV22 without section e) |
| VVV26 | 4-Ethyl-2-ethylsulfanyl-7-(trifluoromethyl)-quinoline-3-carboxylic acid | VVV08 |
| VVV27 | 2-Ethylsulfanyl-4-isopropyl-7-(trifluoromethyl)-quinoline-3-carboxylic acid | VVV08 |
| VVV28 | 2-Ethylsulfanyl-8-methoxy-4-methyl-quinoline-3-carboxylic acid ethyl ester | VVV22 without section e) |
| VVV29 | 2-Ethylsulfanyl-4-methyl-8-(trifluoromethyl)-quinoline-3-carboxylic acid ethyl ester | VVV22 without section e) |
| VVV31 | 2-Ethylsulfanyl-5-fluoro-4-methyl-quinoline-3-carboxylic acid | VVV30 |
| VVV32 | 2-Ethylsulfanyl-8-fluoro-4-methyl-quinoline-3-carboxylic acid | VVV30 |
| VVV33 | 2-Ethylsulfanyl-7-fluoro-4-methyl-quinoline-3-carboxylic acid | VVV22 |
| VVV34 | 2-Ethylsulfanyl-6-fluoro-4-methyl-quinoline-3-carboxylic acid | VVV22 |
| VVV35 | 2-Ethylsulfanyl-4,7-dimethyl-quinoline-3-carboxylic acid | VVV22 |
| VVV36 | 2-Ethylsulfanyl-5-methoxy-4-methyl-quinoline-3-carboxylic acid | VVV22 |
| VVV37 | 2-Ethylsulfanyl-6-methoxy-4-methyl-quinoline-3-carboxylic acid | VVV22 |
| VVV38 | 2-Ethylsulfanyl-4-methyl-6-(trifluoromethyl)-quinoline-3-carboxylic acid | VVV22 |
| VVV40 | 2-Ethylsulfanyl-4-methyl-7-morpholin-4-yl-quinoline-3-carboxylic acid | VVV39 + VVV22 section e) |

SYNTHESIS OF THE EXAMPLE COMPOUNDS

Synthesis of Example Compound 1

2-(Pentylthio)-N-(2-thienylmethyl)-3-quinoline carboxamide

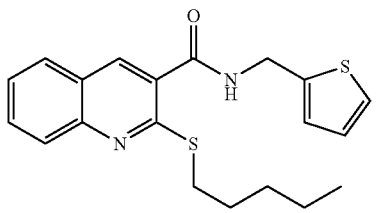 [SMILES: CCCCCSc1nc2ccccc2cc1C(=O)NCc1cccs1]

A solution of 300 mg (1.0 mmol) 2-mercapto-N-(thiophen-2-ylmethyl)quinoline-3-carboxamide (precursor VVV02) in DMF (2.3 ml) was mixed with 151 mg (1.1 mmol) $K_2CO_3$ at room temperature and stirred for 30 min. Then 131 µl (1.0 mmol) 1-iodopentane were added and the mixture was stirred for a further 3 days at RT. Then the mixture was concentrated to small volume under vacuum and the residue was taken up with EE and washed with water. The aqueous phase was extracted with EE and the combined organic phases were dried over $MgSO_4$, filtered and concentrated to small volume under vacuum. Crystallisation of the residue from EE yielded 146 mg (0.4 mmol, 39%) 2-(pentylthio)-N-(2-thienylmethyl)-3-quinoline carboxamide. MS: m/z 371.1 [M+H]$^+$.

Synthesis of Example Compound 2

3-{[3-[Oxo-(2-thienylmethylamino)methyl]-2-quinolyl]thio}propanoic acid methyl ester

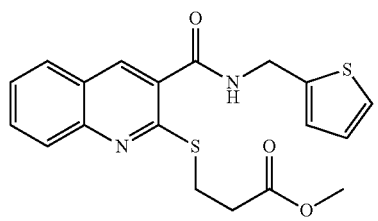 [SMILES: COC(=O)CCSc1nc2ccccc2cc1C(=O)NCc1cccs1]

A solution of 361 mg (3.0 mmol) 3-mercaptopropionic acid methyl ester in DMF (18 ml) was cooled to 0° C. and mixed with 336.6 mg (3.0 mmol) potassium tert-butylate and stirred for 10 min. Then 908 mg (3.0 mmol) 2-chloro-N-(thiophen-2-ylmethyl)quinoline-3-carboxamide (precursor VVV01) were added and the reaction solution was then heated slowly to 50° C. and stirred for 16 h at this temperature. It was then diluted with EE and washed with a saturated aqueous $NH_4Cl$ solution. The aqueous phase was extracted with EE. The combined organic phases were washed with water and brine, dried over $Na_2SO_4$, filtered and concentrated to small volume under vacuum. Column chromatography (hexane/EE 4:1) with the residue yielded 614 mg (1.6 mmol, 53%) 3-[[3-[oxo-(2-thienylmethylamino)methyl]-2-quinolyl]thio]propanoic acid methyl ester. MS: m/z 387.1 [M+H]$^+$.

Synthesis of Example Compound 5

2-[2-(Phenylsulfonyl)ethylthio]-N-(2-thienyl-methyl)-3-quinoline carboxamide

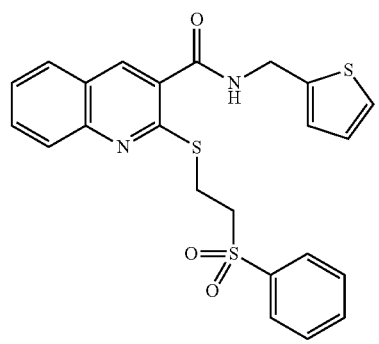 [SMILES: O=C(NCc1cccs1)c1cc2ccccc2nc1SCCS(=O)(=O)c1ccccc1]

112 mg (1.0 mmol) potassium tert-butylate were added to a solution of 202 mg (1.0 mmol) 2-(phenylsulfonyl)ethanethiol in DMF (6 ml) at 0° C. and the mixture was stirred for 10 min at 0° C. Then 303 mg (1.0 mmol) 2-chloro-N-(thiophen-2-ylmethyl)quinoline-3-carboxamide (precursor VVV01) were added at 0° C. and the reaction solution was heated slowly to 50° C. and stirred for 16 h at this temperature. After cooling to RT it was diluted with EE and washed with a saturated aqueous $NH_4Cl$ solution. The aqueous phase was extracted with EE. The combined organic phases were washed with water and brine, dried over $Na_2SO_4$, filtered and concentrated to small volume under vacuum. Column chromatography (hexane/EE 4:1) with the residue yielded 326 mg (0.7 mmol, 70%) 2-[2-(phenylsulfonyl)ethylthio]-N-(2-thienyl-methyl)-3-quinoline carboxamide. MS: m/z 469.1 [M+H]$^+$.

Synthesis of Example Compound 7

2-(Ethylthio)-N-(2-thienylmethyl)-3-quinoline carboxamide

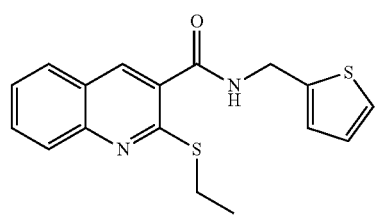 [SMILES: CCSc1nc2ccccc2cc1C(=O)NCc1cccs1]

A solution of 303 mg (1.0 mmol) 2-chloro-N-(thiophen-2-ylmethyl)quinoline-3-carboxamide (precursor VVV01) in ethanol (10 ml) was mixed with 92 mg (1.1 mmol) sodium thioethanolate and refluxed for 90 min. Then it was poured onto water and extracted repeatedly with EE. The combined organic phases were dried over $MgSO_4$, filtered and concentrated to small volume under vacuum. Crystallisation (EE/ hexane) of the residue yielded 103 mg (0.3 mmol, 31%) 2-(ethylthio)-N-(2-thienylmethyl)-3-quinoline carboxamide. MS: m/z 329.1 [M+H]⁺.

Synthesis of Example Compound 8

2-[2-(Phenylsulfonyl)ethylthio]-N-(2-thienyl-methyl)-6-(trifluoromethyl)-3-quinoline carboxamide

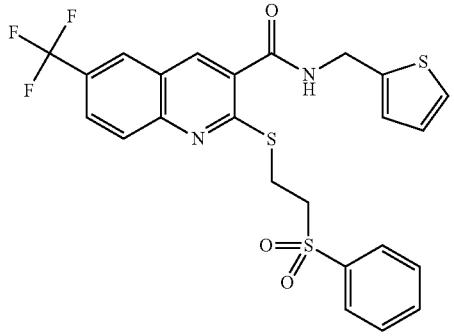 [SMILES: O=C(NCc1cccs1)c1cc2cc(C(F)(F)F)ccc2nc1SCCS(=O)(=O)c1ccccc1]

A solution of 441 mg (1.0 mmol) 2-(2-(phenylsulfonyl)ethylthio)-6-(trifluoromethyl)-quinoline-3-carboxylic acid (precursor VVV04) in DMF (5 ml) was mixed with 456 mg (1.2 mmol) HATU and 680 µl (4.0 mmol) DIPEA and stirred for 15 h at RT. Then it was diluted with EE and washed with a saturated aqueous NH₄Cl solution, a saturated aqueous NaHCO₃ solution and brine. The organic phase was dried over Na₂SO₄, filtered and concentrated to small volume under vacuum. Column chromatography (hexane/EE 7:3) of the residue yielded 107 mg (0.2 mmol, 20%) 2-[2-(phenylsulfonyl)ethylthio]-N-(2-thienylmethyl)-6-(trifluoromethyl)-3-quinoline carboxamide. MS: m/z 537.1 [M+H]⁺.

Synthesis of Example Compound 11

2-(Pentylthio)-N-(2-thienylmethyl)-6-(trifluoromethyl)-3-quinoline carboxamide

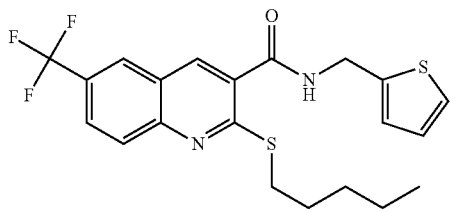 [SMILES: CCCCCSc1nc2ccc(C(F)(F)F)cc2cc1C(=O)NCc1cccs1]

198 mg (8.6 mmol) sodium were added slowly to MeOH (86 ml) and the solution was stirred for 5 min at RT. Then a solution of 455 mg (1.0 mmol) 3-(3-(thiophen-2-ylmethylcarbamoyl)-6-(trifluoromethyl)quinolin-2-ylthio)propanoic acid methyl ester (Example 26) in MeOH (10 ml) was added at RT. The reaction solution was then heated for 30 min at 70° C. Then 396 µl (3.0 mmol) 1-iodopentane were added at RT and the mixture was stirred for 1 h at RT. Then the mixture was concentrated to small volume under vacuum and the residue was taken up with EE. It was washed with water and brine and the organic phase was dried over Na₂SO₄, filtered and concentrated to small volume under vacuum. 167 mg (0.4 mmol, 38%) 2-(pentylthio)-N-(2-thienylmethyl)-6-(trifluoromethyl)-3-quinoline carboxamide were obtained as residue. MS: m/z 439.1 [M+H]⁺.

Synthesis of Example Compound 13

N-(2-Thienylmethyl)-2-[2-[3-(trifluoromethyl)-phenyl]sulfonylethylthio]-3-quinoline carboxamide

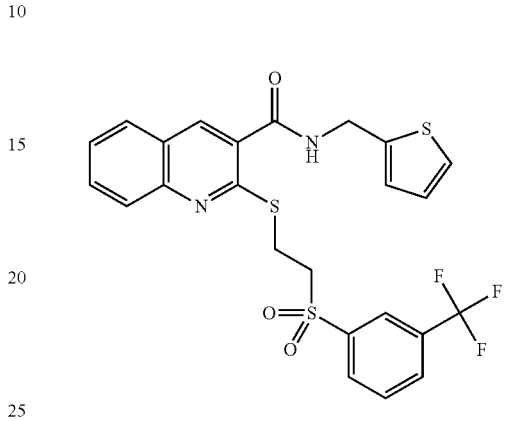

151 mg (1.1 mmol) K₂CO₃ and 300 mg (1.1 mmol) 1-(2-chloroethylsulfonyl)-3-(trifluoromethyl)benzene were added to a solution of 300 mg (1.0 mmol) 2-mercapto-N-(thiophen-2-ylmethyl)quinoline-3-carboxamide (precursor VVV02) in acetone (10 ml) at RT and the mixture was heated for 3 h at 70° C. Then it was filtered and the filtrate was concentrated to small volume under vacuum. The residue was taken up with EE and washed with water and brine, dried over MgSO₄, filtered and concentrated to small volume under vacuum. Column chromatography (DCM/EE 20:1) of the residue yielded 163 mg (0.3 mmol, 30%) N-(2-thienylmethyl)-2-[2-[3-(trifluoromethyl)-phenyl]sulfonylethylthio]-3-quinoline carboxamide. MS: m/z 537.1 [M+H]⁺.

Synthesis of Example Compound 30

2-Ethylsulfanyl-4-methyl-N-(thiophen-2-yl-methyl)-7-(trifluoromethyl)-quinoline-3-carboxamide

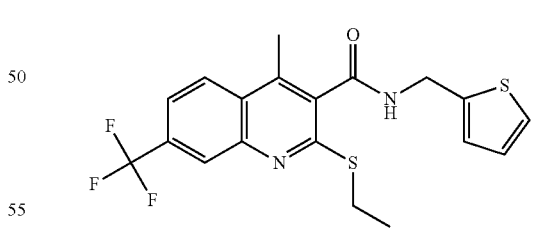

134 µl (1.3 mmol) thiophenemethanamine, 438 mg (1.1 mmol) HATU and 420 µl (3.0 mmol) NEt₃ were added in succession to a solution of 330 mg (1.05 mmol) 2-(ethylthio)-4-methyl-7-(trifluoromethyl)quinoline-3-carboxylic acid (VVV08) in THF (8 ml) and the mixture was then heated for 24 h at 50° C. Then it was diluted with EE and washed with a 4M aqueous NH₄Cl solution, a 1M aqueous Na₂CO₃ solution and brine. The organic phase was dried over MgSO₄ and then filtered through a silica layer. Column chromatography (hexane/EE 7:3) of the residue yielded 277 mg (0.67 mmol, 65%)

2-ethylsulfanyl-4-methyl-N-(thiophen-2-yl-methyl)-7-(trifluoromethyl)-quinoline-3-carboxamide. MS: m/z 411.1 [M+H]⁺.

Synthesis of Example Compound 46

N-[(3-Fluorophenyl)-methyl]-4-methyl-2-(propylsulfanyl)-7-(trifluoromethyl)-quinoline-3-carboxamide

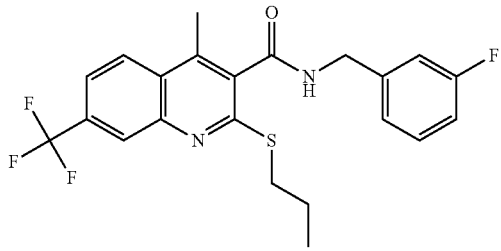 [SMILES: CCCSc1nc2cc(C(F)(F)F)ccc2c(C)c1C(=O)NCc1cccc(F)c1]

209 mg (1.5 mmol) K₂CO₃ and 137 µl (1.5 mmol) propanethiol were added to a solution of 200 mg (0.5 mmol) 2-chloro-N-[(3-fluorophenyl)-methyl]-4-methyl-7-(trifluoromethyl)-quinoline-3-carboxamide (VVV17) in DMF (4 ml) and the mixture was heated in a closed vessel for 72 h at 40° C. After cooling to RT the mixture was diluted with water and extracted with EE. The organic phase was washed with water and brine, dried over MgSO₄, filtered and concentrated to small volume under vacuum. Column chromatography (hexane/EE 3:1) of the residue yielded 146 mg (0.33 mmol, 67%) N-[(3-fluorophenyl)-methyl]-4-methyl-2-(propylsulfanyl)-7-(trifluoromethyl)-quinoline-3-carboxamide. MS: m/z 437.1 [M+H]⁺.

Synthesis of Example Compound 112

2-Ethylsulfanyl-N-[(2-hydroxyphenyl)-methyl]-4-methyl-7-(trifluoromethyl)-quinoline-3-carboxamide

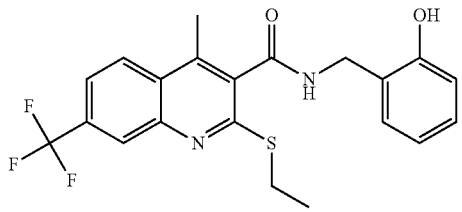 [SMILES: CCSc1nc2cc(C(F)(F)F)ccc2c(C)c1C(=O)NCc1ccccc1O]

A solution of 350 mg (0.8 mmol) 2-ethylsulfanyl-N-[(2-methoxyphenyl)-methyl]-4-methyl-7-(trifluoromethyl)-quinoline-3-carboxamide (example 84) in DCM (10 ml) was cooled to 0° C. 500 µl (4.9 mmol) boron tribromide were added dropwise at this temperature. The mixture was then stirred for 90 min at room temperature. Then it was diluted with water and extracted with DCM. The organic phase was washed with water and brine, dried over Na₂SO₄, filtered and concentrated to small volume under vacuum. Column chromatography (hexane/EE 4:1) of the residue yielded 240 mg (0.57 mmol, 70%) 2-ethylsulfanyl-N-[(2-hydroxyphenyl)-methyl]-4-methyl-7-(trifluoromethyl)-quinoline-3-carboxamide. MS: m/z 421.1 [M+H]⁺.

Synthesis of Example Compound 122

4-Chloro-2-ethylsulfanyl-N-[(3-fluorophenyl)-methyl]-7-(trifluoromethyl)-quinoline-3-carboxamide

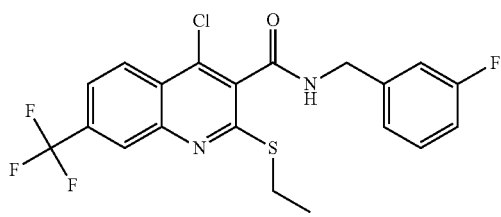 [SMILES: CCSc1nc2cc(C(F)(F)F)ccc2c(Cl)c1C(=O)NCc1cccc(F)c1]

A mixture of 1.0 g (2.36 mmol) 2-(ethylthio)-N-(3-fluorobenzyl)-4-hydroxy-7-(trifluoromethyl)quinoline-3-carboxamide and POCl₃ (10 ml) was heated for 2 h at 130° C. After cooling to RT the mixture was adjusted to pH ~8 with a saturated aqueous NaHCO₃ solution and extracted with EE. The organic phase was washed with water and brine, dried over Na₂SO₄, filtered and concentrated to small volume under vacuum. Column chromatography (hexane/EE 22:3) of the residue yielded 0.5 g (1.1 mmol, 48%) 4-chloro-2-ethylsulfanyl-N-[(3-fluorophenyl)-methyl]-7-(trifluoromethyl)-quinoline-3-carboxamide. MS: m/z 443.1 [M+H]⁺.

Synthesis of Example Compound 130

2-Ethylsulfanyl-N-[(3-fluorophenyl)-methyl]-4-methoxy-7-(trifluoromethyl)-quinoline-3-carboxamide

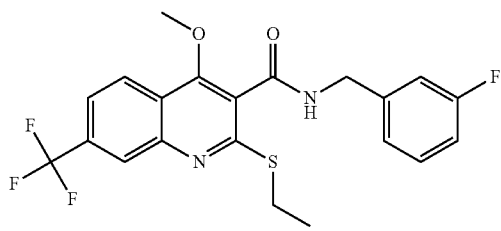 [SMILES: CCSc1nc2cc(C(F)(F)F)ccc2c(OC)c1C(=O)NCc1cccc(F)c1]

20 mg (0.95 mmol) sodium were added to methanol (6 ml) at RT. Once the sodium had completely dissolved, a solution of 210 mg (0.47 mmol) 4-chloro-2-ethylsulfanyl-N-[(3-fluorophenyl)-methyl]-7-(trifluoromethyl)-quinoline-3-carboxamide (example 122) in MeOH (2 ml) was added at RT. The mixture was then heated for 30 min at 60° C. Then the mixture was concentrated to small volume under vacuum and the residue was taken up with water and extracted with EE. The organic phase was washed with water and brine, dried over Na₂SO₄, filtered and concentrated to small volume under vacuum. Column chromatography (hexane/EE 9:1) of the residue yielded 80 mg (0.18 mmol, 38%) 2-ethylsulfanyl- N-[(3-fluorophenyl)-methyl]-4-methoxy-7-(trifluoromethyl)-quinoline-3-carboxamide. MS: m/z 439.1 [M+H]⁺.

Synthesis of Example Compound 131

4-Dimethylamino-2-ethylsulfanyl-N-[(3-fluorophenyl)-methyl]-7-(trifluoromethyl)-quinoline-3-carboxamide

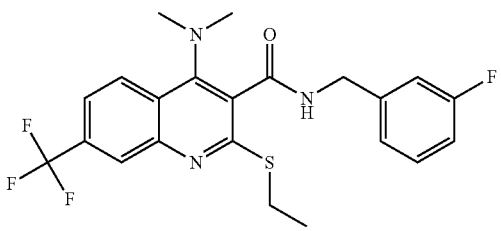 [SMILES: CCSc1nc2cc(C(F)(F)F)ccc2c(N(C)C)c1C(=O)NCc1cccc(F)c1]

60 mg (0.45 mmol) K$_2$CO$_3$ and 0.7 ml (1.36 mmol, 2M in THF) dimethylamine were added at RT to a solution of 200 mg (0.45 mmol) 4-chloro-2-ethylsulfanyl-N-[(3-fluorophenyl)-methyl]-7-(trifluoromethyl)-quinoline-3-carboxamide (example 122) in DMF (3 ml) and the mixture was then heated in a closed vessel for 150 min at 80°. Then it was diluted with water and extracted with EE. The organic phase was washed with water and brine, dried over Na$_2$SO$_4$, filtered and concentrated to small volume under vacuum. Column chromatography (hexane/EE 17:3) of the residue yielded 120 mg (0.27 mmol, 60%) 4-dimethylamino-2-ethylsulfanyl-N-[(3-fluorophenyl)-methyl]-7-(trifluoromethyl)-quinoline-3-carboxamide. MS: m/z 452.1 [M+H]⁺.

Synthesis of Example Compound 132

2-Ethylsulfanyl-N-[(4-fluorophenyl)-methyl]-4-methyl-7-(trifluoromethyloxy)-quinoline-3-carboxamide

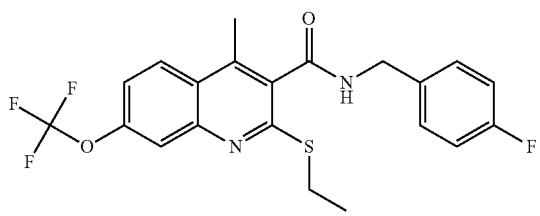 [SMILES: CCSc1nc2cc(OC(F)(F)F)ccc2c(C)c1C(=O)NCc1ccc(F)cc1]

1.12 ml (2.24 mmol, 2M in toluene)trimethyl aluminium and 260 μl (2.24 mmol) 4-fluorobenzylamine were added in succession to a solution of 200 mg (0.56 mmol) 2-ethylsulfanyl-4-methyl-7-(trifluoromethyloxy)-quinoline-3-carboxylic acid ethyl ester (VVV25) in toluene (7 ml) and the mixture was then heated for 3 h at 90° C. Then it was diluted with 0.5M hydrochloric acid and extracted with EE. The organic phase was washed with water and brine, dried over Na$_2$SO$_4$, filtered and concentrated to small volume under vacuum. Column chromatography (hexane/DCM 3:2) of the residue yielded 150 mg (0.34 mmol, 61%) 2-ethylsulfanyl-N-[(4-fluorophenyl)-methyl]-4-methyl-7-(trifluoromethyloxy)-quinoline-3-carboxamide. MS: m/z 439.1 [M+H]⁺.

Synthesis of Further Example Compounds

The synthesis of further example compounds took place by the methods already described. Table 2 shows which compound was prepared by which method. The starting materials and reagents used in each case are apparent to the person skilled in the art.

TABLE 2

| Example | Chemical name | Preparation analogous to example | MS m/z [M + H]⁺ |
|---|---|---|---|
| 3 | 2-(3-Cyclohexyl-propylsulfanyl)-N-(thiophen-2-yl-methyl)-quinoline-3-carboxamide | 1 | 425.2 |
| 4 | 2-(3-Phenyl-propylsulfanyl)-N-(thiophen-2-yl-methyl)-quinoline-3-carboxamide | 1 | 419.1 |
| 6 | 2-[3-(4-Fluorophenyl)-propylsulfanyl]-N-(thiophen-2-yl-methyl)-quinoline-3-carboxamide | 13 | 437.1 |
| 9 | 2-[2-(Benzenesulfonyl)-ethylsulfanyl]-N-(thiophen-2-yl-methyl)-7-(trifluoromethyl)-quinoline-3-carboxamide | 5 | 537.1 |
| 10 | 2-[2-(Benzenesulfonyl)-ethylsulfanyl]-N-(thiophen-2-yl-methyl)-5-(trifluoromethyl)-quinoline-3-carboxamide | 5 | 537.1 |
| 12 | 2-Ethylsulfanyl-N-(thiophen-2-yl-methyl)-6-(trifluoromethyl)-quinoline-3-carboxamide | 11 | 397.1 |
| 14 | 2-Ethylsulfanyl-N-(thiophen-2-yl-methyl)-7-(trifluoromethyl)-quinoline-3-carboxamide | 11 | 397.1 |
| 15 | 2-(Pentylsulfanyl)-N-(thiophen-2-yl-methyl)-7-(trifluoromethyl)-quinoline-3-carboxamide | 11 | 439.1 |
| 16 | 2-[2-[(4-Fluorophenyl)sulfonyl]-ethylsulfanyl]-N-(thiophen-2-yl-methyl)-quinoline-3-carboxamide | 13 | 487.1 |
| 17 | 2-[2-(p-Tolylsulfonyl)-ethylsulfanyl]-N-(thiophen-2-yl-methyl)-quinoline-3-carboxamide | 13 | 483.1 |
| 18 | 2-[2-(p-Tolylsulfanyl)-ethylsulfanyl]-N-(thiophen-2-yl-methyl)-quinoline-3-carboxamide | 13 | 451.1 |
| 19 | 2-[2-(Benzenesulfonyl)-ethylsulfanyl]-N-(cyclohexylmethyl)-quinoline-3-carboxamide | 5 | 469.2 |
| 20 | 2-[3-(p-Tolyl)-propylsulfanyl]-N-(thiophen-2-yl-methyl)-quinoline-3-carboxamide | 13 | 433.1 |
| 21 | 2-(2-Phenylsulfanyl-ethylsulfanyl)-N-(thiophen-2-yl-methyl)-quinoline-3-carboxamide | 13 | 437.1 |
| 22 | 2-[2-(Benzenesulfonyl)-ethylsulfanyl]-N-(2-cyclohexylethyl)-quinoline-3-carboxamide | 5 | 483.2 |
| 23 | 2-[2-(Benzenesulfonyl)-ethylsulfanyl]-N-(3,3-dimethylbutyl)-quinoline-3-carboxamide | 5 | 457.2 |
| 24 | 2-[2-[(4-Fluorophenyl)sulfanyl]-ethylsulfanyl]-N-(thiophen-2-yl-methyl)-quinoline-3-carboxamide | 13 | 455.1 |
| 25 | N-(3,3-Dimethylbutyl)-2-ethylsulfanyl-4-methyl-7-(trifluoromethyl)-quinoline-3-carboxamide | 8 | 399.2 |
| 26 | 3-[[3-(Thiophen-2-yl-methyl-carbamoyl)-6-(trifluoromethyl)-quinolin-2-yl]sulfanyl]-propionic acid methyl ester | 8 | 455.1 |
| 27 | 3-[[3-(Thiophen-2-yl-methyl-carbamoyl)-7-(trifluoromethyl)-quinolin-2-yl]sulfanyl]-propionic acid methyl ester | 2 | 455.1 |
| 28 | N-(2,2-Dimethylpropyl)-2-ethylsulfanyl-4-methyl-7-(trifluoromethyl)-quinoline-3-carboxamide | 30 | 385.1 |
| 29 | N-(Cycloheptylmethyl)-2-ethylsulfanyl-4-methyl-7-(trifluoromethyl)-quinoline-3-carboxamide | 30 | 425.2 |

TABLE 2-continued

| Example | Chemical name | Preparation analogous to example | MS m/z [M + H]+ |
|---|---|---|---|
| 31 | N-[(3,4-Difluorophenyl)-methyl]-2-ethylsulfanyl-4-methyl-7-(trifluoromethyl)-quinoline-3-carboxamide | 30 | 441.1 |
| 32 | N-[(2,4-Difluorophenyl)-methyl]-2-ethylsulfanyl-4-methyl-7-(trifluoromethyl)-quinoline-3-carboxamide | 30 | 441.1 |
| 33 | 2-Ethylsulfanyl-4-methyl-7-(trifluoromethyl)-N-[(3,4,5-trifluorophenyl)-methyl]-quinoline-3-carboxamide | 30 | 459.1 |
| 34 | 2-Ethylsulfanyl-4-methyl-7-(trifluoromethyl)-N-[(2,4,5-trifluorophenyl)-methyl]-quinoline-3-carboxamide | 30 | 459.1 |
| 35 | 2-Ethylsulfanyl-4-methyl-N-(pyridin-4-yl-methyl)-7-(trifluoromethyl)-quinoline-3-carboxamide | 30 | 406.1 |
| 36 | N-[(4-tert-Butylphenyl)-methyl]-2-ethylsulfanyl-4-methyl-7-(trifluoromethyl)-quinoline-3-carboxamide | 30 | 461.2 |
| 37 | 2-Ethylsulfanyl-4-methyl-N-(3-methylbutyl)-7-(trifluoromethyl)-quinoline-3-carboxamide | 30 | 385.1 |
| 38 | 2-Ethylsulfanyl-4-methyl-7-(trifluoromethyl)-N-[[3-(trifluoromethyl)phenyl]-methyl]-quinoline-3-carboxamide | 30 | 473.1 |
| 39 | 2-Ethylsulfanyl-4-methyl-N-phenethyl-7-(trifluoromethyl)-quinoline-3-carboxamide | 30 | 419.1 |
| 40 | 2-Ethylsulfanyl-4-methyl-N-(3-phenylpropyl)-7-(trifluoromethyl)-quinoline-3-carboxamide | 30 | 433.1 |
| 41 | 2-Ethylsulfanyl-4-methyl-N-(pyridin-2-yl-methyl)-7-(trifluoromethyl)-quinoline-3-carboxamide | 30 | 406.1 |
| 42 | 2-Ethylsulfanyl-4-methyl-N-(pyridin-3-yl-methyl)-7-(trifluoromethyl)-quinoline-3-carboxamide | 30 | 406.1 |
| 43 | 2-Ethylsulfanyl-4-methyl-N-(naphthalen-2-yl-methyl)-7-(trifluoromethyl)-quinoline-3-carboxamide | 30 | 455.1 |
| 44 | 2-Ethylsulfanyl-4-methyl-N-(thiazol-2-yl-methyl)-7-(trifluoromethyl)-quinoline-3-carboxamide | 30 | 412.1 |
| 45 | 2-Ethylsulfanyl-4-methyl-N-([1,3,4]oxadiazol-2-yl-methyl)-7-(trifluoromethyl)-quinoline-3-carboxamide | 30 | 397.1 |
| 47 | N-[(3-Fluorophenyl)-methyl]-2-(isopropylsulfanyl)-4-methyl-7-(trifluoromethyl)-quinoline-3-carboxamide | 46 | 437.1 |
| 48 | 2-(Cyclopentylsulfanyl)-N-[(3-fluorophenyl)-methyl]-4-methyl-7-(trifluoromethyl)-quinoline-3-carboxamide | 46 | 463.1 |
| 49 | 2-(Butylsulfanyl)-N-[(3-fluorophenyl)-methyl]-4-methyl-7-(trifluoromethyl)-quinoline-3-carboxamide | 46 | 451.1 |
| 50 | N-[(3-Fluorophenyl)-methyl]-4-methyl-2-(pentylsulfanyl)-7-(trifluoromethyl)-quinoline-3-carboxamide | 46 | 465.2 |
| 51 | N-[(3-Fluorophenyl)-methyl]-4-methyl-2-(1-methyl-propylsulfanyl)-7-(trifluoromethyl)-quinoline-3-carboxamide | 46 | 451.1 |
| 52 | 2-(Cyclohexylsulfanyl)-N-[(3-fluorophenyl)-methyl]-4-methyl-7-(trifluoromethyl)-quinoline-3-carboxamide | 46 | 477.2 |
| 53 | N-(2-Cyclopentylethyl)-2-ethylsulfanyl-4-methyl-7-(trifluoromethyl)-quinoline-3-carboxamide | 30 | 411.2 |
| 54 | N-(3-Cyclopentylpropyl)-2-ethylsulfanyl-4-methyl-7-(trifluoromethyl)-quinoline-3-carboxamide | 30 | 425.2 |
| 55 | 2-Ethylsulfanyl-4-methyl-7-(trifluoromethyl)-N-[[4-(trifluoromethyl)phenyl]-methyl]-quinoline-3-carboxamide | 30 | 473.1 |
| 56 | N-[(3-tert-Butylphenyl)-methyl]-2-ethylsulfanyl-4-methyl-7-(trifluoromethyl)-quinoline-3-carboxamide | 30 | 461.2 |
| 57 | 2-Ethylsulfanyl-4-methyl-N-(4-methylpentyl)-7-(trifluoromethyl)-quinoline-3-carboxamide | 30 | 399.2 |
| 58 | 2-Benzylsulfanyl-N-[(3-fluorophenyl)-methyl]-4-methyl-7-(trifluoromethyl)-quinoline-3-carboxamide | 46 | 485.1 |
| 59 | 2-Ethylsulfanyl-N-[(3-fluoro-2-methoxyphenyl)-methyl]-4-methyl-7-(trifluoromethyl)-quinoline-3-carboxamide | 30 | 453.1 |
| 60 | 2-Ethylsulfanyl-N-[(5-fluoro-2-methoxyphenyl)-methyl]-4-methyl-7-(trifluoromethyl)-quinoline-3-carboxamide | 30 | 453.1 |
| 61 | N-[(3,4-Dimethylphenyl)-methyl]-2-ethylsulfanyl-4-methyl-7-(trifluoromethyl)-quinoline-3-carboxamide | 30 | 433.1 |
| 62 | 2-Ethylsulfanyl-4-methyl-7-(trifluoromethyl)-N-[[4-(trifluoromethylsulfanyl)-phenyl]-methyl]-quinoline-3-carboxamide | 30 | 505.1 |
| 63 | N-(Cyclohexylmethyl)-2-ethylsulfanyl-4-methyl-7-(trifluoromethyl)-quinoline-3-carboxamide | 30 | 411.2 |
| 64 | 2-Ethylsulfanyl-4-methyl-N-(tetrahydropyran-2-yl-methyl)-7-(trifluoromethyl)-quinoline-3-carboxamide | 30 | 413.1 |
| 65 | 2-Ethylsulfanyl-4-methyl-N-propyl-7-(trifluoromethyl)-quinoline-3-carboxamide | 30 | 357.1 |
| 66 | N-Butyl-2-ethylsulfanyl-4-methyl-7-(trifluoromethyl)-quinoline-3-carboxamide | 30 | 371.1 |
| 67 | 2-Ethylsulfanyl-N-(2-methoxyethyl)-4-methyl-7-(trifluoromethyl)-quinoline-3-carboxamide | 30 | 373.1 |
| 68 | 2-Ethylsulfanyl-4-methyl-N-pentyl-7-(trifluoromethyl)-quinoline-3-carboxamide | 30 | 385.1 |
| 69 | 2-Ethylsulfanyl-4-methyl-N-[(5-methylthiophen-2-yl)-methyl]-7-(trifluoromethyl)-quinoline-3-carboxamide | 30 | 425.1 |
| 70 | 2-Ethylsulfanyl-4-methyl-N-[(4-methylthiophen-2-yl)-methyl]-7-(trifluoromethyl)-quinoline-3-carboxamide | 30 | 425.1 |
| 71 | N-[(5-Chlorothiophen-2-yl)-methyl]-2-ethylsulfanyl-4-methyl-7-(trifluoromethyl)-quinoline-3-carboxamide | 30 | 445 |
| 72 | 2-Ethylsulfanyl-4-methyl-N-(2-thiophen-2-yl-ethyl)-7-(trifluoromethyl)-quinoline-3-carboxamide | 30 | 425.1 |
| 73 | N-(5-Bicyclo[2.2.1]heptanylmethyl)-2-ethylsulfanyl-4-methyl-7-(trifluoromethyl)-quinoline-3-carboxamide | 30 | 423.2 |
| 74 | N-Benzyl-2-ethylsulfanyl-4-methyl-7-(trifluoromethyl)-quinoline-3-carboxamide | 30 | 405.1 |
| 75 | 2-Ethylsulfanyl-N-[(2-fluorophenyl)-methyl]-4-methyl-7-(trifluoromethyl)-quinoline-3-carboxamide | 30 | 423.1 |
| 76 | 2-Ethylsulfanyl-N-[(3-fluorophenyl)-methyl]-4-methyl-7-(trifluoromethyl)-quinoline-3-carboxamide | 30 | 423.1 |
| 77 | 2-Ethylsulfanyl-N-[(4-fluorophenyl)-methyl]-4-methyl-7-(trifluoromethyl)-quinoline-3-carboxamide | 30 | 423.1 |
| 78 | N-[(2-Chlorophenyl)-methyl]-2-ethylsulfanyl-4-methyl-7-(trifluoromethyl)-quinoline-3-carboxamide | 30 | 439.1 |
| 79 | N-[(3-Chlorophenyl)-methyl]-2-ethylsulfanyl-4-methyl-7-(trifluoromethyl)-quinoline-3-carboxamide | 30 | 439.1 |
| 80 | N-[(4-Chlorophenyl)-methyl]-2-ethylsulfanyl-4-methyl-7-(trifluoromethyl)-quinoline-3-carboxamide | 30 | 439.1 |
| 81 | 2-Ethylsulfanyl-4-methyl-N-(o-tolylmethyl)-7-(trifluoromethyl)-quinoline-3-carboxamide | 30 | 419.1 |
| 82 | 2-Ethylsulfanyl-4-methyl-N-(m-tolylmethyl)-7-(trifluoromethyl)-quinoline-3-carboxamide | 30 | 419.1 |

TABLE 2-continued

| Example | Chemical name | Preparation analogous to example | MS m/z [M + H]+ |
|---|---|---|---|
| 83 | 2-Ethylsulfanyl-4-methyl-N-(p-tolylmethyl)-7-(trifluoromethyl)-quinoline-3-carboxamide | 30 | 419.1 |
| 84 | 2-Ethylsulfanyl-N-[(2-methoxyphenyl)-methyl]-4-methyl-7-(trifluoromethyl)-quinoline-3-carboxamide | 30 | 435.1 |
| 85 | 2-Ethylsulfanyl-N-[(3-methoxyphenyl)-methyl]-4-methyl-7-(trifluoromethyl)-quinoline-3-carboxamide | 30 | 435.1 |
| 86 | 2-Ethylsulfanyl-N-[(4-methoxyphenyl)-methyl]-4-methyl-7-(trifluoromethyl)-quinoline-3-carboxamide | 30 | 435.1 |
| 87 | N-[(3,5-Difluorophenyl)-methyl]-2-ethylsulfanyl-4-methyl-7-(trifluoromethyl)-quinoline-3-carboxamide | 30 | 441.1 |
| 88 | 4-Methyl-2-methylsulfanyl-N-(thiophen-2-yl-methyl)-7-(trifluoromethyl)-quinoline-3-carboxamide | 30 | 397.1 |
| 89 | 2-(tert-Butylsulfanyl)-4-methyl-N-(thiophen-2-yl-methyl)-7-(trifluoromethyl)-quinoline-3-carboxamide | 30 | 439.1 |
| 90 | N-(2,2-Dimethylpropyl)-2-ethylsulfanyl-7-(trifluoromethyl)-quinoline-3-carboxamide | 30 | 371.1 |
| 91 | 2-Ethylsulfanyl-4-methyl-N-(thiophen-2-yl-methyl)-quinoline-3-carboxamide | 30 | 343.1 |
| 92 | 2-Ethylsulfanyl-N-[(3-fluorophenyl)-methyl]-4-methyl-quinoline-3-carboxamide | 30 | 355.1 |
| 93 | 2-(tert-Butylsulfanyl)-N-[(3-fluorophenyl)-methyl]-4-methyl-7-(trifluoromethyl)-quinoline-3-carboxamide | 30 | 451.1 |
| 94 | 2-(tert-Butylsulfanyl)-N-[(4-fluorophenyl)-methyl]-4-methyl-7-(trifluoromethyl)-quinoline-3-carboxamide | 30 | 451.1 |
| 95 | 7-tert-Butyl-2-ethylsulfanyl-N-[(3-fluorophenyl)-methyl]-4-methyl-quinoline-3-carboxamide | 30 | 411.2 |
| 96 | 7-tert-Butyl-2-ethylsulfanyl-N-[(4-fluorophenyl)-methyl]-4-methyl-quinoline-3-carboxamide | 30 | 411.2 |
| 97 | 2-Ethylsulfanyl-N-[(3-fluorophenyl)-methyl]-7-methoxy-4-methyl-quinoline-3-carboxamide | 30 | 385.1 |
| 98 | 2-Ethylsulfanyl-N-[(4-fluorophenyl)-methyl]-7-methoxy-4-methyl-quinoline-3-carboxamide | 30 | 385.1 |
| 99 | 2-Ethylsulfanyl-N-[(3-fluorophenyl)-methyl]-4,6-dimethyl-quinoline-3-carboxamide | 30 | 369.1 |
| 100 | 2-Ethylsulfanyl-N-[(4-fluorophenyl)-methyl]-4,6-dimethyl-quinoline-3-carboxamide | 30 | 369.1 |
| 101 | 2-Ethylsulfanyl-N-[(3-fluorophenyl)-methyl]-6-methoxy-4-methyl-quinoline-3-carboxamide | 30 | 385.1 |
| 102 | 2-Ethylsulfanyl-N-[(4-fluorophenyl)-methyl]-6-methoxy-4-methyl-quinoline-3-carboxamide | 30 | 385.1 |
| 103 | 2-Ethylsulfanyl-N-[(3-fluorophenyl)-methyl]-4-methyl-6-(trifluoromethyl)-quinoline-3-carboxamide | 30 | 423.1 |
| 104 | 2-Ethylsulfanyl-N-[(4-fluorophenyl)-methyl]-4-methyl-6-(trifluoromethyl)-quinoline-3-carboxamide | 30 | 423.1 |
| 105 | 2-Ethylsulfanyl-7-fluoro-N-[(3-fluorophenyl)-methyl]-4-methyl-quinoline-3-carboxamide | 30 | 373.1 |
| 106 | 2-Ethylsulfanyl-7-fluoro-N-[(4-fluorophenyl)-methyl]-4-methyl-quinoline-3-carboxamide | 30 | 373.1 |
| 107 | 2-Ethylsulfanyl-N-[(3-fluorophenyl)-methyl]-4,7-dimethyl-quinoline-3-carboxamide | 30 | 369.1 |
| 108 | 2-Ethylsulfanyl-N-[(4-fluorophenyl)-methyl]-4,7-dimethyl-quinoline-3-carboxamide | 30 | 369.1 |
| 109 | 2-Ethylsulfanyl-6,7-difluoro-N-[(4-fluorophenyl)-methyl]-4-methyl-quinoline-3-carboxamide | 30 | 391.1 |
| 110 | 2-Ethylsulfanyl-N-(furan-2-yl-methyl)-4-methyl-7-(trifluoromethyl)-quinoline-3-carboxamide | 30 | 395.1 |
| 111 | 2-Ethylsulfanyl-4-methyl-N-[(5-methyl-furan-2-yl)-methyl]-7-(trifluoromethyl)-quinoline-3-carboxamide | 30 | 409.1 |
| 113 | 2-Ethylsulfanyl-N-[(3-hydroxyphenyl)-methyl]-4-methyl-7-(trifluoromethyl)-quinoline-3-carboxamide | 112 | 421.1 |
| 114 | N-[(3-Fluorophenyl)-methyl]-4-methyl-2-methylsulfanyl-7-(trifluoromethyl)-quinoline-3-carboxamide | 30 | 409.1 |
| 115 | N-[(4-Fluorophenyl)-methyl]-4-methyl-2-methylsulfanyl-7-(trifluoromethyl)-quinoline-3-carboxamide | 30 | 409.1 |
| 116 | 2-Ethylsulfanyl-6-fluoro-N-[(3-fluorophenyl)-methyl]-4-methyl-quinoline-3-carboxamide | 30 | 373.1 |
| 117 | 2-Ethylsulfanyl-6-fluoro-N-[(4-fluorophenyl)-methyl]-4-methyl-quinoline-3-carboxamide | 30 | 373.1 |
| 118 | 2-Ethylsulfanyl-6,7-difluoro-N-[(3-fluorophenyl)-methyl]-4-methyl-quinoline-3-carboxamide | 30 | 391.1 |
| 119 | 2-Ethylsulfanyl-N-[(4-hydroxyphenyl)-methyl]-4-methyl-7-(trifluoromethyl)-quinoline-3-carboxamide | 112 | 421.1 |
| 120 | 2-Ethylsulfanyl-8-fluoro-N-[(3-fluorophenyl)-methyl]-4-methyl-quinoline-3-carboxamide | 30 | 373.1 |
| 121 | 2-Ethylsulfanyl-8-fluoro-N-[(4-fluorophenyl)-methyl]-4-methyl-quinoline-3-carboxamide | 30 | 373.1 |
| 123 | 2-Ethylsulfanyl-5-fluoro-N-[(3-fluorophenyl)-methyl]-4-methyl-quinoline-3-carboxamide | 30 | 373.1 |
| 124 | 2-Ethylsulfanyl-5-fluoro-N-[(4-fluorophenyl)-methyl]-4-methyl-quinoline-3-carboxamide | 30 | 373.1 |
| 125 | 2-Ethylsulfanyl-N-[(3-fluorophenyl)-methyl]-5-methoxy-4-methyl-quinoline-3-carboxamide | 30 | 385.1 |
| 126 | 2-Ethylsulfanyl-N-[(4-fluorophenyl)-methyl]-5-methoxy-4-methyl-quinoline-3-carboxamide | 30 | 385.1 |
| 127 | 2-Ethylsulfanyl-N-[(3-fluorophenyl)-methyl]-5-hydroxy-4-methyl-quinoline-3-carboxamide | 112 | 371.1 |
| 128 | 2-Ethylsulfanyl-N-[(3-fluorophenyl)-methyl]-6-hydroxy-4-methyl-quinoline-3-carboxamide | 112 | 371.1 |
| 129 | 2-Ethylsulfanyl-N-[(3-fluorophenyl)-methyl]-7-hydroxy-4-methyl-quinoline-3-carboxamide | 112 | 371.1 |
| 133 | 7-Dimethylamino-2-ethylsulfanyl-N-[(4-fluorophenyl)-methyl]-4-methyl-quinoline-3-carboxamide | 132 | 398.2 |
| 134 | 2-Ethylsulfanyl-N-[(3-fluorophenyl)-methyl]-4-methyl-7-morpholin-4-yl-quinoline-3-carboxamide | 30 | 440.2 |
| 135 | 2-Ethylsulfanyl-N-[(4-fluorophenyl)-methyl]-4-methyl-7-morpholin-4-yl-quinoline-3-carboxamide | 30 | 440.2 |
| 136 | 2-Ethylsulfanyl-N-[(3-fluorophenyl)-methyl]-4-methyl-8-(trifluoromethyl)-quinoline-3-carboxamide | 132 | 423.1 |
| 137 | 2-Ethylsulfanyl-N-[(4-fluorophenyl)-methyl]-4-methyl-8-(trifluoromethyl)-quinoline-3-carboxamide | 132 | 423.1 |
| 138 | 2-Ethylsulfanyl-N-[(3-fluorophenyl)-methyl]-8-methoxy-4-methyl-quinoline-3-carboxamide | 132 | 385.1 |

TABLE 2-continued

| Example | Chemical name | Preparation analogous to example | MS m/z [M + H]+ |
|---|---|---|---|
| 139 | 2-Ethylsulfanyl-N-[(4-fluorophenyl)-methyl]-8-methoxy-4-methyl-quinoline-3-carboxamide | 132 | 385.1 |
| 140 | 2-Ethylsulfanyl-N-[(3-fluorophenyl)-methyl]-8-hydroxy-4-methyl-quinoline-3-carboxamide | 112 | 371.1 |
| 141 | 7-Dimethylamino-2-ethylsulfanyl-N-[(3-fluorophenyl)-methyl]-4-methyl-quinoline-3-carboxamide | 132 | 398.2 |
| 142 | 2-Ethylsulfanyl-N-[(3-fluorophenyl)-methyl]-4-methyl-7-(trifluoromethyloxy)-quinoline-3-carboxamide | 132 | 439.1 |
| 143 | 4-Ethyl-2-ethylsulfanyl-N-[(3-fluorophenyl)-methyl]-7-(trifluoromethyl)-quinoline-3-carboxamide | 30 | 437.1 |
| 144 | 2-Ethylsulfanyl-N-[(3-fluorophenyl)-methyl]-4-isopropyl-7-(trifluoromethyl)-quinoline-3-carboxamide | 30 | 451.1 |

Pharmacological Experiments
Fluorescence Assay Using a Voltage-Sensitive Dye

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% foetal calf serum (FCS) (Invitrogen, #10270-106, heat-inactivated) and the necessary selection antibiotics.

Before being seeded out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply 20,000 to 30,000 cells/well/100 µl of the described nutrient medium, depending on density optimisation for the individual cell line, to 96-well measuring plates of the Corning™ CellBIND™ type (flat clear-bottom black polystyrene microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ bulk format part R8123 for FLIPR, MDS Analytical Technologies™) is prepared by dissolving the contents of a vessel of *Membrane Potential Assay Kit Red Component A* in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with exclusion of light.

The fluorescence measurements are carried out with a BMG Labtech FLUOstar™, BMG Labtech NOVOstar™ or BMG Labtech POLARstar™ instrument (525 nm excitation, 560 nm emission, bottom-read mode). After incubation of the dye, 50 µl of the substances to be tested in the desired concentrations, or 50 µl of ES buffer for control purposes, are introduced into separate cavities of the measuring plate and incubated for 30 min at room temperature whilst being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has an agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_{2K} - F_{1K}}{F_{1K}}\right) \times 100 = \left(\frac{\Delta F}{F}\right)_K(\%)$$

A substance has an agonistic activity on the potassium channel if $$\frac{\Delta F}{F}$$

is greater than $$\left(\frac{\Delta F}{F}\right)_K : \frac{\Delta F}{F} \rangle \left(\frac{\Delta F}{F}\right)_K$$

Independently of the comparison of $$\frac{\Delta F}{F} \text{ with } \left(\frac{\Delta F}{F}\right)_K,$$

it is also possible to conclude that a target compound has an agonistic activity if an increase in $$\frac{\Delta F}{F}$$

is to be observed as the dosage of the target compound increases.

Calculations of $EC_{50}$ values are carried out with the aid of Prism v4.0 software (GraphPad Software™)

Low-Intensity Tail Flick in Rats

The antinociceptive activity of the test substance against an acute noxic thermal stimulant was examined in the tail-flick test in rats using the method described by D'Amour and Smith (J. Pharm. Exp. Ther. 72, 74 79 (1941)). Male Sprague-Dawley rats weighing between 200 and 250 g were used (breeder: Janvier, Le Genest St. Isle, France). The animals were placed in special test compartments and the base of the tail was exposed to a focused light beam from an analgesia meter (model 2011, Rhema Labortechnik, Hofheim, Germany). 10 animals were used per group. Before administering a substance according to the invention, the tail-flick latency (time from switching on the light beam to the flick of the tail) was measured twice at an interval of five minutes and the average was defined as the control latency time. The intensity of the light beam was chosen so that the control latency time was 7 to 9 seconds. The measurement of the tail-flick latency was then repeated 10, 20, 30 and 60 minutes after peroral administration of the substance. The antinociceptive action of the test substance was determined as the increase in the tail-flick latency time using the following formula:

$$MPE[\%] = [(T_1 T_0)/(T_2 - T_0)] \times 100$$

where $T_0$=control latency time before administration of the substance, $T_1$=latency time after administration of the substance, $T_2$=maximum exposure time to the light beam (30 seconds), MPE=maximum possible effect.

Analysis of variance (repeated measures ANOVA) was used to test for statistically significant differences between the substance and vehicle group. The significance level was set at 0.05.

Pharmacological Data

The results of the pharmacological models described above are summarised in Table 3.

TABLE 3

| Example compound | Fluorimetry EC50 [nM] | Fluorimetry % efficacy at 1 μM (50 μM retigabine = 100%) | Low-intensity tail flick rat p.o. % effect (dose [mg/kg]) |
|---|---|---|---|
| 1 | 744 | 143 | |
| 2 | | 26 | |
| 3 | 1931 | 77 | |
| 4 | 144 | 168 | |
| 5 | 2657 | 98 | |
| 6 | 1221 | 111 | |
| 7 | 1350 | | |
| 8 | | 46 | |
| 9 | | 26 | |
| 10 | | 9 | |
| 11 | | 41 | |
| 12 | 412 | 155 | |
| 13 | 991 | 136 | |
| 14 | 291 | 223 | 9 (21.5) |
| 15 | 778 | 145 | |
| 16 | 78 | 164 | |
| 17 | | 77 | |
| 18 | | 72 | |
| 19 | 167 | 71 | |
| 20 | | 64 | |
| 21 | 119 | 30 | |
| 22 | | 15 | |
| 23 | | 14 | |
| 24 | | 27 | |
| 25 | | 8 | |
| 28 | | 47 | |
| 29 | 367 | 86 | |
| 30 | 82 | 141 | 31 (10) |
| 31 | 145 | 159 | |
| 32 | 59 | 70 | |
| 33 | 140 | 162 | |
| 34 | 98 | 72 | |
| 35 | 2655 | 142 | |
| 36 | 136 | 93 | |
| 37 | 85 | 121 | 0 (10.0) |
| 38 | 76 | 142 | |
| 39 | 473 | 48 | |
| 40 | 194 | 152 | |
| 41 | 1105 | 121 | |
| 42 | 1690 | 175 | 51 (21.5) |
| 43 | 159 | 77 | |
| 44 | 587 | 169 | |
| 45 | | 23 | |
| 46 | 141 | 155 | |
| 47 | 73 | 152 | |
| 48 | 56 | 133 | |
| 49 | 74 | 151 | |
| 50 | 61 | 150 | |
| 51 | 37 | 158 | |
| 52 | 64 | 102 | |
| 53 | 256 | 73 | |
| 54 | 162 | 229 | |
| 55 | 149 | 167 | |
| 56 | 67 | 97 | |
| 57 | 150 | 205 | |
| 69 | 858 | 123 | |
| 70 | 1463 | 114 | |
| 71 | 305 | 163 | |
| 72 | 732 | 59 | |
| 73 | | 25 | |
| 74 | 163 | 128 | |
| 75 | 71 | 88 | |
| 76 | 92 | 182 | $ED_{50}$ 6.3 |
| 77 | 105 | 137 | 37 (10) |
| 78 | | 33 | |
| 79 | 124 | 116 | |
| 80 | 148 | 135 | |
| 81 | | 28 | |
| 82 | 219 | 108 | |
| 83 | 242 | 130 | |
| 84 | | 25 | |
| 85 | 413 | 89 | |
| 86 | 565 | 108 | |
| 87 | 144 | 159 | |
| 88 | 212 | 154 | |
| 89 | 64 | 220 | $ED_{50}$ 2.7 |
| 90 | 842 | 53 | |
| 91 | 1213 | 50 | |
| 92 | 950 | 65 | |
| 93 | 88 | 157 | |
| 94 | 54 | 162 | 71 (4.64) |
| 95 | 627 | 96 | |
| 96 | 808 | 101 | |
| 97 | 622 | 60 | |

TABLE 3-continued

| Example compound | Fluorimetry EC50 [nM] | Fluorimetry % efficacy at 1 μM (50 μM retigabine = 100%) | Low-intensity tail flick rat p.o. % effect (dose [mg/kg]) |
|---|---|---|---|
| 98 | 404 | 70 | |
| 99 | 623 | 90 | |
| 100 | 337 | 45 | |
| 101 | | 17 | |
| 102 | | 14 | |
| 103 | 784 | 115 | |
| 104 | | 25 | |
| 105 | 248 | 140 | |
| 106 | 216 | 143 | |
| 107 | 499 | 161 | |
| 108 | 509 | 149 | |
| 109 | 187 | 144 | 7 (10.0) |
| 110 | 89 | 183 | |
| 111 | 86 | 178 | |
| 112 | 130 | 211 | 17 (10.0) |
| 113 | 3992 | 66 | |
| 114 | 169 | 175 | |
| 115 | 136 | 150 | |
| 116 | 598 | 147 | |
| 117 | 222 | 87 | |
| 118 | 147 | 149 | |
| 119 | 2748 | 72 | |
| 120 | 1212 | 157 | |
| 121 | 334 | 90 | |
| 122 | 65 | 171 | |
| 123 | | 8 | |
| 124 | | 8 | |
| 125 | | 14 | |
| 126 | | 5 | |
| 127 | | 18 | |
| 128 | | 39 | |
| 129 | | 12 | |
| 130 | 58 | 180 | |
| 131 | 1818 | 104 | |
| 132 | 51 | 161 | |
| 133 | | 15 | |
| 134 | | 21 | |
| 135 | | 6 | |
| 136 | 227 | 164 | |
| 137 | 225 | 166 | |
| 138 | 2235 | 91 | |
| 139 | 1958 | 91 | |
| 140 | 1150 | 101 | |

4-OH-2-Mercapto-quinoline-3-carboxamides are known from FR2532939 for which a pharmacological action in a pain model and in an inflammatory model are described, without specifying a mechanism of action.

Recreations of the teaching of FR2532939 show, however, that such 2-mercaptoquinoline-3-carboxamides having a 4-hydroxy function have no effect in the pharmacological model in the fluorescence assay on KCNQ2/3 up to concentrations in the relevant range up to 30 μmol.

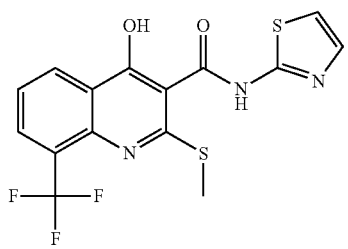

Example 4 from FR 2532939

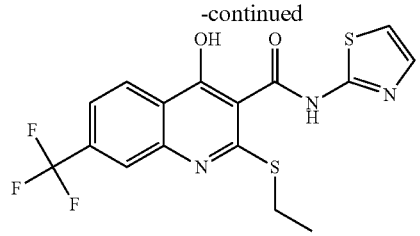

Analogues of Example 4 from FR 2532939 with $CF_3$ group in 7-rather than 8-position

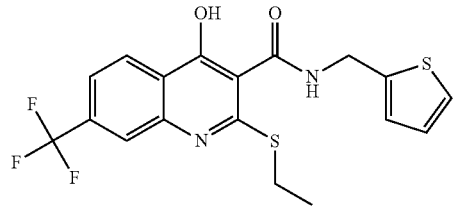

4-OH analogues of Examples 14 and 30 by reference to Example 4 of FR 2532939

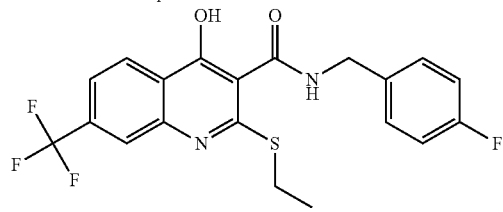

4-OH analogues of Example 77 by reference to Example 4 of FR 2532939

In the compounds according to the invention according to claim a 4-hydroxy function is excluded by an appropriate definition of $R^5$.

The invention claimed is:

1. A substituted 2-mercaptoquinoline-3-carboxamide having the formula (1):

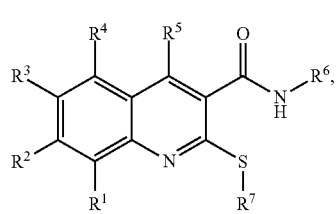

wherein $R^0$ stands for $C_{1-10}$ alkyl or $C_{2-10}$ heteroalkyl, each saturated or unsaturated, branched or unbranched, unsubstituted or mono- or polysubstituted; $C_{3-10}$ cycloalkyl or heterocyclyl, each saturated or unsaturated, unsubstituted or mono- or polysubstituted; aryl or heteroaryl, each unsubstituted or mono- or polysubstituted; $C_{1-8}$ alkyl- or $C_{2-8}$ heteroalkyl-bridged $C_{3-10}$ cycloalkyl or heterocyclyl, each saturated or unsaturated, unsubstituted or mono- or polysubstituted, wherein the alkyl or heteroalkyl chain can in each case be branched or unbranched, saturated or unsaturated, unsubstituted, mono- or polysubstituted; or $C_{1-8}$ alkyl- or $C_{2-8}$ heteroalkyl-bridged aryl or heteroaryl, each unsubstituted or mono- or polysubstituted, wherein the alkyl or heteroalkyl chain can in each case be branched or unbranched, saturated or unsaturated, unsubstituted, mono- or polysubstituted;

$R^1, R^2, R^3, R^4$ each denote independently of one another H; F; Cl; Br; I; $NO_2$; $CF_3$; CN; $R^O$; C(=O)H; C(=O)$R^O$; $CO_2$H; C(=O)O$R^O$; $CONH_2$; C(=O)NH$R^O$; C(=O)N($R^O$)$_2$; OH; O$R^O$; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$O$R^O$; O—S(=O)$_2$NH$_2$; O—S(=O)$_2$NH$R^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2$$R^O$; NH—S(=O)$_2$O$R^O$; NH—S(=O)$_2$NH$_2$; NH—S(=O)$_2$NH$R^O$; NH—S(=O)$_2$N($R^O$)$_2$; $NR^O$—S(=O)$_2$OH; $NR^O$—S(=O)$_2$$R^O$; $NR^O$—S(=O)$_2$O$R^O$; $NR^O$—S(=O)$_2$$NH_2$; $NR^O$—S(=O)$_2$NH$R^O$; $NR^O$—S(=O)$_2$N($R^O$)$_2$; SH; S$R^O$; S(=O)$R^O$; S(=O)$_2$$R^O$; S(=O)$_2$OH; S(=O)$_2$O$R^O$; S(=O)$_2$$NH_2$; S(=O)$_2$NH$R^O$; or S(=O)$_2$N($R^O$)$_2$;

$R^5$ stands for H; F; Cl; Br; I; $NO_2$; $CF_3$; CN; $R^O$; C(=O)H; C(=O)$R^O$; $CO_2$H; C(=O)O$R^O$; $CONH_2$; C(=O)NH$R^O$; C(=O)N($R^O$)$_2$; O$R^O$; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$O$R^O$; O—S(=O)$_2$$NH_2$; O—S(=O)$_2$NH$R^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2$$R^O$; NH—S(=O)$_2$O$R^O$; NH—S(=O)$_2$$NH_2$; NH—S(=O)$_2$NH$R^O$; NH—S(=O)$_2$N($R^O$)$_2$; $NR^O$—S(=O)$_2$OH; $NR^O$—S(=O)$_2$$R^O$; $NR^O$—S(=O)$_2$O$R^O$; $NR^O$—S(=O)$_2$$NH_2$; $NR^O$—S(=O)$_2$NH$R^O$; $NR^O$—S(=O)$_2$N($R^O$)$_2$; SH; S$R^O$; S(=O)$R^O$; S(=O)$_2$$R^O$; S(=O)$_2$OH; S(=O)$_2$O$R^O$; S(=O)$_2$$NH_2$; S(=O)$_2$NH$R^O$; or S(=O)$_2$N($R^O$)$_2$;

$R^6$ stands for $R^O$, with the proviso that if $R^O$ denotes heterocyclyl, saturated or unsaturated, unsubstituted or mono- or polysubstituted, or heteroaryl, unsubstituted or mono- or polysubstituted, then the heteroaryl or heterocyclyl is bound via a carbon atom of the heteroaryl or heterocyclyl;

$R^7$ stands for $R^O$, with the proviso that if $R^O$ denotes heterocyclyl, saturated or unsaturated, unsubstituted or mono- or polysubstituted, or heteroaryl, unsubstituted or mono- or polysubstituted, then the heteroaryl or heterocyclyl is bound via a carbon atom of the heteroaryl or heterocyclyl;

wherein "substituted" in the case of substitution on alkyl, heteroalkyl, heterocyclyl and cycloalkyl stands for the substitution of one or more hydrogen atoms, each independently of one another, with F; Cl; Br; I; CN; $CF_3$; =O; =NH; =C($NH_2$)$_2$; $NO_2$; $R^O$; C(=O)H; C(=O)$R^O$; $CO_2$H; C(=O)O$R^O$; $CONH_2$; C(=O)NH$R^O$; C(=O)N($R^O$)$_2$; OH; O$R^O$; —O—($C_{1-8}$ alkyl)-O—; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$O$R^O$; O—S(=O)$_2$$NH_2$; O—S(=O)$_2$NH$R^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—

NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2$$R^O$; NH—S(=O)$_2$O$R^O$; NH—S(=O)$_2$$NH_2$; NH—S(=O)$_2$NH$R^O$; NH—S(=O)$_2$N($R^O$)$_2$; $NR^O$—S(=O)$_2$OH; $NR^O$—S(=O)$_2$$R^O$; $NR^O$—S(=O)$_2$O$R^O$; $NR^O$—S(=O)$_2$$NH_2$; $NR^O$—S(=O)$_2$NH$R^O$; $NR^O$—S(=O)$_2$N($R^O$)$_2$; SH; S$R^O$; S(=O)$R^O$; S(=O)$_2$$R^O$; S(=O)$_2$H; S(=O)$_2$OH; S(=O)$_2$O$R^O$; S(=O)$_2$$NH_2$; S(=O)$_2$NH$R^O$; or S(=O)$_2$N($R^O$)$_2$;

wherein "substituted" in the case of substitution on aryl and heteroaryl stands for the substitution of one or more hydrogen atoms, each independently of one another, with F; Cl; Br; I; $NO_2$; $CF_3$; CN; $R^O$; C(=O)H; C(=O)$R^O$; $CO_2$H; C(=O)O$R^O$; $CONH_2$; C(=O)NH$R^O$; C(=O)N($R^O$)$_2$; OH; O$R^O$; —O—($C_{1-8}$ alkyl)-O—; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$O$R^O$; O—S(=O)$_2$$NH_2$; O—S(=O)$_2$NH$R^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2$$R^O$; NH—S(=O)$_2$O$R^O$; NH—S(=O)$_2$$NH_2$; NH—S(=O)$_2$NH$R^O$; NH—S(=O)$_2$N($R^O$)$_2$; $NR^O$—S(=O)$_2$OH; $NR^O$—S(=O)$_2$$R^O$; $NR^O$—S(=O)$_2$O$R^O$; $NR^O$—S(=O)$_2$$NH_2$; $NR^O$—S(=O)$_2$NH$R^O$; $NR^O$—S(=O)$_2$N($R^O$)$_2$; SH; S$R^O$; S(=O)$R^O$; S(=O)$_2$$R^O$; S(=O)$_2$OH; S(=O)$_2$O$R^O$; S(=O)$_2$$NH_2$; S(=O)$_2$NH$R^O$; or S(=O)$_2$N($R^O$)$_2$;

with the exception of the following compound:
N-benzyl-2-(3-chloro-2-hydroxypropylthio)-4-(2,4-dichlorophenyl)quinoline-3-carboxamide;

said substituted 2-mercaptoquinoline-3-carboxamide being in the form of a free compound or a salt of physiologically compatible acids or bases.

2. Substituted carboxamide according to claim 1, wherein $R^1$, $R^2$, $R^3$ and $R^4$ are each selected independently of one another from the group consisting of H; F; Cl; Br; I; $NO_2$; $CF_3$; CN; $R^O$; C(=O)($R^O$ or H); C(=O)O($R^O$ or H); C(=O)N($R^O$ or H)$_2$; OH; O$R^O$; O—($C_{1-8}$ alkyl)-OH; O—($C_{1-8}$ alkyl)-O—$C_{1-8}$ alkyl; $OCF_3$; O—C(=O)—$R^O$; N($R^O$ or H)$_2$; N($R^O$ or H)—C(=O)—$R^O$; N($R^O$ or H)—C(=O)—N($R^O$ or H)$_2$; SH; $SCF_3$; S$R^O$; S(=O)$_2$$R^O$; S(=O)$_2$O($R^O$ or H) and S(=O)$_2$—N($R^O$ or H)$_2$;

$R^5$ is selected from the group consisting of H; F; Cl; Br; I; $NO_2$; $CF_3$; CN; $R^O$; C(=O)($R^O$ or H); C(=O)O($R^O$ or H); C(=O)N($R^O$ or H)$_2$; N($R^O$ or H)$_2$; N($R^O$ or H)—C(=O)—$R^O$; N($R^O$ or H)—C(=O)—N($R^O$ or H)$_2$; SH; $SCF_3$; S$R^O$; S(=O)$_2$$R^O$; S(=O)$_2$O($R^O$ or H); and S(=O)$_2$—N($R^O$ or H)$_2$;

$R^6$ stands for $C_{1-10}$ alkyl or $C_{2-10}$ heteroalkyl, each saturated or unsaturated, branched or unbranched, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and $N(C_{1-8}$ alkyl$)_2$, $C_{3-10}$ cycloalkyl or heterocyclyl or $C_{1-8}$ alkyl- or $C_{2-8}$ heteroalkyl-bridged $C_{3-10}$ cycloalkyl or heterocyclyl, each saturated or unsaturated, unsubstituted or mono- or polysubstituted with one or more substituents selected independently of one another from the group consisting of F, Cl, Br, I, $NO_2$, CN, OH, =O, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$ and $S(=O)_2OH$;

and wherein optionally the alkyl chain or heteroalkyl chain can be branched or unbranched, saturated or unsaturated, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$ alkyl, O—$C_{1-8}$ alkyl, S—$C_{1-8}$ alkyl, NH—$C_{1-8}$ alkyl, $N(C_{1-8}$ alkyl$)_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and $N(C_{1-8}$ alkyl$)_2$; or aryl or heteroaryl or $C_{1-8}$ alkyl- or $C_{2-8}$ heteroalkyl-bridged aryl or heteroaryl, each unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$ and $S(=O)_2OH$;

and wherein optionally the alkyl chain or heteroalkyl chain can be branched or unbranched, saturated or unsaturated, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$ alkyl, O—$C_{1-8}$ alkyl, S—$C_{1-8}$ alkyl, NH—$C_{1-8}$ alkyl, $N(C_{1-8}$ alkyl$)_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and $N(C_{1-8}$ alkyl$)_2$; and $R^7$ stands for $C_{1-10}$ alkyl or $C_{2-10}$ heteroalkyl, each saturated or unsaturated, branched or unbranched, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$ alkyl, O—$C_{1-8}$ alkyl, S—$C_{1-8}$ alkyl, NH—$C_{1-8}$ alkyl, $N(C_{1-8}$ alkyl$)_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and $N(C_{1-8}$ alkyl$)_2$;

$C_{3-10}$ cycloalkyl or heterocyclyl or $C_{1-8}$ alkyl- or $C_{2-8}$ heteroalkyl-bridged $C_{3-10}$ cycloalkyl or heterocyclyl, each saturated or unsaturated, unsubstituted or mono- or polysubstituted with one or more substituents selected independently of one another from the group consisting of F, Cl, Br, I, $NO_2$, CN, OH, =O, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$, $S(=O)_2OH$, benzyl, phenyl, pyridyl, and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$; $S(=O)_2OH$;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$ alkyl, O—$C_{1-8}$ alkyl, S—$C_{1-8}$ alkyl, NH—$C_{1-8}$ alkyl, $N(C_{1-8}$ alkyl$)_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$; or aryl or heteroaryl or $C_{1-8}$ alkyl- or $C_{2-8}$ heteroalkyl-bridged aryl or heteroaryl, each unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—$C_{1-8}$ alkyl, OH and $OCF_3$; and wherein the aforementioned $C_{3-10}$ cycloalkyl or heterocyclyl can be saturated or unsaturated, unsubstituted or mono- or polysubstituted with one or more substituents selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$.

3. Substituted carboxamide according to claim 1, wherein $R^1$, $R^2$, $R^3$ and $R^4$ are each selected independently of one another from the group consisting of H; F; Cl; Br; I; $NO_2$; $CF_3$; CN; $R^0$; C(=O)($R^0$ or H); C(=O)O($R^0$ or H); C(=O)N($R^0$ or H)$_2$; OH; $OR^0$; O—($C_{1-8}$ alkyl)-OH; O—($C_{1-8}$ alkyl)-O—$C_{1-8}$ alkyl; $OCF_3$; O—C(=O)—$R^0$; N($R^0$ or H)$_2$; N($R^0$ or H)—C(=O)—$R^0$; N($R^0$ or H)—C(=O)—N($R^0$ or H)$_2$; SH; $SCF_3$; $SR^0$; S(=O)$_2R^0$; S(=O)$_2$O($R^0$ or H); and S(=O)$_2$—N($R^0$ or H)$_2$;

and $R^5$ is selected from the group consisting of H; F; Cl; Br; I; $NO_2$; $CF_3$; CN; $R^0$; C(=O)($R^0$ or H); C(=O)O($R^0$ or H); C(=O)N($R^0$ or H)$_2$; $OR^0$; —O—($C_{1-8}$ alkyl)-OH; O—($C_{1-8}$ alkyl)-O—$C_{1-8}$ alkyl; $OCF_3$; O—C(=O)—$R^0$; N($R^0$ or H)$_2$; N($R^0$ or H)—C(=O)—$R^0$; N($R^0$ or H)—C(=O)—N($R^0$ or H)$_2$; SH; $SCF_3$; $SR^0$; S(=O)$_2R^0$; S(=O)$_2$O($R^0$ or H); and S(=O)$_2$—N($R^0$ or H)$_2$.

4. Substituted carboxamide according to claim 1, wherein $R^1$, $R^2$, $R^3$ and $R^4$ are each selected independently of one another from the group consisting of H; F; Cl; Br; I; $NO_2$; $CF_3$; CN; C(=O)H; C(=O)—OH; C(=O)—$NH_2$; $C_{1-8}$ alkyl, O—$C_{1-8}$ alkyl, C(=O)$C_{1-8}$ alkyl, C(=O)O—$C_{1-8}$ alkyl, O—C(=O)—$C_{1-8}$ alkyl, C(=O)NH—$C_{1-8}$ alkyl, C(=O)N($C_{1-8}$ alkyl)$_2$, NH—$C_{1-8}$ alkyl, N($C_{1-8}$ alkyl)$_2$, NH—C(=O)$C_{1-8}$ alkyl, N($C_{1-8}$ alkyl)-C(=O)$C_{1-8}$ alkyl, S—$C_{1-8}$ alkyl, S(=O)$_2C_{1-8}$ alkyl, and S(=O)$_2$O—$C_{1-8}$ alkyl, each saturated or unsaturated, branched or unbranched, unsubstituted or mono- or polysubstituted with one or more substituents selected independently of one another from the group consisting of F, Cl, Br, I, O-methyl and OH; OH; $OCF_3$; SH; $SCF_3$; S(=O)$_2$OH; $NH_2$; $C_{3-10}$ cycloalkyl or heterocyclyl, each saturated or unsaturated, unsubstituted; benzyl, phenyl, pyridyl or thienyl, each unsubstituted or mono-, di- or trisubstituted with one, two or three substituents each selected independently of one another from the group consisting of F, Cl, Br, I, $NO_2$, $NH_2$, CN, $C_{1-8}$ alkyl, O—$C_{1-8}$ alkyl, $CF_3$, OH, $OCF_3$, C(=O)—OH, $SCF_3$ and S(=O)$_2$OH;

and $R^5$ is selected from the group consisting of H; F; Cl; Br; I; $NO_2$; $CF_3$; CN; C(=O)H; C(=O)—OH; C(=O)—$NH_2$; $C_{1-8}$ alkyl, O—$C_{1-8}$ alkyl, C(=O)$C_{1-8}$ alkyl, C(=O)O—$C_{1-8}$ alkyl, O—C(=O)—$C_{1-8}$ alkyl, C(=O)NH—$C_{1-8}$ alkyl, C(=O)N($C_{1-8}$ alkyl)$_2$, NH—$C_{1-8}$ alkyl, N($C_{1-8}$ alkyl)$_2$, NH—C(=O)$C_{1-8}$ alkyl, N($C_{1-8}$ alkyl)-C(=O)$C_{1-8}$ alkyl, S—$C_{1-8}$ alkyl, S(=O)$_2C_{1-8}$ alkyl, and S(=O)$_2$O—$C_{1-8}$ alkyl, each saturated or unsaturated, branched or unbranched, unsubstituted or mono- or polysubstituted with one or more substituents each selected independently of one another from the group consisting of F, Cl, Br, I, O-methyl and OH; $OCF_3$; SH; $SCF_3$; S(=O)$_2$OH; $NH_2$; $C_{3-10}$ cycloalkyl or heterocyclyl, each saturated or unsaturated, unsubstituted; benzyl, phenyl, pyridyl or thienyl, each unsubstituted or mono-, di- or trisubstituted with one, two or three substituents each selected independently of one another from the group consisting of F, Cl, Br, I, $NO_2$, $NH_2$, CN, $C_{1-8}$ alkyl, O—$C_{1-8}$ alkyl, $CF_3$, OH, $OCF_3$, C(=O)—OH, $SCF_3$ and S(=O)$_2$OH.

5. Substituted carboxamide according to claim 1, wherein $R^1$, $R^2$, $R^3$ and $R^4$ are each selected independently of one another from the group consisting of H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; C(=O)-methyl; C(=O)-ethyl; C(=O)—OH; C(=O)—O-methyl; C(=O)—O-ethyl; C(=O)—$NH_2$; C(=O)—N(methyl)$_2$; C(=O)—N(ethyl)$_2$; C(=O)—NH-methyl; C(=O)—NH-ethyl; C(=O)—N(methyl)(ethyl)OH; O-methyl; O-ethyl; O—($CH_2$)$_2$—O—$CH_3$; O—($CH_2$)$_2$—OH; $OCF_3$; O—C(=O)-methyl; O—C(=O)-ethyl; $NR^aR^b$, wherein $R^a$ and $R^b$ are selected independently of each other from the group consisting of H, methyl, ethyl, ($CH_2$)$_2$—O—$CH_3$ and ($CH_2$)$_2$—OH or $R^a$ and $R^b$ together with the nitrogen atom linking them form a pyrrolidinyl, piperidinyl, 4-methylpiperazinyl or morpholinyl; NHC(=O)-methyl; NHC(=O)-ethyl; SH; $SCF_3$; S-methyl; S-ethyl; S(=O)$_2$OH; S(=O)$_2$O-methyl; benzyl, phenyl, pyridyl, each unsubstituted or mono-, di- or trisubstituted with one, two or three substituents each selected independently of one another from the group consisting of F, Cl, Br, I, CN, methyl, ethyl, $CF_3$, OH, O-methyl and $OCF_3$.

6. Substituted carboxamide according to claim 1, wherein $R^5$ is selected from the group consisting of H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; C(=O)-methyl; C(=O)-ethyl; C(=O)—OH; C(=O)—O-methyl; C(=O)—O-ethyl; C(=O)—$NH_2$; C(=O)—N(methyl)$_2$; C(=O)—N(ethyl)$_2$; C(=O)—NH-methyl;

C(=O)—NH-ethyl; C(=O)—N(methyl)(ethyl)O-methyl; O-ethyl; O—($CH_2$)$_2$—O—$CH_3$; O—($CH_2$)$_2$—OH; $OCF_3$; O—C(=O)-methyl; O—C(=O)-ethyl; $NR^aR^b$, wherein $R^a$ and $R^b$ are selected independently of each other from the group consisting of H, methyl, ethyl, ($CH_2$)$_2$—O—$CH_3$, ($CH_2$)$_2$—OH, C(=O)-methyl, C(=O)-ethyl or $R^a$ and $R^b$ together with the nitrogen atom linking them form a pyrrolidinyl, piperidinyl, 4-methylpiperazinyl or morpholinyl; SH; $SCF_3$; S-methyl; S-ethyl; $S(=O)_2OH$; $S(=O)_2O$-methyl; benzyl, unsubstituted or mono-, di- or trisubstituted with one, two or three substituents each selected independently of one another from the group consisting of F, Cl, Br, I, CN, methyl, ethyl, $CF_3$, OH, O-methyl and $OCF_3$.

7. Substituted carboxamide according to claim 1, wherein $R^6$ stands for the substructure (T1)

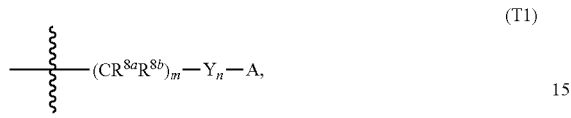

wherein
$R^{8a}$ and $R^{8b}$ stand independently of each other for H; F; Cl; Br; I; $NO_2$; $CF_3$;
CN; OH; $OCF_3$; $NH_2$; $C_{1-4}$ alkyl, O—$C_{1-4}$ alkyl, NH—$C_{1-4}$ alkyl, $N(C_{1-4}$ alkyl$)_2$, each saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$; $C_{3-10}$ cycloalkyl or heterocyclyl, each saturated or unsaturated, unsubstituted or mono- or polysubstituted with one or more substituents each selected independently of one another from the group consisting of F, Cl, Br, I, $C_{1-4}$ alkyl, OH, =O, O—$C_{1-4}$ alkyl, $OCF_3$, $NH_2$, NH—$C_{1-4}$ alkyl and $N(C_{1-4}$ alkyl$)_2$;
m stands for 0, 1, 2, 3 or 4;
Y stands for O or $NR^9$,
  wherein $R^9$ stands for H; $C_{1-4}$ alkyl, saturated or unsaturated, branched or unbranched, unsubstituted or mono- or polysubstituted with one or more substituents selected independently of one another from the group consisting of F, Cl, Br, I, $C_{1-4}$ alkyl, OH, O—$C_{1-4}$ alkyl, $OCF_3$, $NH_2$, NH—$C_{1-4}$ alkyl and $N(C_{1-4}$ alkyl$)_2$; or for $C_{3-10}$ cycloalkyl, saturated or unsaturated, unsubstituted or mono- or polysubstituted with one or more substituents each selected independently of one another from the group consisting of F, Cl, Br, I, $C_{1-4}$ alkyl, OH, O—$C_{1-4}$ alkyl, $OCF_3$, $NH_2$, NH—$C_{1-4}$ alkyl and $N(C_{1-4}$ alkyl$)_2$;
n stands for 0 or 1,
  with the proviso that n does not stand for 1 if m denotes 0;
A stands for $C_{1-8}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$; $C_{3-10}$ cycloalkyl or heterocyclyl, each saturated or unsaturated, unsubstituted or mono- or polysubstituted with one or more substituents each selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$ and $S(=O)_2OH$; aryl or heteroaryl, each unsubstituted or mono- or polysubstituted with one or more substituents each selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, $NH(C_{1-8}$ alkyl), $N(C_{1-8}$ alkyl$)_2$, SH, S—$C_{1-8}$ alkyl, $SCF_3$ and $S(=O)_2OH$.

8. Substituted carboxamide according to claim 7, wherein $R^{8a}$ and $R^{8b}$ stand independently of each other for H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; $N(methyl)_2$; NH-ethyl; $N(ethyl)_2$; or N(methyl)(ethyl);
m stands for 1, 2 or 3;
n stands for 0;
A stands for $C_{1-4}$ alkyl, saturated or unsaturated, branched or unbranched, unsubstituted or mono- or polysubstituted with one or more substituents each selected independently of one another from the group consisting of F, Cl, Br, I, OH, O—$C_{1-4}$ alkyl, $OCF_3$ and $CF_3$; $C_{3-10}$ cycloalkyl, saturated, unsubstituted; phenyl, naphthyl, pyridyl, thienyl, each unsubstituted or mono- or di- or trisubstituted with one, two or three substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, and $S(=O)_2OH$.

9. Substituted carboxamide according to claim 1, wherein $R^7$ is selected from the group consisting of methyl, ethyl, n-propyl, isopropyl, n-butyl, 2-butyl, tert-butyl, n-pentyl, isopentyl, neopentyl, n-hexyl, cyclopropyl, cyclobutyl, cyclopentyl, cyclohexyl, methyl cyclopropyl, methyl cyclobutyl, methyl cyclopentyl, methyl cyclohexyl, ethyl cyclopropyl, ethyl cyclobutyl, ethyl cyclopentyl, and ethyl cyclohexyl, each unsubstituted or mono- or polysubstituted with one or more substituents selected from the group consisting of F, Cl, Br, I, $OCF_3$, $SCF_3$, $CF_3$ and $OC_{1-8}$ alkyl; or phenyl, benzyl or phenethyl, each unsubstituted or mono- or polysubstituted with one or more substituents selected from the group consisting of F, Cl, Br, I, $OCF_3$, $SCF_3$, $CF_3$, $C_{1-8}$ alkyl, $OC_{1-8}$ alkyl and CN.

10. Substituted carboxamide according to claim 1, wherein $R^1$, $R^2$, $R^3$ and $R^4$ are each selected independently of one another from the group consisting of H; F; Cl; Br; I; $NO_2$; $CF_3$; CN; methyl; ethyl; C(=O)-methyl; OH; O-methyl; O—$(CH_2)_2$—O—$CH_3$; $OCF_3$; O—C(=O)-methyl; $NH_2$; NH—C(=O)-methyl; $N(methyl)_2$; morpholinyl; S-methyl; $SCF_3$; benzyl and phenyl, each unsubstituted;
$R^5$ is selected from the group consisting of H; F; Cl; Br; I; $NO_2$; $CF_3$; CN; methyl; ethyl; C(=O)-methyl; O-methyl; O—$(CH_2)_2$—O—$CH_3$; $OCF_3$; O—C(=O)-methyl; $NH_2$; NH—C(=O)-methyl; $N(methyl)_2$; morpholinyl; S-methyl; $SCF_3$; benzyl, unsubstituted;

$R^6$ stands for the substructure (T1-1)

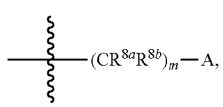

wherein
$R^{8a}$ and $R^{8b}$ stand independently of each other for H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH;

m stands for 1, 2 or 3;

A stands for methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, each unsubstituted or mono-, di- or trisubstituted with one, two or three substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH;

$R^7$ stands for $C_{1-8}$ alkyl or $C_{2-8}$ heteroalkyl, each saturated or unsaturated, branched or unbranched, unsubstituted or mono- or polysubstituted with one or more substituents each selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-8}$ cycloalkyl or heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$, and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$;

$C_{3-8}$ cycloalkyl or heterocyclyl or $C_{1-6}$ alkyl- or $C_{2-6}$ heteroalkyl-bridged $C_{3-8}$ cycloalkyl or heterocyclyl, each saturated or unsaturated, unsubstituted or mono- or polysubstituted with one or more substituents selected independently of one another from the group consisting of F, Cl, Br, I, $NO_2$, CN, OH, =O, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-8}$ cycloalkyl and heterocyclyl, wherein the aforementioned alkyl radicals can each be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$; and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$;

aryl or heteroaryl or $C_{1-6}$ alkyl- or $C_{2-6}$ heteroalkyl-bridged aryl or heteroaryl, each unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$, S(=O)$_2$OH, benzyl, phenyl, pyridyl, thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $CF_3$, $NH_2$, NH($C_{1-8}$ alkyl), N($C_{1-8}$ alkyl)$_2$, SH, S—$C_{1-8}$ alkyl, $SCF_3$ and S(=O)$_2$OH;

and wherein optionally the alkyl chain or heteroalkyl chain can be branched or unbranched, saturated or unsaturated, unsubstituted or mono- or polysubstituted with one or more substituents selected independently of one another from the group consisting of F, Cl, Br, I, $NO_2$, $CF_3$, CN, OH, =O, C(=O)—OH, $OCF_3$, $NH_2$, S(=O)$_2$OH, SH, $SCF_3$, $C_{1-8}$ alkyl, O—$C_{1-8}$ alkyl, S—$C_{1-8}$ alkyl, NH—$C_{1-8}$ alkyl, N($C_{1-8}$ alkyl)$_2$, $C_{3-10}$ cycloalkyl and heterocyclyl, wherein the aforementioned alkyl radicals can each be saturated or unsaturated, branched or unbranched, unsubstituted or mono- or polysubstituted with one or more substituents selected independently of one another from the group consisting of F, Cl, Br, I, O—$C_{1-8}$ alkyl, OH and $OCF_3$; and wherein the aforementioned $C_{3-10}$ cycloalkyl or heterocyclyl can be saturated or unsaturated, unsubstituted or mono- or polysubstituted with one or more substituents each selected independently of one another from the group consisting of F, Cl, Br, I, $C_{1-8}$ alkyl, OH, =O, O—$C_{1-8}$ alkyl, $OCF_3$, $NH_2$, NH—$C_{1-8}$ alkyl and N($C_{1-8}$ alkyl)$_2$.

11. Substituted carboxamide according to claim 1, wherein $R^1$, $R^2$, $R^3$ and $R^4$ each denote independently of one another H; F; Cl; Br; I; $CF_3$; OH; $OCF_3$; $NH_2$; SH; $SCF_3$; $C_{1-8}$ alkyl, or O—$C_{1-8}$ alkyl, each saturated or unsaturated, branched or unbranched, unsubstituted;

$R^5$ stands for H; F; Cl; Br; I; $CF_3$; $OCF_3$; $NH_2$; SH; $SCF_3$; $C_{1-8}$ alkyl, or O—$C_{1-8}$ alkyl, each saturated or unsaturated, branched or unbranched, unsubstituted;

$R^6$ stands for $C_{1-8}$ alkyl or $C_{2-8}$ heteroalkyl, each saturated, unsaturated, branched or unbranched, unsubstituted; $C_{3-10}$ cycloalkyl, saturated or unsaturated, unsubstituted; aryl or heteroaryl, each unsubstituted or mono- or polysubstituted with one or more substituents selected independently of one another from the group consisting of F, Cl, Br, I, OH, O—$C_{1-8}$ alkyl, $OCF_3$, $C_{1-8}$ alkyl, $CF_3$, SH, S—$C_{1-8}$ alkyl, $SCF_3$; $C_{1-8}$ alkyl- or $C_{2-8}$ heteroalkyl-bridged $C_{3-10}$ cycloalkyl, saturated or unsaturated, unsubstituted; or $C_{1-8}$ alkyl- or $C_{2-8}$ heteroalkyl-bridged aryl or heteroaryl, each unsubstituted or mono- or polysubstituted with one or more substituents selected independently of one another from the group consisting of F, Cl, Br, I, OH, O—$C_{1-8}$ alkyl, $OCF_3$, $C_{1-8}$ alkyl, $CF_3$, SH, S—$C_{1-8}$ alkyl, and $SCF_3$, wherein the alkyl chain can be branched or unbranched, saturated or unsaturated, unsubstituted;

$R^7$ stands for $C_{1-8}$ alkyl or $C_{2-8}$ heteroalkyl, each saturated, unsaturated, branched or unbranched, unsubstituted or mono- or polysubstituted with one or more substituents selected independently of one another from the group consisting of F, Cl, Br, I, OH, =O, O—$C_{1-8}$ alkyl;

$C_{3-10}$ cycloalkyl, saturated or unsaturated, unsubstituted; aryl or heteroaryl, each unsubstituted or mono- or polysubstituted with one or more substituents selected independently of one another from the group consisting of F, Cl, Br, I, OH, O—$C_{1-8}$ alkyl, $OCF_3$, $C_{1-8}$ alkyl, $CF_3$, $SCF_3$; $C_{1-8}$ alkyl- or $C_{2-8}$ heteroalkyl-bridged $C_{3-10}$ cycloalkyl, saturated or unsaturated, unsubstituted, wherein the alkyl chain can be branched or unbranched, saturated or unsaturated, unsubstituted; or $C_{1-8}$ alkyl- or $C_{2-8}$ heteroalkyl-bridged aryl or heteroaryl, each unsubstituted or mono- or polysubstituted with one or more substituents selected independently of one another from the group consisting of F, Cl, Br, I, OH, O—$C_{1-8}$ alkyl, $OCF_3$, $C_{1-8}$ alkyl, $CF_3$, and $SCF_3$, wherein the alkyl chain can be branched or unbranched, saturated or unsaturated, unsubstituted.

12. Substituted carboxamide according to claim 1, wherein $R^1$, $R^2$, $R^3$ and $R^4$ are each selected independently of one another from the group consisting of H, F, Cl, $CF_3$ and $OCF_3$;

$R^5$ stands for methyl, OMe or —$CH_2O$-methyl;

$R^6$ stands for the following substructure (T1)

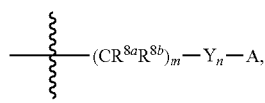

wherein
$R^{8a}$ and $R^{8b}$ stand independently of each other for H,
m stands for 1,
n for 0 and
A stands for phenyl, pyridyl or thienyl, each substituted 0, 1, 2 or 3 times with a substituent selected from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$, and $R^7$ stands for methyl, ethyl, isopropyl, tert-butyl or cyclopropyl.

13. Substituted carboxamide according to claim 1, selected from the group consisting of:

1  2-(Pentylthio)-N-(2-thienylmethyl)-3-quinoline carboxamide;
2  3-[[3-[Oxo-(2-thienylmethylamino)methyl]quinolyl]thio]propanoic acid methyl ester;
3  2-(3-Cyclohexylpropylthio)-N-(2-thienylmethyl)-3-quinoline carboxamide;
4  2-(3-Phenylpropylthio)-N-(2-thienylmethyl)-3-quinoline carboxamide;
5  2-[2-(Phenylsulfonyl)ethylthio]-N-(2-thienyl-methyl)-3-quinoline carboxamide;
6  2-[3-(4-Fluorophenyl)propylthio]-N-(2-thienylmethyl)-3-quinoline carboxamide;
7  2-(Ethylthio)-N-(2-thienylmethyl)-3-quinoline carboxamide;
8  2-[2-(Phenylsulfonyl)ethylthio]-N-(2-thienyl-methyl)-6-(trifluoromethyl)-3-quinoline carboxamide;
9  2-[2-(Phenylsulfonyl)ethylthio]-N-(2-thienylmethyl)-7-(trifluoromethyl)-3-quinoline carboxamide;
10  2-[2-(Phenylsulfonyl)ethylthio]-N-(2-thienylmethyl)-5-(trifluoromethyl)-3-quinoline carboxamide;
11  2-(Pentylthio)-N-(2-thienylmethyl)-6-(trifluoromethyl)-3-quinoline carboxamide;
12  2-(Ethylthio)-N-(2-thienylmethyl)-6-(trifluoromethyl)-3-quinoline carboxamide;
13  N-(2-Thienylmethyl)-2-[2-[3-(trifluoromethyl)-phenyl]sulfonylethylthio]-3-quinoline carboxamide;
14  2-(Ethylthio)-N-(2-thienylmethyl)-7-(trifluoromethyl)-3-quinoline carboxamide;
15  2-(Pentylthio)-N-(2-thienylmethyl)-7-(trifluoromethyl)-3-quinoline carboxamide;
16  2-[2-(4-Fluorophenyl)sulfonylethylthio]-N-(2-thienylmethyl)-3-quinoline carboxamide;
17  2-[2-(p-Tolylsulfonyl)ethylthio]-N-(2-thienylmethyl)-3-quinoline carboxamide;
18  2-[2-(p-Tolylthio)ethylthio]-N-(2-thienylmethyl)-3-quinoline carboxamide;
19  2-[2-(Phenylsulfonyl)ethylthio]-N-(cyclohexylmethyl)-3-quinoline carboxamide;
20  2-[3-(p-Tolyl)propylthio]-N-(2-thienylmethyl)-3-quinoline carboxamide;
21  2-[2-(Phenylthio)ethylthio]-N-(2-thienylmethyl)-3-quinoline carboxamide;
22  2-[2-(Phenylsulfonyl)ethylthio]-N-(2-cyclohexylethyl)-3-quinoline carboxamide;
23  2-[2-(Phenylsulfonyl)ethylthio]-N-(3,3-dimethylbutyl)-3-quinoline carboxamide;
24  2-[2-[(4-Fluorophenyl)thio]ethylthio]-N-(2-thienylmethyl)-3-quinoline carboxamide;
N-(3,3-Dimethylbutyl)-2-(ethylthio)-4-methyl-7-(trifluoromethyl)-3-quinoline carboxamide;
26  3-(3-(Thiophen-2-ylmethylcarbamoyl)-6-(trifluoromethyl)quinolin-2-ylthio)propanoic acid methyl ester;
27  3-(3-(Thiophen-2-ylmethylcarbamoyl)-7-(trifluoromethyl)quinolin-2-ylthio)propanoic acid methyl ester;
28  N-(2,2-Dimethylpropyl)-2-ethylsulfanyl-4-methyl-7-(trifluoromethyl)-quinoline-3-carboxamide;
29  N-(Cycloheptylmethyl)-2-ethylsulfanyl-4-methyl-7-(trifluoromethyl)-quinoline-3-carboxamide;
31  N-[(3,4-Difluorophenyl)-methyl]-2-ethylsulfanyl-4-methyl-7-(trifluoromethyl)-quinoline-3-carboxamide;
32  N-[(2,4-Difluorophenyl)-methyl]-2-ethylsulfanyl-4-methyl-7-(trifluoromethyl)-quinoline-3-carboxamide;
33  2-Ethylsulfanyl-4-methyl-7-(trifluoromethyl)-N-[(3,4,5-trifluorophenyl)-methyl]-quinoline-3-carboxamide;
34  2-Ethylsulfanyl-4-methyl-7-(trifluoromethyl)-N-[(2,4,5-trifluorophenyl)-methyl]-quinoline-3-carboxamide;
35  2-Ethylsulfanyl-4-methyl-N-(pyridin-4-yl-methyl)-7-(trifluoromethyl)-quinoline-3-carboxamide;
36  N-[(4-tert-Butylphenyl)-methyl]-2-ethylsulfanyl-4-methyl-7-(trifluoromethyl)-quinoline-3-carboxamide;

37 2-Ethylsulfanyl-4-methyl-N-(3-methylbutyl)-7-(trifluoromethyl)-quinoline-3-carboxamide;
38 2-Ethylsulfanyl-4-methyl-7-(trifluoromethyl)-N-[[3-(trifluoromethyl)phenyl]-methyl]-quinoline-3-carboxamide;
39 2-Ethylsulfanyl-4-methyl-N-phenethyl-7-(trifluoromethyl)-quinoline-3-carboxamide;
40 2-Ethylsulfanyl-4-methyl-N-(3-phenylpropyl)-7-(trifluoromethyl)-quinoline-3-carboxamide;
41 2-Ethylsulfanyl-4-methyl-N-(pyridin-2-yl-methyl)-7-(trifluoromethyl)-quinoline-3-carboxamide;
42 2-Ethylsulfanyl-4-methyl-N-(pyridin-3-yl-methyl)-7-(trifluoromethyl)-quinoline-3-carboxamide;
43 2-Ethylsulfanyl-4-methyl-N-(naphthalen-2-yl-methyl)-7-(trifluoromethyl)-quinoline-3-carboxamide;
44 2-Ethylsulfanyl-4-methyl-N-(thiazol-2-yl-methyl)-7-(trifluoromethyl)-quinoline-3-carboxamide;
45 2-Ethylsulfanyl-4-methyl-N-([1,3,4]oxadiazol-2-yl-methyl)-7-(trifluoromethyl)-quinoline-3-carboxamide;
47 N-[(3-Fluorophenyl)-methyl]-2-(isopropylsulfanyl)-4-methyl-7-(trifluoromethyl)-quinoline-3-carboxamide;
48 2-(Cyclopentylsulfanyl)-N-[(3-fluorophenyl)-methyl]-4-methyl-7-(trifluoromethyl)-quinoline-3-carboxamide;
49 2-(Butylsulfanyl)-N-[(3-fluorophenyl)-methyl]-4-methyl-7-(trifluoromethyl)-quinoline-3-carboxamide;
50 N-[(3-Fluorophenyl)-methyl]-4-methyl-2-(pentylsulfanyl)-7-(trifluoromethyl)-quinoline-3-carboxamide;
51 N-[(3-Fluorophenyl)-methyl]-4-methyl-2-(1-methyl-propylsulfanyl)-7-(trifluoromethyl)-quinoline-3-carboxamide;
52 2-(Cyclohexylsulfanyl)-N-[(3-fluorophenyl)-methyl]-4-methyl-7-(trifluoromethyl)-quinoline-3-carboxamide;
53 N-(2-Cyclopentylethyl)-2-ethylsulfanyl-4-methyl-7-(trifluoromethyl)-quinoline-3-carboxamide;
54 N-(3-Cyclopentylpropyl)-2-ethylsulfanyl-4-methyl-7-(trifluoromethyl)-quinoline-3-carboxamide;
55 2-Ethylsulfanyl-4-methyl-7-(trifluoromethyl)-N-[[4-(trifluoromethyl)phenyl]-methyl]-quinoline-3-carboxamide;
56 N-[(3-tert-Butylphenyl)-methyl]-2-ethylsulfanyl-4-methyl-7-(trifluoromethyl)-quinoline-3-carboxamide;
57 2-Ethylsulfanyl-4-methyl-N-(4-methylpentyl)-7-(trifluoromethyl)-quinoline-3-carboxamide;
58 2-Benzylsulfanyl-N-[(3-fluorophenyl)-methyl]-4-methyl-7-(trifluoromethyl)-quinoline-3-carboxamide;
59 2-Ethylsulfanyl-N-[(3-fluoro-2-methoxyphenyl)-methyl]-4-methyl-7-(trifluoromethyl)-quinoline-3-carboxamide;
60 2-Ethylsulfanyl-N-[(5-fluoro-2-methoxyphenyl)-methyl]-4-methyl-7-(trifluoromethyl)-quinoline-3-carboxamide;
61 N-[(3,4-Dimethyl phenyl)-methyl]-2-ethylsulfanyl-4-methyl-7-(trifluoromethyl)-quinoline-3-carboxamide;
62 2-Ethylsulfanyl-4-methyl-7-(trifluoromethyl)-N-[[4-(trifluoromethylsulfanyl)-phenyl]-methyl]-quinoline-3-carboxamide;
63 N-(Cyclohexylmethyl)-2-ethylsulfanyl-4-methyl-7-(trifluoromethyl)-quinoline-3-carboxamide;
64 2-Ethylsulfanyl-4-methyl-N-(tetrahydropyran-2-yl-methyl)-7-(trifluoromethyl)-quinoline-3-carboxamide;
65 2-Ethylsulfanyl-4-methyl-N-propyl-7-(trifluoromethyl)-quinoline-3-carboxamide;
66 N-Butyl-2-ethylsulfanyl-4-methyl-7-(trifluoromethyl)-quinoline-3-carboxamide;
67 2-Ethylsulfanyl-N-(2-methoxyethyl)-4-methyl-7-(trifluoromethyl)-quinoline-3-carboxamide;
68 2-Ethylsulfanyl-4-methyl-N-pentyl-7-(trifluoromethyl)-quinoline-3-carboxamide;
69 2-Ethylsulfanyl-4-methyl-N-[(5-methylthiophen-2-yl)-methyl]-7-(trifluoromethyl)-quinoline-3-carboxamide;
70 2-Ethylsulfanyl-4-methyl-N-[(4-methylthiophen-2-yl)-methyl]-7-(trifluoromethyl)-quinoline-3-carboxamide;
71 N-[(5-Chlorothiophen-2-yl)-methyl]-2-ethylsulfanyl-4-methyl-7-(trifluoromethyl)-quinoline-3-carboxamide;
72 2-Ethylsulfanyl-4-methyl-N-(2-thiophen-2-yl-ethyl)-7-(trifluoromethyl)-quinoline-3-carboxamide;
73 N-(5-Bicyclo[2.2.1]heptanylmethyl)-2-ethylsulfanyl-4-methyl-7-(trifluoromethyl)-quinoline-3-carboxamide;
74 N-Benzyl-2-ethylsulfanyl-4-methyl-7-(trifluoromethyl)-quinoline-3-carboxamide;
75 2-Ethylsulfanyl-N-[(2-fluorophenyl)-methyl]-4-methyl-7-(trifluoromethyl)-quinoline-3-carboxamide;
76 2-Ethylsulfanyl-N-[(3-fluorophenyl)-methyl]-4-methyl-7-(trifluoromethyl)-quinoline-3-carboxamide;
77 2-Ethylsulfanyl-N-[(4-fluorophenyl)-methyl]-4-methyl-7-(trifluoromethyl)-quinoline-3-carboxamide;
78 N-[(2-Chlorophenyl)-methyl]-2-ethylsulfanyl-4-methyl-7-(trifluoromethyl)-quinoline-3-carboxamide;
79 N-[(3-Chlorophenyl)-methyl]-2-ethylsulfanyl-4-methyl-7-(trifluoromethyl)-quinoline-3-carboxamide;
80 N-[(4-Chlorophenyl)-methyl]-2-ethylsulfanyl-4-methyl-7-(trifluoromethyl)-quinoline-3-carboxamide;
81 2-Ethylsulfanyl-4-methyl-N-(o-tolylmethyl)-7-(trifluoromethyl)-quinoline-3-carboxamide;
82 2-Ethylsulfanyl-4-methyl-N-(m-tolylmethyl)-7-(trifluoromethyl)-quinoline-3-carboxamide;
83 2-Ethylsulfanyl-4-methyl-N-(p-tolylmethyl)-7-(trifluoromethyl)-quinoline-3-carboxamide;
84 2-Ethylsulfanyl-N-[(2-methoxyphenyl)-methyl]-4-methyl-7-(trifluoromethyl)-quinoline-3-carboxamide;
85 2-Ethylsulfanyl-N-[(3-methoxyphenyl)-methyl]-4-methyl-7-(trifluoromethyl)-quinoline-3-carboxamide;
86 2-Ethylsulfanyl-N-[(4-methoxyphenyl)-methyl]-4-methyl-7-(trifluoromethyl)-quinoline-3-carboxamide;
87 N-[(3,5-Difluorophenyl)-methyl]-2-ethylsulfanyl-4-methyl-7-(trifluoromethyl)-quinoline-3-carboxamide;
88 4-Methyl-2-methylsulfanyl-N-(thiophen-2-yl-methyl)-7-(trifluoromethyl)-quinoline-3-carboxamide;
89 2-(tert-Butylsulfanyl)-4-methyl-N-(thiophen-2-yl-methyl)-7-(trifluoromethyl)-quinoline-3-carboxamide;
90 N-(2,2-Dimethylpropyl)-2-ethylsulfanyl-7-(trifluoromethyl)-quinoline-3-carboxamide;
91 2-Ethylsulfanyl-4-methyl-N-(thiophen-2-yl-methyl)-quinoline-3-carboxamide;
92 2-Ethylsulfanyl-N-[(3-fluorophenyl)-methyl]-4-methyl-quinoline-3-carboxamide;
93 2-(tert-Butylsulfanyl)-N-[(3-fluorophenyl)-methyl]-4-methyl-7-(trifluoromethyl)-quinoline-3-carboxamide;
94 2-(tert-Butylsulfanyl)-N-[(4-fluorophenyl)-methyl]-4-methyl-7-(trifluoromethyl)-quinoline-3-carboxamide;
95 7-tert-Butyl-2-ethylsulfanyl-N-[(3-fluorophenyl)-methyl]-4-methyl-quinoline-3-carboxamide;
96 7-tert-Butyl-2-ethylsulfanyl-N-[(4-fluorophenyl)-methyl]-4-methyl-quinoline-3-carboxamide;
97 2-Ethylsulfanyl-N-[(3-fluorophenyl)-methyl]-7-methoxy-4-methyl-quinoline-3-carboxamide;

98  2-Ethylsulfanyl-N-[(4-fluorophenyl)-methyl]-7-methoxy-4-methyl-quinoline-3-carboxamide;
99  2-Ethylsulfanyl-N-[(3-fluorophenyl)-methyl]-4,6-dimethyl-quinoline-3-carboxamide;
100  2-Ethylsulfanyl-N-[(4-fluorophenyl)-methyl]-4,6-dimethyl-quinoline-3-carboxamide;
101  2-Ethylsulfanyl-N-[(3-fluorophenyl)-methyl]-6-methoxy-4-methyl-quinoline-3-carboxamide;
102  2-Ethylsulfanyl-N-[(4-fluorophenyl)-methyl]-6-methoxy-4-methyl-quinoline-3-carboxamide;
103  2-Ethylsulfanyl-N-[(3-fluorophenyl)-methyl]-4-methyl-6-(trifluoromethyl)-quinoline-3-carboxamide;
104  2-Ethylsulfanyl-N-[(4-fluorophenyl)-methyl]-4-methyl-6-(trifluoromethyl)-quinoline-3-carboxamide;
105  2-Ethylsulfanyl-7-fluoro-N-[(3-fluorophenyl)-methyl]-4-methyl-quinoline-3-carboxamide;
106  2-Ethylsulfanyl-7-fluoro-N-[(4-fluorophenyl)-methyl]-4-methyl-quinoline-3-carboxamide;
107  2-Ethylsulfanyl-N-[(3-fluorophenyl)-methyl]-4,7-dimethyl-quinoline-3-carboxamide;
108  2-Ethylsulfanyl-N-[(4-fluorophenyl)-methyl]-4,7-dimethyl-quinoline-3-carboxamide;
109  2-Ethylsulfanyl-6,7-difluoro-N-[(4-fluorophenyl)-methyl]-4-methyl-quinoline-3-carboxamide;
110  2-Ethylsulfanyl-N-(furan-2-yl-methyl)-4-methyl-7-(trifluoromethyl)-quinoline-3-carboxamide;
111  2-Ethylsulfanyl-4-methyl-N-[(5-methyl-furan-2-yl)-methyl]-7-(trifluoromethyl)-quinoline-3-carboxamide;
113  2-Ethylsulfanyl-N-[(3-hydroxyphenyl)-methyl]-4-methyl-7-(trifluoromethyl)-quinoline-3-carboxamide;
114  N-[(3-Fluorophenyl)-methyl]-4-methyl-2-methylsulfanyl-7-(trifluoromethyl)-quinoline-3-carboxamide;
115  N-[(4-Fluorophenyl)-methyl]-4-methyl-2-methylsulfanyl-7-(trifluoromethyl)-quinoline-3-carboxamide;
116  2-Ethylsulfanyl-6-fluoro-N-[(3-fluorophenyl)-methyl]-4-methyl-quinoline-3-carboxamide;
117  2-Ethylsulfanyl-6-fluoro-N-[(4-fluorophenyl)-methyl]-4-methyl-quinoline-3-carboxamide;
118  2-Ethylsulfanyl-6,7-difluoro-N-[(3-fluorophenyl)-methyl]-4-methyl-quinoline-3-carboxamide;
119  2-Ethylsulfanyl-N-[(4-hydroxyphenyl)-methyl]-4-methyl-7-(trifluoromethyl)-quinoline-3-carboxamide;
120  2-Ethylsulfanyl-8-fluoro-N-[(3-fluorophenyl)-methyl]-4-methyl-quinoline-3-carboxamide;
121  2-Ethylsulfanyl-8-fluoro-N-[(4-fluorophenyl)-methyl]-4-methyl-quinoline-3-carboxamide;
123  2-Ethylsulfanyl-5-fluoro-N-[(3-fluorophenyl)-methyl]-4-methyl-quinoline-3-carboxamide;
124  2-Ethylsulfanyl-5-fluoro-N-[(4-fluorophenyl)-methyl]-4-methyl-quinoline-3-carboxamide;
125  2-Ethylsulfanyl-N-[(3-fluorophenyl)-methyl]-5-methoxy-4-methyl-quinoline-3-carboxamide;
126  2-Ethylsulfanyl-N-[(4-fluorophenyl)-methyl]-5-methoxy-4-methyl-quinoline-3-carboxamide;
127  2-Ethylsulfanyl-N-[(3-fluorophenyl)-methyl]-5-hydroxy-4-methyl-quinoline-3-carboxamide;
128  2-Ethylsulfanyl-N-[(3-fluorophenyl)-methyl]-6-hydroxy-4-methyl-quinoline-3-carboxamide;
129  2-Ethylsulfanyl-N-[(3-fluorophenyl)-methyl]-7-hydroxy-4-methyl-quinoline-3-carboxamide;
133  7-Dimethylamino-2-ethylsulfanyl-N-[(4-fluorophenyl)-methyl]-4-methyl-quinoline-3-carboxamide;
134  2-Ethylsulfanyl-N-[(3-fluorophenyl)-methyl]-4-methyl-7-morpholin-4-yl-quinoline-3-carboxamide;
135  2-Ethylsulfanyl-N-[(4-fluorophenyl)-methyl]-4-methyl-7-morpholin-4-yl-quinoline-3-carboxamide;
136  2-Ethylsulfanyl-N-[(3-fluorophenyl)-methyl]-4-methyl-8-(trifluoromethyl)-quinoline-3-carboxamide;
137  2-Ethylsulfanyl-N-[(4-fluorophenyl)-methyl]-4-methyl-8-(trifluoromethyl)-quinoline-3-carboxamide;
138  2-Ethylsulfanyl-N-[(3-fluorophenyl)-methyl]-8-methoxy-4-methyl-quinoline-3-carboxamide;
139  2-Ethylsulfanyl-N-[(4-fluorophenyl)-methyl]-8-methoxy-4-methyl-quinoline-3-carboxamide;
140  2-Ethylsulfanyl-N-[(3-fluorophenyl)-methyl]-8-hydroxy-4-methyl-quinoline-3-carboxamide;
141  7-Dimethylamino-2-ethylsulfanyl-N-[(3-fluorophenyl)-methyl]-4-methyl-quinoline-3-carboxamide;
142  2-Ethylsulfanyl-N-[(3-fluorophenyl)-methyl]-4-methyl-7-(trifluoromethyloxy)-quinoline-3-carboxamide;
143  4-Ethyl-2-ethylsulfanyl-N-[(3-fluorophenyl)-methyl]-7-(trifluoromethyl)-quinoline-3-carboxamide;
144  2-Ethylsulfanyl-N-[(3-fluorophenyl)-methyl]-4-isopropyl-7-(trifluoromethyl)-quinoline-3-carboxamide;
and the physiologically compatible salts thereof.

14. A pharmaceutical composition comprising at least one substituted carboxamide according to claim 1 or the compound N-benzyl-2-(3-chloro-2-hydroxypropylthio)-4-(2,4-dichlorophenyl)quinoline-3-carboxamide, in the form of an individual stereoisomer or a mixture thereof, in the form of a free compound and/or a physiologically compatible salt thereof, and optionally one or more suitable additives and/or auxiliary substances and/or optionally further active ingredients.

* * * * *